United States Patent
Getts et al.

(10) Patent No.: US 11,026,973 B2
(45) Date of Patent: *Jun. 8, 2021

(54) ENGINEERED PHAGOCYTIC RECEPTOR COMPOSITIONS AND METHODS OF USE THEREOF

(71) Applicant: Myeloid Therapeutics, Inc., Boston, MA (US)

(72) Inventors: Daniel Getts, Westminster, MA (US); Yuxiao Wang, San Francisco, CA (US)

(73) Assignee: Myeloid Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/827,381

(22) Filed: Mar. 23, 2020

(65) Prior Publication Data

US 2020/0345774 A1 Nov. 5, 2020

Related U.S. Application Data

(60) Provisional application No. 62/841,190, filed on Apr. 30, 2019.

(51) Int. Cl.
*A61K 35/15* (2015.01)
*C07K 14/705* (2006.01)
*A61P 35/00* (2006.01)
*C07K 16/28* (2006.01)

(52) U.S. Cl.
CPC .............. *A61K 35/15* (2013.01); *A61P 35/00* (2018.01); *C07K 14/70517* (2013.01); *C07K 14/70521* (2013.01); *C07K 14/70575* (2013.01); *C07K 14/70578* (2013.01); *C07K 14/70596* (2013.01); *C07K 16/2896* (2013.01); *C07K 2317/24* (2013.01); *C07K 2317/53* (2013.01); *C07K 2317/55* (2013.01); *C07K 2317/569* (2013.01); *C07K 2317/622* (2013.01); *C07K 2319/02* (2013.01); *C07K 2319/03* (2013.01); *C07K 2319/30* (2013.01)

(58) Field of Classification Search
CPC ..... A61K 35/15; A61P 35/00; C07K 16/2896; C07K 2317/622; C07K 2319/03
See application file for complete search history.

(56) References Cited

U.S. PATENT DOCUMENTS

| | | | |
|---|---|---|---|
| 5,773,244 A | 6/1998 | Ares, Jr. et al. | |
| 5,776,910 A | 7/1998 | Schreiber et al. | |
| 6,210,963 B1 | 4/2001 | Haddada et al. | |
| 7,833,789 B2 | 11/2010 | Naldini et al. | |
| 8,198,020 B2 | 6/2012 | Francois et al. | |
| 8,709,412 B2 | 4/2014 | Jones et al. | |
| 9,045,541 B2 | 6/2015 | Eckelman et al. | |
| 9,149,519 B2 | 10/2015 | Landau et al. | |
| 9,221,908 B2 | 12/2015 | Frazier et al. | |
| 9,518,116 B2 | 12/2016 | Frazier et al. | |
| 9,663,575 B2 | 5/2017 | Eckelman et al. | |
| 9,745,368 B2 | 8/2017 | Milone et al. | |
| 9,845,345 B2 | 12/2017 | Ring et al. | |
| 10,034,900 B2 | 7/2018 | Senju | |
| 10,081,680 B2 | 9/2018 | Weiskopf et al. | |
| 10,106,609 B2 | 10/2018 | Yang et al. | |
| 10,259,859 B2 | 4/2019 | Pons et al. | |
| 10,259,873 B2 | 4/2019 | Frazier et al. | |
| 10,415,017 B2 | 9/2019 | O'Neill | |
| 10,428,143 B2 | 10/2019 | Krummel et al. | |
| 2004/0053873 A1 | 3/2004 | Barman et al. | |
| 2006/0188891 A1 | 8/2006 | Bickmore, Jr. et al. | |
| 2008/0254027 A1 | 10/2008 | Bernett et al. | |
| 2011/0250203 A1 | 10/2011 | Klitgaard et al. | |
| 2011/0293603 A1 | 12/2011 | Saraiva et al. | |
| 2014/0134142 A1 | 5/2014 | Smith et al. | |
| 2014/0140989 A1 | 5/2014 | Eckelman et al. | |
| 2014/0161805 A1 | 6/2014 | Jamieson et al. | |
| 2014/0242701 A1 | 8/2014 | Shiku et al. | |
| 2015/0057161 A1 | 2/2015 | Schultze et al. | |
| 2015/0274826 A1 | 10/2015 | Frazier et al. | |
| 2016/0137733 A1 | 5/2016 | Frazier et al. | |
| 2016/0250258 A1 | 9/2016 | Delaney et al. | |
| 2016/0251435 A1 | 9/2016 | Eckelman et al. | |
| 2017/0087185 A1 | 3/2017 | Crane et al. | |
| 2017/0151281 A1 | 6/2017 | Wagner et al. | |
| 2017/0151282 A1 | 6/2017 | Discher et al. | |
| 2017/0166657 A1 | 6/2017 | O'Neill et al. | |

(Continued)

FOREIGN PATENT DOCUMENTS

| | | |
|---|---|---|
| CA | 2850380 C | 8/2015 |
| EP | 2626415 A2 | 8/2013 |
| EP | 2242512 B1 | 4/2016 |
| EP | 3197495 A1 | 8/2017 |
| EP | 2956343 B1 | 12/2018 |
| EP | 3519441 A1 | 8/2019 |
| GB | 2572005 A | 9/2019 |
| WO | WO-1995005835 A1 | 3/1995 |
| WO | WO-02077029 A2 | 10/2002 |
| WO | WO-2004050855 A2 | 6/2004 |
| WO | WO-2008011599 A2 | 1/2008 |
| WO | WO-2014153114 A1 | 9/2014 |

(Continued)

OTHER PUBLICATIONS

Burgueño-Bucio et al. The multiple faces of CD5. J Leukoc Biol. 2019;105:891-904. Jan. 24, 2019 (Year: 2019).*

(Continued)

*Primary Examiner* — Amy E Juedes
*Assistant Examiner* — Brian Hartnett
(74) *Attorney, Agent, or Firm* — Wilson Sonsini Goodrich & Rosatti

(57) ABSTRACT

The present disclosure provides compositions and methods for making and using engineered killer phagocytic cells for immunotherapy in cancer or infection by expressing a chimeric antigen receptor having an enhanced phagocytic activity, the chimeric receptor is encoded by a recombinant nucleic acid.

16 Claims, 40 Drawing Sheets

Specification includes a Sequence Listing.

(56) References Cited

U.S. PATENT DOCUMENTS

| | | |
|---|---|---|
| 2017/0226183 A1 | 8/2017 | Schiffer-Mannioui |
| 2017/0233452 A1 | 8/2017 | McIvor et al. |
| 2017/0246278 A1 | 8/2017 | Vera Valdes et al. |
| 2017/0283498 A1 | 10/2017 | Frazier et al. |
| 2017/0292118 A1 | 10/2017 | Duchateau et al. |
| 2018/0000899 A1 | 1/2018 | Francois et al. |
| 2018/0057592 A1 | 3/2018 | Frazier et al. |
| 2018/0104308 A1 | 4/2018 | Mamonkin et al. |
| 2018/0105600 A1 | 4/2018 | Pons et al. |
| 2018/0133252 A9 | 5/2018 | Wilson et al. |
| 2018/0142019 A1 | 5/2018 | Manning et al. |
| 2018/0155405 A1 | 6/2018 | Ring et al. |
| 2018/0171021 A1 | 6/2018 | Karlsson et al. |
| 2018/0186878 A1 | 7/2018 | Rosenthal |
| 2018/0221503 A1 | 8/2018 | Kadiyala et al. |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2019/0010219 A1 | 1/2019 | Short |
| 2019/0023761 A1 | 1/2019 | Pule et al. |
| 2019/0038671 A1 | 2/2019 | Fan et al. |
| 2019/0062450 A1 | 2/2019 | De Palma |
| 2019/0070277 A1 | 3/2019 | O'Neill et al. |
| 2019/0112373 A1 | 4/2019 | Manning et al. |
| 2019/0119379 A1 | 4/2019 | Gottschalk et al. |
| 2019/0119396 A1 | 4/2019 | Liu et al. |
| 2019/0144522 A1 | 5/2019 | Bari et al. |
| 2019/0169266 A1 | 6/2019 | Pons et al. |
| 2019/0233496 A1 | 8/2019 | Rosenthal |
| 2019/0240343 A1 | 8/2019 | Ahmed et al. |
| 2019/0248892 A1 | 8/2019 | Frazier et al. |
| 2019/0263928 A1 | 8/2019 | Watanabe et al. |
| 2019/0275150 A1 | 9/2019 | Pincetic et al. |
| 2019/0336615 A1 | 11/2019 | Thompson et al. |
| 2019/0345217 A1 | 11/2019 | Ma et al. |

FOREIGN PATENT DOCUMENTS

| | | | | |
|---|---|---|---|---|
| WO | WO-2016070136 A1 | | 5/2016 | |
| WO | WO-2016126608 A1 | | 8/2016 | |
| WO | WO-2016149254 A1 | | 9/2016 | |
| WO | WO-2016172606 A1 | * | 10/2016 | ............ A61K 45/06 |
| WO | WO-2017044487 A1 | | 3/2017 | |
| WO | WO-2017050884 A1 | | 3/2017 | |
| WO | WO-2017136633 A1 | | 8/2017 | |
| WO | WO-2018038684 A1 | | 3/2018 | |
| WO | WO-2018064076 A1 | * | 4/2018 | ....... C07K 14/70546 |
| WO | WO-2018140831 A2 | | 8/2018 | |
| WO | WO-2018169948 A1 | | 9/2018 | |
| WO | WO-2018231871 A1 | * | 12/2018 | ......... C07K 14/7051 |
| WO | WO-2019005641 A1 | | 1/2019 | |
| WO | WO-2019032624 A1 | | 2/2019 | |
| WO | WO-2019067328 A1 | | 4/2019 | |
| WO | WO-2019070704 A1 | | 4/2019 | |
| WO | WO-2019086512 A1 | | 5/2019 | |
| WO | WO-2019129146 A1 | | 7/2019 | |
| WO | WO-2019191332 A1 | | 10/2019 | |
| WO | WO-2019191334 A1 | | 10/2019 | |
| WO | WO-2019191340 A1 | | 10/2019 | |
| WO | WO-2020097193 A1 | * | 5/2020 | ............ C07K 16/30 |

OTHER PUBLICATIONS

Alignment SEQ ID 1+10+2 app 16827381 vSEQ ID No. 8 / WO2018231871A1 (Year: 2020).*
Ali, M. et al., "Induction of neoantigen-reactive T cells from healthy donors", Nature Protocols (2019).
Biglari, A., et al. Human monocytes expressing a CEA-specific chimeric CD64 receptor specifically target CEA-expressing tumour cells in vitro and in vivo, Gene Therapy (2006) 13, 602-610.
Corresponding PCT Application No. PCT/US2019/060052, filed Nov. 6, 2019.
De Oliveria, S, et al., "Modification of Hematopoietic Stem/Progenitor Cells with CD19-Specific Chimeric Antigen Receptros as a Novel Approach for Cancer Immunotherapy" Human Gene Therapy 24:824-839 (Oct. 2013).
Fraser, A., et al, "Development, functional characterization and validation of methodology for GMP-compliant manufacture of phagocytic macrophages: A novel cellular therapeutic for liver cirrhosis", Cyotherapy, 2017, ISSN 1465-3249.
Goudot, C. et al., "Aryl Hydrocarbon Receptro Controls Monocyte Differentiation into Dendritic Cells versus Macrophages", Sep. 19, 2017 Immunity 47, 582-596.
Morrissey, M., et al., "Chimeric antigen receptros that trigger phagocytosis", eLife 2018, pp. 1/21.
Roberts, Margo R., et al."Antigen-Specific Cytolysis by Neutrophils and NK Cells Expressing Chimeric Immune Receptros Bearing xx Signaling Domains", J Immunol 1998; 161:375-384.
Rosales, C. et al, "Phagocytosis: A Fundamental Process in Immunity", BioMed Research International, vol. 2017, Article ID 9042851, 18 pages.
Schlam, et al., "Phosphoinositide 3-kinase enables phagocytosis of large particles by terminating actin assembly through Rac/Cdc42 GRPase-activating proteins" (2015) Nature Communications.
Tsutsui, et al. "The use of microbubbles to target drug delivery" Cardiovascular Ultrasound (2004) 2:23.
Yong, C., et al, "A role for multiple chimeric antigen receptor-expressing leukocytes in antigen-specific responses to cancer" (2016) Oncotarget, vol. 7, No. 23 pp. 34582-34598.
Berger, et al., Efficient Elutriation of monocytes within a closed system (Elutra™) Journal of Immunological Methods 298 (2005) 61-72.
Bhattacharjee, J., et al., "Monocytes isolated by positive and negative magnetic sorting techniques show different molecular characteristics and immunophenotypic behaviour", F100Research (2018) pp. 1-13.
Bournazos, et al., "The Role and Function of Fcy Receptors on Myeloid Cells" Microbiol Spectr (2016) 4(6).
Calderwood, David, "Integrin Activation" Journal of Cell Science (2004) 117, pp. 657-666.
Cross, et al., "Human CD14dim) Monocytes Patrol and Sense Nucleic Acids and viruses via TLR7 and TLR8 Receptors", Immunity 33, 375-386, Sep. 24, 2010.
Geissmann, et al., "Blood Monocytes Consist of Two Principal Subsets with Distinct Migratory Properties", Immunity, vol. 19, pp. 71-82, Jul. (2003).
Getts, et al., "Microparticles bearing encephalitogenic peptides induce T-cell tolerance and ameliorate experimental autoimmune encephalomyelitis" (2012) Nat Biotechnol. 30(12) pp. 1217-1224.
Gordon, Siamon "Phagocytosis: An Immunobiologic Process" (2016) Immunity 44.(3):463-475.
Harburger, et al., "Integrin signaling at a glance" (2009) Journal of Cell Sciences 122, 159-163.
Hui, et al., "T cell constimulatory receptor CD28 is a primary target for PD-1-mediated inhibition" (2017) Science 355(6332) p. 1428-1433.
Sica, et al., "Fingolimod Immune Effects Beyond Its Sequestration Ability" Neuurol Ther (2019) 8:231-240.
Silverstein, et al., "Mechanisms of Cell Signaling by The Scavenger Receptor CD36: Implications in Atherosclerosis and Thrombosis" Transactions of the American Clinical and Climatological Association, vol. 121 (2010), vol. 121.
Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160.
Kim, et al., "Monocyte Enrichment from Leukapheresis products by using the Elutra cell separator" Transfusion, vol. 47, Dec. 2007 pp. 2290-2296.
McEver, et al., "Selectins: initiators of leucocyte adhesion and signaling at the vascular wall" Cardiovascular Research (2015) 107, pp. 331-339.

(56) References Cited

OTHER PUBLICATIONS

Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171.

Mukherjee, R. et al., "Non-Classical monocytes display inflammatory features: Validation in Sepsis and Systemic Lupus Erythematous", Scientific Reports, (2015) pp. 1-14.

Murshid, et al., "Hsp90-peptide complexes stimulate antigen presentation through the class II pathway after binding scavenger receptor SREC-I" Immunobiology (2014) 219(12) pp. 924-931.

Oviedo-Boyso, et al., "The Phosphoinositide-3-Kinase-Akt Signaling Pathway Is Important for *Staphylococcus aureus* Internalization by Endothelial Cells" (2011) Infection and Immunity, vol. 79, No. 11, p. 4569-4577.

Paslick, et al., "Identification and Characterization of a Novel Monocyte Subpopulation in Human Peripheral Blood", Article in Blood, Dec. 1989, 74: 2527-2534.

Patel, et al, "The fate and lifespan of human monocyte subsets in steady state and systemic inflammation" J. Exp. Med. (2017), vol. 214, No. 7 p. 1913-1923.

Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.

Strauss, et al., "The immunophenotype of antigen presenting cells of the mononuclear phagocyte system in a normal human liver—A systematic review" Journal of Hepatology, (2015) vol. 62, pp. 458-468.

\* cited by examiner

Vehicle

Regimen 1
(1 × 10⁶ cells)
1 infusion

Regimen 2
(6 × 10⁶ cells)
6 infusions

ENGINEERED PHAGOCYTIC RECEPTOR COMPOSITIONS AND METHODS OF USE THEREOF

CROSS REFERENCE

This application claims priority to U.S. Provisional Application No. 62/841,190, filed on Apr. 30, 2019; which is incorporated herein by reference in its entirety.

SEQUENCE LISTING

The instant application contains a Sequence Listing which has been filed electronically in ASCII format and is hereby incorporated by reference in its entirety. Said ASCII copy, created on Apr. 7, 2020, is named 56371-701_201_SL.txt and is 24,520 bytes in size.

BACKGROUND

Cellular immunotherapy is a promising new technology for fighting difficult to treat diseases, such as cancer, and persistent infections and also certain diseases that are refractory to other forms of treatment. A major breakthrough has come across with the discovery of CAR-T cell and their potential use in immunotherapy. CAR-T cells are T lymphocytes expressing a chimeric antigen receptor which helps target the T cell to specific diseased cells such as cancer cells, and induce cytotoxic response intended to kill the target cancer cell. However, several limitations along the way has slowed the progress on CAR-T cells and dampened its promise in clinical trials.

Understanding the limitations of CAR-T cells is the key to leveraging the technology and continue innovations towards better immunotherapy models. Specifically, in T cell malignancies, CAR-T cells appear to have faced a major problem. CAR-T cells and malignant T cells share surface antigen in most T cell lymphomas (TCL), therefore, CAR-T cells are subject to cytotoxicity in the same way as cancer cells. In some instances, the CAR-T products may be contaminated by malignant T cells. Additionally, T cell aplasia is a potential problem due to prolonged persistence of the CAR-T cells.

Macrophages are cells derived from the myeloid lineage and belong to the innate immune system. They are derived from blood monocytes that migrate into tissue. One of their main functions is to phagocytose microbes and clear cellular debris. They also play an important role in both the initiation and resolution of inflammation. Moreover, macrophages can display different responses, ranging from pro-inflammatory to anti-inflammatory, depending on the type of stimuli they receive from the surrounding microenvironment.

Newer avenues are therefore sought for using other cell types towards development of improved therapeutics, including but not limited to T cell malignancies.

SUMMARY

The present disclosure is related to immunotherapy using phagocytic cells of the immune system, particularly macrophages. A number of therapeutic indications could be contemplated using phagocytic cells. For example, macrophage immunotherapy could be exceedingly important in cancer, or in infections.

The present disclosure involves making and using engineered macrophages or other phagocytic cells that attack and kill diseased cells, such as cancer cells, or infected cells. Engineered macrophages and other phagocytic cells are prepared by incorporating in them via recombinant nucleic acid technology, a synthetic, recombinant nucleic acid encoding a chimeric fusion protein (CFP), that has a targeted to specific cancer antigens (or likewise, a disease target), and with enhanced phagocytosis activating modifications in the receptor that triggers phagocytosis of the targeted cell. Such chimeric fusion protein directed to enhanced phagocytosis is termed interchangeably herein as a CAR-P receptor and a phagocytic receptor fusion protein (PFP).

The present disclosure is based on the important finding macrophages overcome at least some of the limitations of a CAR-T cell, both in general and with respect to T cell cancers, by being (a) short-lived, therefore lowering the risk of prolonged persistence resulting in aplasia and immunodeficiency; (b) macrophages cannot be contaminated with T cells, and (c) can avoid fratricide because they do not express the same antigens as malignant T cells. In some respects, macrophages can be safer immunotherapy tools to target and destroy diseased cells.

Moreover, macrophages have been ubiquitously found in tumor environment and are notably the most abundant cells in the tumor. As efficient members of the immune system, macrophages are naturally engaged in clearing diseased cells. The present invention relates too augmenting macrophage function in specifically targeting and clearing diseased cells.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

DETAILED DESCRIPTION

Figure 1:
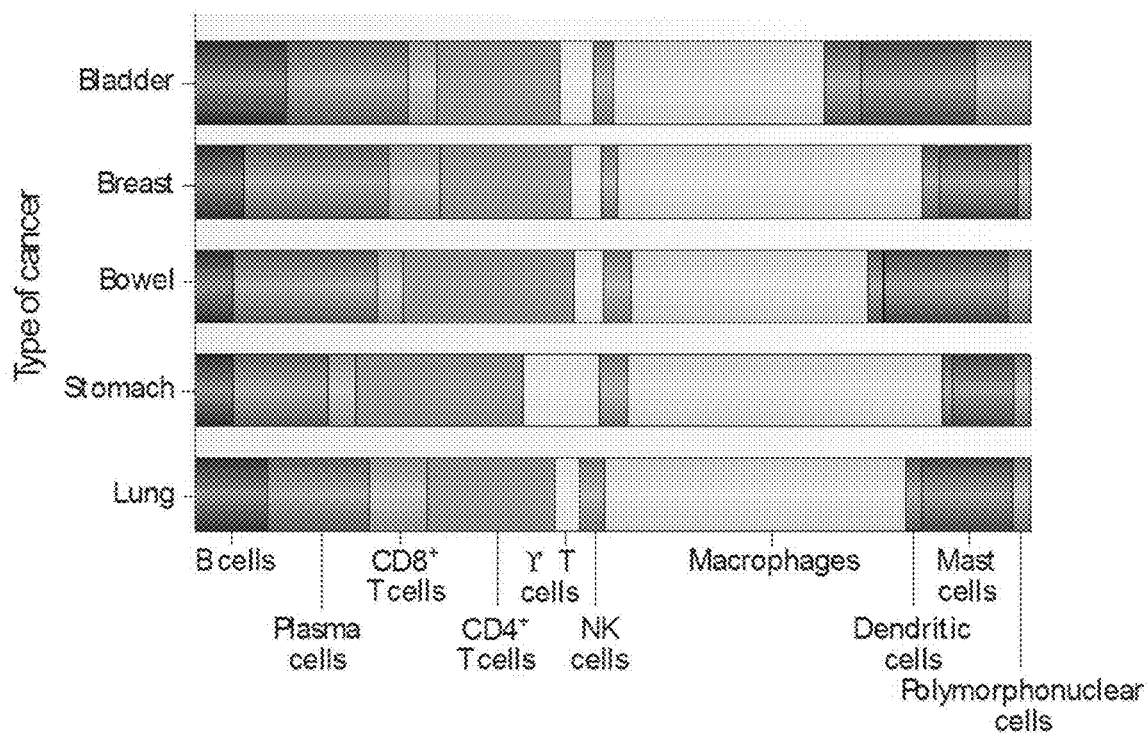
FIG. 1 depicts a diagram, indicating the presence of various cell types in different types of cancer. Macrophages are the most abundant cells in the depicted cancer types.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−20% or less, +/−10% or less, +/−5% or less, or +/−1% or less of and from the specified value, insofar such variations are appropriate to perform in the present disclosure. It is to be understood that the value to which the modifier "about" or "approximately" refers is itself also specifically disclosed.

Provided herein are engineered monocytes designed to specifically bind a target cell. The engineered monocytes can attack and kill target cells. In some embodiments, the target cell is a cancer cell.

While cancer is one exemplary embodiment described in exclusive detail in the instant disclosure, the methods and technologies described herein are contemplated to be useful in targeting an infected or otherwise diseased cell inside the body. Similarly, therapeutic and vaccine compositions using the engineered cells are described herein.

The present disclosure provides compositions and methods for treating diseases or conditions, such as cancer immunotherapy. The compositions and methods provided herein utilize human monocytes, such as macrophages, to target diseased cells, such as cancer cells. The compositions and methods provided herein can be used to eliminate diseased cells, such as cancer cells, by a variety of mechanisms, including T cell activation, antigen cross presentation and phagocytosis. For example, the monocytes can be used to sustain immunological responses against cancer cells.

Provided herein are compositions comprising a recombinant nucleic acid encoding a chimeric fusion proteins (CFP), such as a phagocytic receptor (PR) fusion protein (PFP), a scavenger receptor (SR) fusion protein (SFP) and an integrin receptor (IR) fusion protein (IFP). The CFP encoded by the recombinant nucleic acid can comprise an extracellular domain comprising an antigen binding domain that binds to an antigen of a target cell fused to a hinge domain or an extracellular domain derived from a receptor, such as CD8, CD28, CD68, a phagocytic receptor, a scavenger receptor or an integrin receptor. The CFP encoded by the recombinant nucleic acid can further comprise a transmembrane domain, such as a transmembrane domain derived from CD8, CD28, CD68, a phagocytic receptor, a scavenger receptor or an integrin receptor. In some embodiments, a CFP encoded by the recombinant nucleic acid further comprises an intracellular domain, such as an intracellular domain derived from a phagocytic receptor, a scavenger receptor or an integrin receptor. For example, the intracellular domain can comprise one or more intracellular signaling domains derived from a phagocytic receptor, a scavenger receptor or an integrin receptor. For example, the intracellular domain can comprise one or more intracellular signaling domains that promote phagocytic activity, an inflammatory response, integrin activation Provided herein is a composition comprising a recombinant nucleic acid encoding a phagocytic or tethering receptor (PR) subunit comprising: (i) a transmembrane domain, and (ii) an intracellular domain comprising a phagocytic receptor intracellular signaling domain; and an extracellular antigen binding domain specific to an antigen of a target cell; wherein the transmembrane domain and the extracellular antigen binding domain are operatively linked such that antigen binding to the target by the extracellular antigen binding domain of the fused receptor activated in the intracellular signaling domain of the phagocytic receptor. Also provided here is an engineered monocyte comprising a recombinant nucleic acid encoding a phagocytic receptor (PR) fusion protein (PFP).

Provided herein is a composition comprising a recombinant nucleic acid encoding a phagocytic or tethering receptor (PR) fusion protein (PFP) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein upon binding of the PFP to the antigen of the target cell, the killing or phagocytosis activity of a cell expressing the PFP is increased by at least greater than 20% compared to a cell not expressing the PFP.

In one aspect, provided herein is a pharmaceutical composition comprising: (a) a myeloid cell comprising a recombinant polynucleic acid, wherein the recombinant polynucleic acid comprises a sequence encoding a chimeric fusion protein (CFP), the CFP comprising: (i) an extracellular domain comprising a CD5 binding domain, and (ii) a transmembrane domain operatively linked to the extracellular domain; and (b) a pharmaceutically acceptable carrier; wherein the myeloid cell expresses the CFP and exhibits at least a 1.1-fold increase in phagocytosis of a target cell expressing CD5 compared to a myeloid cell not expressing the CFP. In some embodiments, the CD5 binding domain is a CD5 binding protein that does not comprise an antigen binding fragment of an antibody, an Fab fragment, an scFv domain or an sdAb domain. In some embodiments, the CD5 binding domain comprises an scFv comprising: (i) a variable heavy chain (VH) sequence with at least 90% sequence identity to SEQ ID NO: 1; and (ii) a variable light chain (VL) sequence with at least 90% sequence identity to SEQ ID NO: 2. In some embodiments, the CFP further comprises an intracellular domain, wherein the intracellular domain comprises one or more intracellular signaling domains, and wherein a wild-type protein comprising the intracellular domain does not comprise the extracellular domain. In some embodiments, the one or more intracellular signaling domains comprises a phagocytic signaling domain. In some embodiments, the phagocytosis signaling domain comprises an intracellular signaling domain derived from a receptor other than Megf10, MerTk, FcαR, and Bai1. In some embodiments, the phagocytosis signaling domain comprises an intracellular signaling domain derived from FcγR, FcαR or FcεR. In some embodiments, the phagocytosis signaling domain comprises an intracellular signaling domain with at least 90% sequence identity to SEQ ID NO: 3. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence with at least 90% sequence identity to SEQ ID NO: 4. In some embodiments, the proinflammatory signaling domain is derived from an intracellular signaling domain of CD40. In some embodiments, the proinflammatory signaling domain comprises a sequence with at least 90% sequence identity to SEQ ID NO: 5. In some embodiments, the transmembrane domain comprises a CD8 transmembrane domain. In some embodiments, the transmembrane domain comprises a sequence with at least 90% sequence identity to SEQ ID NO: 6. In some embodiments, the extracellular domain further comprises a hinge domain derived from CD8, wherein the hinge domain is operatively linked to the transmembrane domain and the CD5 binding domain. In some embodiments, the extracellular hinge domain comprises a sequence with at least 90% sequence identity to SEQ ID NO: 7. In one embodiment of the method described herein, the CFP comprises a sequence with at least 90% sequence identity to any one of SEQ ID NOs: 8 and 10.

In some embodiments, the CFP comprises: (a) an extracellular domain comprising: (i) a scFv that specifically binds CD5, and (ii) a hinge domain derived from CD8; a hinge domain derived from CD28 or at least a portion of an extracellular domain from CD68; (b) a CD8 transmembrane domain, a CD28 transmembrane domain or a CD68 transmembrane domain; and (c) an intracellular domain comprising at least two intracellular signaling domains, wherein the at least two intracellular signaling domains comprise: (i) a first intracellular signaling domain derived from FcγR or FcεR, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. Exemplary scavenger receptors from which an intracellular signaling domain may be derived may be found in Table 2.

In some embodiments, the recombinant polynucleic acid is an mRNA or circRNA.

In some embodiments, the myeloid cell is a CD14+ cell, a CD14+CD16– cell, an M0 macrophage, an M2 macrophage, an M1 macrophage or a mosaic myeloid cell/macrophage.

In one aspect, provided herein is a method of treating cancer in a human subject in need thereof comprising administering a pharmaceutical composition to the human subject, the pharmaceutical composition comprising: (a) a myeloid cell comprising a recombinant polynucleic acid sequence, wherein the polynucleic acid sequence comprises a sequence encoding a chimeric fusion protein (CFP), the CFP comprising: (i) an extracellular domain comprising a CD5 binding domain, and (ii) a transmembrane domain operatively linked to the extracellular domain; and (b) a pharmaceutically acceptable carrier; wherein the myeloid cell expresses the CFP.

In one embodiment of the method described herein, upon binding of the CFP to CD5 expressed by a target cancer cell of the subject killing or phagocytosis activity of the myeloid cell is increased by greater than 20% compared to a myeloid cell not expressing the CFP. In one embodiment of the method described herein, growth of a tumor is inhibited in the human subject.

In one embodiment of the method described herein, the cancer is a CD5+ cancer. In one embodiment of the method described herein, the cancer is a leukemia, a T cell lymphoma, or a B cell lymphoma.

In one embodiment of the method described herein, the CD5 binding domain is a CD5 binding protein that does not comprise an antigen binding fragment of an antibody, an scFv domain, an Fab fragment, or an sdAb domain.

In one embodiment of the method described herein, the CFP further comprises an intracellular domain, wherein the intracellular domain comprises one or more intracellular signaling domains, wherein the one or more intracellular signaling domains comprises a phagocytosis signaling domain and wherein a wild-type protein comprising the intracellular domain does not comprise the extracellular domain.

In one embodiment of the method described herein, the phagocytosis signaling domain comprises an intracellular signaling domain derived from a receptor other than Megf10, MerTk, FcαR and Bai1. In one embodiment of the method described herein, the phagocytosis signaling domain comprises an intracellular signaling domain derived from FcγR, FcαR or FcεR.

In one embodiment of the method described herein, the one or more intracellular signaling domains further comprises a proinflammatory signaling domain. In one embodiment of the method described herein, the proinflammatory signaling domain comprises a PI3-kinase (PI3K) recruitment domain. In one embodiment of the method described herein, the transmembrane domain comprises a CD8 transmembrane domain. In one embodiment of the method described herein, the extracellular domain comprises a hinge domain derived from CD8, a hinge domain derived from CD28 or at least a portion of an extracellular domain from CD68.

In some embodiments, the CFP comprises: (a) an extracellular domain comprising: (i) a scFv that specifically binds CD5, and (ii) a hinge domain derived from CD8, a hinge domain derived from CD28 or at least a portion of an extracellular domain from CD68; (b) a CD8 transmembrane domain, a CD28 transmembrane domain or a CD68 transmembrane domain; and (c) an intracellular domain comprising at least two intracellular signaling domains, wherein the at least two intracellular signaling domains comprise: (i) a first intracellular signaling domain derived from FcγR or FcεR, and (ii) a second intracellular signaling domain that: (A) comprises a PI3K recruitment domain, or (B) is derived from CD40. In one embodiment of the method described herein, the recombinant nucleic acid is mRNA or circRNA. In one embodiment of the method described herein, the myeloid cell is a CD14+ cell, a CD14+CD16– cell, an M0 macrophage, an M2 macrophage, an M1 macrophage or a mosaic myeloid cell/macrophage.

In one embodiment of the method described herein, the method further comprises administering an additional therapeutic agent selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity, an agent that promotes sequestration of lymphocytes in primary and/or secondary lymphoid organs, an agent that increases concentration of naïve T cells and central memory T cells in secondary lymphoid organs, and any combination thereof.

In one embodiment of the method described herein, the myeloid cell further comprises: (a) an endogenous peptide or protein that dimerizes with the CFP, (b) a non-endogenous peptide or protein that dimerizes with the CFP; and/or (c) a second recombinant polynucleic acid sequence, wherein the second recombinant polynucleic acid sequence comprises a sequence encoding a peptide or protein that interacts with the CFP; wherein the dimerization or the interaction potentiates phagocytosis by the myeloid cell expressing the CFP as compared to a myeloid cell that does not express the CFP.

In some embodiments, the myeloid cell exhibits (i) an increase in effector activity, cross-presentation, respiratory burst, ROS production, iNOS production, inflammatory mediators, extra-cellular vesicle production, phosphatidylinositol 3,4,5-trisphosphate production, trogocytosis with the target cell expressing the antigen, resistance to CD47 mediated inhibition of phagocytosis, resistance to LILRB1 mediated inhibition of phagocytosis, or any combination thereof; and/or (ii) an increase in expression of a IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon, MHC class I protein, MHC class II protein, CD40, CD48, CD58, CD80, CD86, CD112, CD155, a TRAIL/TNF Family death receptor, B7-DC, B7-H2, LIGHT, HVEM, TL1A, 41BBL, OX40L, GITRL, CD30L, TIM1, TIM4, SLAM, PDL1, or any combination thereof.

In some embodiments, the intracellular signaling domain is derived from a phagocytic or tethering receptor or wherein the intracellular signaling domain comprises a phagocytosis activation domain. In some embodiments, the intracellular signaling domain is derived from a receptor other than a phagocytic receptor selected from Megf10, MerTk, FcR-alpha, or Bai1. In some embodiments, the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169. In some embodiments, the intracellular signaling domain comprises a pro-inflammatory signaling domain. In some embodiments, the intracellular signaling domain comprises a pro-inflammatory signaling domain that is not a PI3K recruitment domain.

Provided herein is a composition comprising a recombinant nucleic acid encoding a phagocytic or tethering receptor (PR) fusion protein (PFP) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a phagocytic receptor other than a phagocytic receptor selected from Megf10, MerTk, FcR-alpha, or Bai1.

In some embodiments, upon binding of the PFP to the antigen of the target cell, the killing activity of a cell expressing the PFP is increased by at least greater than 20% compared to a cell not expressing the PFP.

In some embodiments, the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169. In some embodiments, the intracellular signaling domain comprises a pro-inflammatory signaling domain.

Provided herein is a composition comprising a recombinant nucleic acid encoding a phagocytic or tethering receptor (PR) fusion protein (PFP) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a phagocytic receptor selected from the group consisting oflectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169.

In some embodiments, upon binding of the PFP to the antigen of the target cell, the killing activity of a cell expressing the PFP is increased by at least greater than 55% compared to a cell not expressing the PFP. In some embodiments, the intracellular signaling domain is derived from a phagocytic receptor other than a phagocytic receptor selected from Megf10, MerTk, FcR-alpha, or Bai1. In some embodiments, the intracellular signaling domain comprises a pro-inflammatory signaling domain. In some embodiments, the intracellular signaling domain comprises a pro-inflammatory signaling domain that is not a PI3K recruitment domain.

Provided herein is a composition comprising a recombinant nucleic acid encoding a phagocytic or tethering receptor (PR) fusion protein (PFP) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain comprises a pro-inflammatory signaling domain that is not a PI3K recruitment domain.

Provided herein is a composition of an engineered phagocytic receptor, that may be expressed in a cell, such as a myeloid cell, such as to generate an engineered myeloid cell. The disclosure relates to a nucleic acid encoding, for example, a plasma membrane fusion protein; comprising a phagocytic receptor or portion thereof (a phagocytic receptor (PR) fusion protein (PFP)). A phagocytic receptor fusion protein, as used herein is a recombinant protein, a non-endogenous protein, an engineered, chimeric protein and the terms are often used interchangeably herein, all referring to the various genetically engineered receptors described as part of the invention in the disclosure. In some cases, it is referred to as a recombinant chimeric protein. The recombinant chimeric protein described herein is a fusion protein, and may comprise one or more heterogeneous peptides, or subunits, fused in a recombinant protein form. The recombinant fusion and/or chimeric protein may comprise a transmembrane domain, an extracellular domain and an intracellular domain, of which one or more domains or any fractions or combinations thereof may comprise a sequence of amino acids that is from a different protein or peptide. In some cases, the phagocytic receptor fusion protein (PFP) comprises an extracellular antigen binding domain specific to an antigen of a target cell, fused to the phagocytic receptor. A target cell is, for example, a cancer cell. In some embodiments, the engineered phagocytic cell, after engulfment of the cancer cell may present the cancer antigen on its cell surface to activate a T cell. An "antigen" is a molecule capable of stimulating an immune response. Antigens recognized by T cells, whether helper T lymphocytes (T helper (TH) cells) or cytotoxic T lymphocytes (CTLs), are not recognized as intact proteins, but rather as small peptides that associate with class I or class II MHC proteins on the surface of cells. During the course of a naturally occurring immune response, antigens that are recognized in association with class II MHC molecules on antigen presenting cells (APCs) are acquired from outside the cell, internalized, and processed into small peptides that associate with the class II MHC molecules.

In some embodiments, upon binding of the PFP to the antigen of the target cell, the killing activity of a cell expressing the PFP is increased by at least greater than 20% compared to a cell not expressing the PFP. In some embodiments, the PFP functionally incorporates into a cell membrane of a cell when the PFP is expressed in the cell.

In some embodiments, the target cell expressing the antigen is a cancer cell. In some embodiments, the target cell expressing the antigen is at least 0.8 microns in diameter.

In some embodiments, a cell expressing the PFP exhibits an increase in phagocytosis of a target cell expressing the antigen compared to a cell not expressing the PFP. In some embodiments, a cell expressing the PFP exhibits at least a 1.1-fold increase in phagocytosis of a target cell expressing the antigen compared to a cell not expressing the PFP. In some embodiments, a cell expressing the PFP exhibits at least a 2-fold, 3-fold, 4-fold, 5-fold, 6-fold, 7-fold, 8-fold, 9-fold, 10-fold, 20-fold, 30-fold or 50-fold increase in phagocytosis of a target cell expressing the antigen compared to a cell not expressing the PFP. In some embodiments, a cell expressing the PFP exhibits an increase in production of a cytokine compared to a cell not expressing the PFP. In some embodiments, wherein the cytokine is selected from the group consisting of IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon and combinations thereof. In some embodiments, a cell expressing the PFP exhibits an increase in effector activity compared to a cell not expressing the PFP. In some embodiments, a cell expressing the PFP exhibits an increase in cross-presentation compared to a cell not expressing the PFP. In some embodiments, a cell expressing the PFP exhibits an increase in expression of an MHC class II protein compared to a cell not expressing the PFP In some embodiments, a cell expressing the PFP exhibits an increase in expression of CD80 compared to a cell not expressing the PFP. In some embodiments, a cell expressing the PFP exhibits an increase in expression of CD86 compared to a cell not expressing the PFP. In some embodiments, a cell expressing the PFP exhibits an increase in expression of MHC class I protein compared to a cell not expressing the PFP. In some embodiments, a cell expressing the PFP exhibits an increase in expression of TRAIL/TNF Family death receptors compared to a cell not expressing the PFP. In some embodiments, a cell expressing the PFP exhibits an increase in expression of B7-H2 compared to a cell not expressing the PFP. In some embodiments, a cell expressing the PFP exhibits an increase in expression of LIGHT compared to a cell not expressing the PFP. In some embodiments, a cell expressing the PFP exhibits an increase in expression of HVEM compared to a cell not expressing the PFP. In some embodiments, a cell expressing the PFP exhibits an increase in expression of CD40 compared to a cell not expressing the PFP. In some embodiments, a cell expressing the PFP exhibits an increase in expression of TL1A compared to a cell not expressing the PFP. In some embodiments, a cell expressing the PFP exhibits an increase in expression of 41BBL compared to a cell not expressing the PFP. In some embodiments, a cell expressing the PFP exhibits an increase in expression of OX40L compared to a cell not expressing the PFP. In some embodiments, a cell expressing the PFP exhibits an increase in expression of GITRL death receptors compared to a cell not expressing the PFP. In some embodiments, a cell expressing the PFP exhibits an increase in expression of CD30L compared to a cell not expressing the PFP. In some embodiments, a cell expressing the PFP exhibits an increase in expression of TIM4 compared to a cell not expressing the PFP. In some embodiments, a cell expressing the PFP exhibits an increase in expression of TIM1 ligand compared to a cell not expressing the PFP. In some embodiments, a cell expressing the PFP exhibits an increase in expression of SLAM compared to a cell not expressing the PFP. In some embodiments, a cell expressing the PFP exhibits an increase in expression of CD48 compared to a cell not expressing the PFP. In some embodiments, a cell expressing the PFP exhibits an increase in expression of CD58 compared to a cell not expressing the PFP. In some embodiments, a cell expressing the PFP exhibits an increase in expression of CD155 compared to a cell not expressing the PFP. In some embodiments, a cell expressing the PFP exhibits an increase in expression of CD112 compared to a cell not expressing the PFP. In some embodiments, a cell expressing the PFP exhibits an increase in expression of PDL1 compared to a cell not expressing the PFP. In some embodiments, a cell expressing the PFP exhibits an increase in expression of B7-DC compared to a cell not expressing the PFP. In some embodiments, a cell expressing the PFP exhibits an increase in respiratory burst compared to a cell not expressing the PFP. In some embodiments, a cell expressing the PFP exhibits an increase in ROS production compared to a cell not expressing the PFP. In some embodiments, a cell expressing the PFP exhibits an increase in iNOS production compared to a cell not expressing the PFP. In some embodiments, a cell expressing the PFP exhibits an increase in iNOS production compared to a cell not expressing the PFP. In some embodiments, a cell expressing the PFP exhibits an increase in extra-cellular vesicle production compared to a cell not expressing the PFP. In some embodiments, a cell expressing the PFP exhibits an increase in trogocytosis with a target cell expressing the antigen compared to a cell not expressing the PFP. In some embodiments, a cell expressing the PFP exhibits an increase in resistance to CD47 mediated inhibition of phagocytosis compared to a cell not expressing the PFP. In some embodiments, a cell expressing the PFP exhibits an increase in resistance to LILRB1 mediated inhibition of phagocytosis compared to a cell not expressing the PFP. In some embodiments, a cell expressing the PFP exhibits an increase in phosphatidylinositol 3,4,5-trisphosphate production.

In some embodiments, the extracellular domain comprises an Ig binding domain. In some embodiments, the extracellular domain comprises an IgA, IgD, IgE, IgG, IgM, FcγRI, FcγRIIA, FcγRIIB, FcγRIIC, FcγRIIIA, FcγRIIIB, FcRn, TRIM21, FcRL5 binding domain. In some embodiments, the extracellular domain comprises an FcR extracellular domain. In some embodiments, the extracellular domain comprises an FcR-alpha, FcR-beta, FcR-Epsilon or FcR-gamma extracellular domain. In some embodiments, the extracellular domain comprises an FcαR (FCAR) extracellular domain. In some embodiments, the extracellular domain comprises an FcR-beta extracellular domain. In some embodiments, the extracellular domain comprises an FcεR (FCERIA) extracellular domain. In some embodiments, the extracellular domain comprises an FcγR (FDGR1A, FCGR2A, FCGR2B, FCGR2C, FCGR3A, FCGR3B) extracellular domain In some embodiments, the extracellular domain comprises an integrin domain. In some embodiments, the extracellular domain comprises one or more integrin $\alpha 1, \alpha 2, \alpha IIb, \alpha 3, \alpha 4, \alpha 5, \alpha 6, \alpha 7, \alpha 8, \alpha 9, \alpha 10, \alpha 11, \alpha D, \alpha E, \alpha L, \alpha M, \alpha V, \alpha X, \beta 1, \beta 2, \beta 3, \beta 4, \beta 5, \beta 6, \beta 7,$ or $\beta 8$ domains.

In some embodiments, the PSR subunit further comprises an extracellular domain operatively clinked to the transmembrane domain and the extracellular antigen binding domain. In some embodiments, the extracellular domain further comprises an extracellular domain of a receptor, a hinge, a spacer or a linker. In some embodiments, the extracellular domain comprises an extracellular portion of a PSR. In some embodiments, the extracellular portion of the PSR is derived from the same PSR as the PSR intracellular signaling domain. In some embodiments, the extracellular domain comprises an extracellular domain of a scavenger receptor or an immunoglobulin domain. In some embodiments, the immunoglobulin domain comprises an extracellular domain of an immunoglobulin or an immunoglobulin hinge region. In some embodiments, the extracellular domain comprises a phagocytic engulfment marker. In some embodiments, the extracellular domain comprises a structure capable of multimeric assembly. In some embodiments, the extracellular domain comprises a scaffold for multimerization. In some embodiments, the extracellular domain is at least 10, 20, 30, 40, 50, 60, 70, 80, 90, 100, 150, 200, 300, 300, 400, or 500 amino acids in length. In some embodiments, the extracellular domain is at most 500, 400, 300, 200, or 100 amino acids in length. In some embodiments, the extracellular antigen binding domain specifically binds to the antigen of a target cell. In some embodiments, the extracellular antigen binding domain comprises an antibody domain. In some embodiments, the extracellular antigen binding domain comprises a receptor domain, antibody domain, wherein the antibody domain comprises a functional antibody fragment, a single chain variable fragment (scFv), an Fab, a single-domain antibody (sdAb), a nanobody, a VH domain, a VL domain, a VNAR domain, a VHH domain, a bispecific antibody, a diabody, or a functional fragment or a combination thereof. In some embodiments, the extracellular antigen binding domain comprises a ligand, an extracellular domain of a receptor or an adaptor. In some embodiments, the extracellular antigen binding domain comprises a single extracellular antigen binding domain that is specific for a single antigen. In some embodiments, the extracellular antigen binding domain comprises at least two extracellular antigen binding domains, wherein each of the at least two extracellular antigen binding domains is specific for a different antigen.

In some embodiments, the antigen is a cancer antigen or a pathogenic antigen or an autoimmune antigen. In some embodiments, the antigen comprises a viral antigen. In some embodiments, the antigen is a T-lymphocyte antigen. In some embodiments, the antigen is an extracellular antigen. In some embodiments, the antigen is an intracellular antigen. In some embodiments, the antigen is selected from the group consisting of Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFR-beta, SSEA-4, EGFR, NCAM, prostase, PAP, ELF2M, GM3, TEM7R, CLDN6, TSHR, GPRCSD, ALK, IGLL1 and combinations thereof. In some embodiments, the antigen is selected from the group consisting of CD2, CD3, CD4, CD5, CD7, CCR4, CD8, CD30, CD45, and CD56. In some embodiments, the antigen is an ovarian cancer antigen or a T lymphoma antigen. In some embodiments, the antigen is an integrin receptor In some embodiments, the antigen is an integrin receptor selected from the group consisting of $\alpha 1, \alpha 2, \alpha IIb, \alpha 3, \alpha 4, \alpha 5, \alpha 6, \alpha 7, \alpha 8, \alpha 9, \alpha 10, \alpha 11, \alpha D, \alpha E, \alpha L, \alpha M, \alpha V, \alpha X, \beta 1, \beta 2, \beta 3, \beta 4, \beta 5, \beta 6, \beta 7,$ and $\beta 8$. In some embodiments, the antigen comprises 2 or more antigens.

In some embodiments, the transmembrane domain and the extracellular antigen binding domain is operatively linked through a linker. In some embodiments, the transmembrane domain and the extracellular antigen binding domain is operatively linked through a linker such as the hinge region of CD8a, IgG1 or IgG4.

In some embodiments, the extracellular domain comprises a multimerization scaffold.

In some embodiments, the transmembrane domain comprises a CD8 transmembrane domain. In some embodiments, the transmembrane domain comprises a CD28 transmembrane domain. In some embodiments, the transmembrane domain comprises a CD68 transmembrane domain. In some embodiments, the transmembrane domain comprises an FcR transmembrane domain. In some embodiments, the transmembrane domain comprises an FcR gamma transmembrane domain. In some embodiments, the transmembrane domain comprises an FcR alpha transmembrane domain. In some embodiments, the transmembrane domain comprises an FcR beta transmembrane domain. In some embodiments, the transmembrane domain comprises an FcR epsilon transmembrane domain. In some embodiments, the transmembrane domain comprises a transmembrane domain from a syntaxin such as syntaxin 3 or syntaxin 4 or syntaxin 5. In some embodiments, the transmembrane domain oligomerizes with a transmembrane domain of an endogenous receptor when the PFP is expressed in a cell. In some embodiments, the transmembrane domain oligomerizes with a transmembrane domain of an exogenous receptor when the PFP is expressed in a cell. In some embodiments, the transmembrane domain dimerizes with a transmembrane domain of an endogenous receptor when the PFP is expressed in a cell. In some embodiments, the transmembrane domain dimerizes with a transmembrane domain of an exogenous receptor when the PFP is expressed in a cell. In some embodiments, the transmembrane domain is derived from a protein that is different than the protein from which the intracellular signaling domain is derived. In some embodiments, the transmembrane domain is derived from a protein that is different than the protein from which the extracellular domain is derived. In some embodiments, the transmembrane domain comprises a transmembrane domain of a phagocytic receptor. In some embodiments, the transmembrane domain and the extracellular domain are derived from the same protein. In some embodiments, the transmembrane domain is derived from the same protein as the intracellular signaling domain. In some embodiments, the recombinant nucleic acid encodes a DAP12 recruitment domain. In some embodiments, the transmembrane domain comprises a transmembrane domain that oligomerizes with DAP12.

In some embodiments, the transmembrane domain is at least 12, 13, 14, 15, 16, 17, 18, 19, 20, 21, 22, 23, 24, 25, 26, 27, 28, 29, 30, 31 or 32 amino acids in length. In some embodiments, the transmembrane domain is at most 12, 13, 14, 15, 16, 17, 18, 19, 20, 21, 22, 23, 24, 25, 26, 27, 28, 29, 30, 31 or 32 amino acids in length.

In some embodiments, the intracellular signaling domain is derived from a phagocytic receptor. In some embodiments, the intracellular signaling domain is derived from a phagocytic receptor other than a phagocytic receptor selected from Megf10, MerTk, FcR-alpha, or Bai1. In some embodiments, the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CR35, CR3, CR4, Tim-1, Tim-4 and CD169. In some embodiments, the intracellular signaling domain comprises a PI3K recruitment domain. In some embodiments, the intracellular signaling domain is derived from a scavenger receptor. In some embodiments, the intracellular domain comprises a CD47 inhibition domain. In some embodiments, the intracellular domain comprises a Rac inhibition domain, a Cdc42 inhibition domain or a GTPase inhibition domain. In some embodiments, the Rac inhibition domain, the Cdc42 inhibition domain or the GTPase inhibition domain inhibits Rac, Cdc42 or GTPase at a phagocytic cup of a cell expressing the PFP. In some embodiments, the intracellular domain comprises an F-actin disassembly activation domain, a ARHGAP12 activation domain, a ARHGAP25 activation domain or a SH3BP1 activation domain. In some embodiments, the intracellular domain comprises a phosphatase inhibition domain. In some embodiments, the intracellular domain comprises an ARP2/3 inhibition domain. In some embodiments, the intracellular domain comprises at least one ITAM domain. In some embodiments, the intracellular domain comprises at least 1, 2, 3, 4, 5, 6, 7, 8, 9, or 10 ITAM domains. In some embodiments, the intracellular domain further comprises at least one ITAM domain. In some embodiments, the intracellular domain further comprises at least one ITAM domain select from a group CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the at least one ITAM domain comprises a Src-family kinase phosphorylation site. In some embodiments, the at least one ITAM domain comprises a Syk recruitment domain. In some embodiments, the intracellular domain comprises a F-actin depolymerization activation domain. In some embodiments, the intracellular domain lacks enzymatic activity.

In some embodiments, the intracellular domain does not comprise a domain derived from a CD3 zeta intracellular domain. In some embodiments, the intracellular domain does not comprise a domain derived from a MerTK intracellular domain. In some embodiments, the intracellular domain does not comprise a domain derived from a TLR4 intracellular domain. In some embodiments, the intracellular domain comprises a CD47 inhibition domain. In some embodiments, the intracellular signaling domain comprises a domain that activates integrin such as the intracellular region of PSGL-1. In some embodiments, the intracellular signaling domain comprises a domain that activates Rap1 GTPase, such as that from EPAC and C3G. In some embodiments, the intracellular signaling domain are from paxillin. In some embodiments, the intracellular signaling domain activates focal adhesion kinase. In some embodiments, the intracellular signaling domain is derived from a single phagocytic receptor. In some embodiments, the intracellular signaling domain is derived from a single scavenger receptor. In some embodiments, the intracellular domain further comprises a phagocytosis enhancing domain.

In some embodiments, the intracellular domain comprises a pro-inflammatory signaling domain. In some embodiments, the pro-inflammatory signaling domain comprises a kinase activation domain or a kinase binding domain. In some embodiments, the pro-inflammatory signaling domain comprises an IL-1 signaling cascade activation domain. In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, an NLRP family member, NLRP1-14, NOD1, NOD2, Pyrin, AIM2, NLRC4, FCGR3A, FCERIG, CD40, a caspase domain or a pro-caspase binding domain or any combination thereof.

In some embodiments, the PFP does not comprise a full length intracellular signaling domain. In some embodiments, the intracellular domain is at least 5, 10, 20, 30, 40, 50, 60, 70, 80, 90, 100, 150, 200, 300, 300, 400, or 500 amino acids in length. In some embodiments, the intracellular domain is at most 10, 20, 30, 40, 50, 60, 70, 80, 90, 100, 150, 200, 300, 300, 400, or 500 amino acids in length.

In some embodiments, the recombinant nucleic acid encodes an FcR alpha chain extracellular domain, an FcR alpha chain transmembrane domain and/or an FcR alpha chain intracellular domain. In some embodiments, the recombinant nucleic acid encodes an FcR beta chain extracellular domain, an FcR beta chain transmembrane domain and/or an FcR beta chain intracellular domain. In some embodiments, the FcR alpha chain or the FcR beta chain forms a complex with FcR-gamma when expressed in a cell. In some embodiments, the FcR alpha chain or FcR beta chain forms a complex with endogenous FcR-gamma when expressed in a cell. In some embodiments, the FcR alpha chain or the FcR beta chain does not incorporate into a cell membrane of a cell that does not express FcR gamma. In some embodiments, the PFP does not comprise an FcR alpha chain intracellular signaling domain. In some embodiments, the PFP does not comprise an FcR beta chain intracellular signaling domain. In some embodiments, the recombinant nucleic acid encodes a TREM extracellular domain, a TREM transmembrane domain and/or a TREM intracellular domain. In some embodiments, the TREM is TREM1, TREM 2 or TREM 3.

In some embodiments, the recombinant nucleic acid comprises a sequence encoding coding a pro-inflammatory polypeptide. In some embodiments, the composition further comprises a pro-inflammatory polypeptide. In some embodiments, the pro-inflammatory polypeptide is a chemokine, cytokine and nucleotides. In some embodiments, the chemokine is selected from the group consisting of IL-1, IL3, IL5, IL-6, i18, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon. In some embodiments, the cytokine is selected from the group consisting of IL-1, IL3, IL5, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon.

In some embodiments, the recombinant nucleic acid comprises a homeostatic regulator of inflammation. In some embodiments, the homeostatic regulator of inflammation is a sequence in an untranslated region (UTR) of an mRNA. In some embodiments, the sequence in the UTR is a sequence that binds to an RNA binding protein. In some embodiments, translation is inhibited or prevented upon binding of the RNA binding protein to the sequence in an untranslated region (UTR). In some embodiments, the sequence in the UTR comprises a consensus sequence of WWWU (AUUUA)UUUW (SEQ ID NO: 23), wherein W is A or U. In some embodiments, the recombinant nucleic acid is expressed on a bicicstronic vector.

In some embodiments, the target cell is a mammalian cell. In some embodiments, the target cell is a human cell. In some embodiments, the target cell comprises a cell infected with a pathogen. In some embodiments, the target cell is a cancer cell. In some embodiments, the target cell is a cancer cell that is a lymphocyte. In some embodiments, the target cell is a cancer cell that is an ovarian cancer cell. In some embodiments, the target cell is a cancer cell that is an ovarian pancreatic cell. In some embodiments, the target cell is a cancer cell that is a glioblastoma cell.

In some embodiments, the recombinant nucleic acid is DNA. In some embodiments, the recombinant nucleic acid is RNA. In some embodiments, the recombinant nucleic acid is mRNA. In some embodiments, the recombinant nucleic acid is a circRNA. In some embodiments, the recombinant nucleic acid is a tRNA. In some embodiments, the recombinant nucleic acid is a microRNA.

Also provided herein is a vector comprising a composition described herein. In some embodiments, the vector is viral vector. In some embodiments, the viral vector is retroviral vector or a lentiviral vector. In some embodiments, the vector further comprises a promoter operably linked to at least one nucleic acid sequence encoding one or more polypeptides. In some embodiments, the vector is polycistronic. In some embodiments, each of the at least one nucleic acid sequence is operably linked to a separate promoter. In some embodiments, the vector further comprises one or more internal ribosome entry sites (IRESs). In some embodiments, the vector further comprises a 5'UTR and/or a 3'UTR flanking the at least one nucleic acid sequence encoding one or more polypeptides. In some embodiments, the vector further comprises one or more regulatory regions.

Also provided herein is a polypeptide encoded by the recombinant nucleic acid of a composition described herein.

Also provided herein is a cell comprising a composition described herein, a vector described herein or a polypeptide described herein. In some embodiments, the cell is a phagocytic cell. In some embodiments, the cell is a stem cell derived cell, myeloid cell, macrophage, a dendritic cell, lymphocyte, mast cell, monocyte, neutrophil, microglia, or an astrocyte. In some embodiments, the cell is an autologous cell. In some embodiments, the cell is an allogeneic cell. In some embodiments, wherein the cell is an M1 macrophage cell. In some embodiments, the cell is an M2 macrophage cell.

Provided herein is a pharmaceutical composition comprising a composition described herein, a vector described herein, s polypeptide described herein or a cell described herein; and a pharmaceutically acceptable excipient.

In some embodiments, the pharmaceutical composition further comprises an additional therapeutic agent. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof. In some embodiments, the pharmaceutically acceptable excipient comprises serum free media, a lipid, or a nanoparticle.

Provided herein is a method of treating a disease in a subject in need thereof comprising administering to the subject a pharmaceutical composition described herein. In some embodiments, the disease is cancer. In some embodiments, the cancer is a solid cancer. In some embodiments, the solid cancer is selected from the group consisting of ovarian cancer, suitable cancers include ovarian cancer, renal cancer, breast cancer, prostate cancer, liver cancer, brain cancer, lymphoma, leukemia, skin cancer, pancreatic cancer, colorectal cancer, lung cancer. In some embodiments, the cancer is a liquid cancer. In some embodiments, the liquid cancer is a leukemia or a lymphoma. In some embodiments, the liquid cancer is a T cell lymphoma. In some embodiments, the disease is a T cell malignancy.

In some embodiments, the method further comprises administering an additional therapeutic agent to the subject. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof.

In some embodiments, administering comprises infusing or injecting. In some embodiments, administering comprises administering directly to the solid cancer. In some embodiments, administering comprises a circRNA, mRNA, viral-, particle-, liposome-, or exosome-based delivery procedure. In some embodiments, a CD4+ T cell response or a CD8+ T cell response is elicited in the subject.

Also provided herein is a method of preparing a cell, the method comprising contacting a cell with a composition described herein, a vector described herein or a polypeptide described herein. In some embodiments, contacting comprises transducing. In some embodiments, transducing comprises chemical transfection, electroporation, nucleofection, or viral infection.

Also provided herein is a method of preparing a pharmaceutical composition comprising contacting a lipid to a composition described herein or a vector described herein. In some embodiments, contacting comprises forming a lipid nanoparticle.

Also provided herein is a method of preparing a pharmaceutical composition comprising contacting an antibody to a composition described herein or the vector described herein. In some embodiments, contacting comprises forming a lipid nanoparticle.

Definitions

An "agent" can refer to any cell, small molecule chemical compound, antibody, nucleic acid molecule, or polypeptide, or fragments thereof.

An "alteration" or "change" can refer to an increase or decrease. An alteration can be an increase or decrease of 1%, 2%, 3%, 4%, 5%, 10%, 20%, 30%, or by 40%, 50%, 60%, or even by as much as 70%, 75%, 80%, 90%, or 100%.

"Antigen presenting cell" or "APC" as used herein includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). An APC can express Major Histocompatibility complex (MHC) molecules and can display antigens complexed with MHC on its surface to be contacted and recognized by T cells, which triggers T cell activation and immune response. Professional antigen-presenting cells, notably dendritic cells, play a key role in stimulating naive T cells—but nonprofessional antigen-presenting cells, such as fibroblasts, may also contribute to this process. APCs can also cross-present peptide antigens by processing exogenous antigens and presenting the processed antigens on class I MHC molecules. Antigens that give rise to proteins that are recognized in association with class I MHC molecules are generally proteins that are produced within the cells, and these antigens are processed and associate with class I MHC molecules.

A "biologic sample" is any tissue, cell, fluid, or other material derived from an organism. As used herein, the term "sample" includes a biologic sample such as any tissue, cell, fluid, or other material derived from an organism.

"Binds" or "specifically binds" refer to a process by one biological component, for example by a receptor or an antibody recognizes and binds a "target", which may be for example a molecule, a virus, a pathogen or parts thereof, a polypeptide, fraction or parts thereof, a glycoprotein or parts thereof, but does not recognize and bind other molecules in a sample, for example, a biological sample. In some cases, binding, as used herein, refers to cognate binding. In some cases, binding, as used herein, may refer to less specific binding, but nonetheless binding of a class of targets, and is distinct from non-specific binding. Examples of less specific binding may vary and may include binding of pattern recognition molecules by monocytes, macrophages or other myeloid cells, typically by pattern recognition receptors (PRRs), (also termed scavenger receptors (SRs)). In some cases, binding may comprise that either one or both components (such as, the receptor and the target; or the antibody and the target) may be in soluble form. In some cases, binding may comprise that both components such as described above may be cell surface bound, or bound to any other surface, such as a synthetic surface, a scaffold or a plate. In the case where both the receptor and the target are in bound form, a binding may refer to binding of the two surfaces, such as a cell having the receptor, being bound by the receptor to a target on another cell, where the two cells are effectively "binding" with each other. A cell comprising the target molecule may be referred to a target cell.

The term "epitope" includes any protein determinant capable of specific binding to an antibody, antibody peptide, and/or antibody-like molecule (including but not limited to a T cell receptor) as defined herein. Epitopic determinants typically consist of chemically active surface groups of molecules such as amino acids or sugar side chains and generally have specific three dimensional structural characteristics as well as specific charge characteristics. A "T cell epitope" is a peptide sequence which can be bound by the MHC molecules of class I or II in the form of a peptide-presenting MHC molecule or MHC complex and then, in this form, be recognized and bound by cytotoxic T-lymphocytes or T-helper cells, respectively.

An engineered cell, such as an engineered myeloid cell as described herein is used to describe a cell or a myeloid cell that has at least one exogenously expressed nucleic acid sequence in the cell. Expressing an exogenous nucleic acid may be performed by various methods described elsewhere, and encompasses methods known in the art. The present disclosure relates to preparing and using engineered phagocytic cells. The present disclosure relates to, inter alia, an engineered cell comprising an exogenously expressed nucleic acid encoding, for example, a plasma membrane fusion protein; comprising a phagocytic receptor or portion thereof (a phagocytic receptor (PR) fusion protein (PFP)).

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages. The term "adaptive immune system" as described herein, refers to term of art as known to one of skill in the art. The adaptive immune system reacts to molecular structures, referred to as antigens, of the intruding organism. Unlike the innate immune system, the adaptive immune system is highly specific to a pathogen. Adaptive immunity can also provide long-lasting protection; for example, someone who recovers from measles is now protected against measles for their lifetime. There are two types of adaptive immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in T cells, of the body. Cytotoxic T cells recognize these antigens and kill the cells that harbor the antigens.

The term "immunopurification (IP)" (or immunoaffinity purification or immunoprecipitation) is a process well known in the art and is widely used for the isolation of a desired antigen from a sample. In general, the process involves contacting a sample containing a desired antigen with an affinity matrix comprising an antibody to the antigen covalently attached to a solid phase. The antigen in the sample becomes bound to the affinity matrix through an immunochemical bond. The affinity matrix is then washed to remove any unbound species. The antigen is removed from the affinity matrix by altering the chemical composition of a solution in contact with the affinity matrix. The immunopurification can be conducted on a column containing the affinity matrix, in which case the solution is an eluent. Alternatively, the immunopurification can be in a batch process, in which case the affinity matrix is maintained as a suspension in the solution. An important step in the process is the removal of antigen from the matrix. This is commonly achieved by increasing the ionic strength of the solution in contact with the affinity matrix, for example, by the addition of an inorganic salt. An alteration of pH can also be effective to dissociate the immunochemical bond between antigen and the affinity matrix.

A "ligand" is a molecule which is capable of forming a complex with another molecule, such as a receptor in a cognitive way. According to the present disclosure, a ligand is to be understood as meaning, for example, a protein, a glycoprotein, carbohydrate, lipoprotein, or any component that binds to a receptor. In some embodiments, a receptor has a specific ligand. In some embodiments, a receptor may have promiscuous binding to a its ligand, in which case it can bind to several ligands that share at least a similarity in structural configuration, charge distribution or any other physicochemical characteristic. A ligand may be a biomolecule. A ligand may be an abiotic material, for example, $TiO_2$ is the ligand for a scavenger receptor SRA1.

The term "major histocompatibility complex (MHC)", "MHC molecules", or "MHC proteins" refers to proteins capable of binding antigenic peptides resulting from the proteolytic cleavage of protein antigens inside phagocytes or antigen presenting cells and for the purpose of presentation to and activation of T lymphocytes. Such antigenic peptides represent T cell epitopes. The human MHC is also called the HLA complex. Thus, the term "human leukocyte antigen (HLA) system", "HLA molecules" or "HLA proteins" refers to a gene complex encoding the MHC proteins in humans. The term MHC is referred as the "H-2" complex in murine species. Those of ordinary skill in the art will recognize that the terms "major histocompatibility complex (MHC)", "MHC molecules", "MHC proteins" and "human leukocyte antigen (HLA) system", "HLA molecules", "HLA proteins" are used interchangeably herein.

HLA proteins are classified into two types, referred to as HLA class I and HLA class II. The structures of the proteins of the two HLA classes are very similar; however, they have very different functions. Class I HLA proteins are present on the surface of almost all cells of the body, including most tumor cells. Class I HLA proteins are loaded with antigens that usually originate from endogenous proteins or from pathogens present inside cells, and are then presented to naïve or cytotoxic T-lymphocytes (CTLs). HLA class II proteins are present on antigen presenting cells (APCs), including but not limited to dendritic cells, B cells, and macrophages. They mainly present peptides, which are processed from external antigen sources, e.g. outside of the cells, to helper T cells. Most of the peptides bound by the HLA class I proteins originate from cytoplasmic proteins produced in the healthy host cells of an organism itself, and do not normally stimulate an immune reaction.

In HLA class II system, phagocytes such as macrophages and immature dendritic cells take up entities by phagocytosis into phagosomes—though B cells exhibit the more general endocytosis into endosomes—which fuse with lysosomes whose acidic enzymes cleave the uptaken protein into many different peptides. Authophagy is another source of HLA class II peptides. Via physicochemical dynamics in molecular interaction with the HLA class II variants borne by the host, encoded in the host's genome, a particular peptide exhibits immunodominance and loads onto HLA class II molecules. These are trafficked to and externalized on the cell surface. The most studied subclass II HLA genes are: HLA-DPA1, HLA-DPB1, HLA-DQA1, HLA-DQB1, HLA-DRA, and HLA-DRB1.

Presentation of peptides by HLA class II molecules to CD4+ helper T cells is required for immune responses to foreign antigens. Once activated, CD4+ T cells promote B cell differentiation and antibody production, as well as CD8+ T cell (CTL) responses. CD4+ T cells also secrete cytokines and chemokines that activate and induce differentiation of other immune cells. HLA class II molecules are heterodimers of α- and β-chains that interact to form a peptide-binding groove that is more open than class I peptide-binding grooves. Peptides bound to HLA class II molecules are believed to have a 9-amino acid binding core with flanking residues on either N- or C-terminal side that overhang from the groove. These peptides are usually 12-16 amino acids in length and often contain 3-4 anchor residues at positions P1, P4, P6/7 and P9 of the binding register.

HLA alleles are expressed in codominant fashion, meaning that the alleles (variants) inherited from both parents are expressed equally. For example, each person carries 2 alleles of each of the 3 class I genes, (HLA-A, HLA-B and HLA-C) and so can express six different types of class II HLA. In the class II HLA locus, each person inherits a pair of HLA-DP genes (DPA1 and DPB1, which encode a and (3 chains), HLA-DQ (DQA1 and DQB1, for α and β chains), one gene HLA-DRα (DRA1), and one or more genes HLA-DRβ (DRB1 and DRB3, -4 or -5). HLA-DRB1, for example, has more than nearly 400 known alleles. That means that one heterozygous individual can inherit six or eight functioning class II HLA alleles: three or more from each parent. Thus, the HLA genes are highly polymorphic; many different alleles exist in the different individuals inside a population. Genes encoding HLA proteins have many possible variations, allowing each person's immune system to react to a wide range of foreign invaders. Some HLA genes have hundreds of identified versions (alleles), each of which is given a particular number. In some embodiments, the class I HLA alleles are HLA-A*02:01, HLA-B*14:02, HLA-A*23:01, HLA-E*01:01 (non-classical). In some embodiments, class II HLA alleles are HLA-DRB*01:01, HLA-DRB*01:02, HLA-DRB*11:01, HLA-DRB*15:01, and HLA-DRB*07:01.

"Myeloid cell," as used herein are used to describe broadly the cells of the myeloid lineage of the hematopoietic cell system, and excludes, for example, the lymphocytic lineage. Myeloid cells comprise, for example, cells of the granulocyte lineage and monocyte lineages. Myeloid cells are differentiated from common progenitors derived from the hematopoietic stem cells in the bone marrow. Commitment to myeloid cell lineages may be governed by activation of distinct transcription factors, and accordingly myeloid cells may be characterized as cells having a level of plasticity, which may be described as the ability to further differentiate into terminal cell types based on extracellular and intracellular stimuli. Myeloid cells can be rapidly recruited into local tissues via various chemokine receptors on their surface. Myeloid cells are responsive to various cytokines and chemokines.

A myeloid cell, for example, may be a cell that originates in the bone marrow from a hematopoietic stem cell under the influence of one or more cytokines and chemokines selected from G-CSF, GM-CSF, Flt3L, CCL2, VEGF and S100A8/9. In some embodiments, the myeloid cell is a precursor cell. In some embodiments, the myeloid cell may be a cell having characteristics of a common myeloid progenitor, or a granulocyte progenitor, a myeloblast cell, or a monocyte-dendritic cell progenitor or a combination thereof. In some cases, a myeloid cell as used herein may refer to a granulocyte or a monocyte or a precursor cell thereof. In some cases, a myeloid cell as used herein may refer to an immature granulocyte, an immature monocyte, an immature macrophage, an immature neutrophil, an immature dendritic cell. In some cases, a myeloid cell as used herein may refer to a monocyte or a pre-monocytic cell or a monocyte precursor. In some cases, a myeloid cell as used herein may refer to a monocyte having an M0 phenotype, an M1 phenotype or an M2 phenotype. In some cases, a myeloid cell as used herein may refer to a dendritic cell (DC), a mature DC, a monocyte derived DC, a plasmacytoid DC, a pre-dendritic cell, or a precursor of DC. In some cases, a myeloid cell as used herein may refer to a neutrophil, which may be a mature neutrophil, a neutrophil precursor, or a polymorphonucleocyte (PMN). In some cases, a myeloid cell as used herein may refer to a macrophage, a monocyte-derived macrophage, a tissue macrophage, a macrophage of an M0, an M1 or an M2 phenotype. In some cases, a myeloid cell as used herein may refer to a is a tumor infiltrating monocyte (TIM). In some cases, a myeloid cell as used herein may refer to a tumor associated monocyte (TAM). In some cases, a myeloid cell as used herein may refer to a myeloid derived suppressor cell (MDSC). In some cases, a myeloid cell as used herein may refer to a tissue resident macrophage. In some cases, a myeloid cell as used herein may refer to a tumor associated DC (TADC). Accordingly, a myeloid cell may express one or more of the cell surface markers, for example, CD11b, CD14, CD15, CD16, CD66, Lox-1, CD11c, CD64, CD68, CD163, CCR2, CCR5, HLA-DR, CD1c, CD83, CD141, CD209, MHC-II, CD123, CD303, CD304. In some cases, a myeloid cell as used herein may be characterized by a high or a low expression of one or more of the cell surface markers, for example, CD11b, CD14, CD15, CD16, CD66, Lox-1, CD11c, CD64, CD68, CD163, CCR2, CCR5, HLA-DR, CD1c, CD83, CD141, CD209, MHC-II, CD123, CD303, CD304 or a combination thereof.

"Phagocytosis" as used herein can be used interchangeably with "engulfment" Phagocytosis is a process by which infected cells, or cancer cells are taken up removed from the body. A phagocytic receptor is involved in the process of phagocytosis. The process of phagocytosis is closely coupled with immune response, and most importantly, the first step of the immune response, which is antigen presentation. The processing of exogenous antigens follows their uptake into professional antigen presenting cells by some type of endocytic event. Phagocytosis also facilitates antigen presentation: antigens from the phagocytosed cells or pathogen, including cancer antigens are processed and presented on the cell surface of APCs. A phagocytic cell of the present disclosure that expresses a recombinant nucleic acid encoding that binds to an antigen or an epitope on a cancer cell, and engulfs the cancer cell to remove it from the body.

A polypeptide as used herein can be a "protein", including but not limited to a glycoprotein, a lipoprotein, a cellular protein or a membrane protein. A polypeptide may comprise one or more subunits of a protein. A polypeptide may be encoded by a recombinant nucleic acid. In some embodiments, polypeptide may comprise more than one peptides in a single amino acid chain, which may be separated by a spacer, a linker or peptide cleavage sequence. A polypeptide may be a fused polypeptide. A polypeptide or a protein may comprise one or more domains. A domain is a structural portion of a protein with a defined function, a polypeptide or a protein may comprise one or more modules. A module is domain or a portion of the domain or portion of a protein with a specific function. A module may be a structural module of a protein, designated by its structural embodiments. A moiety is a portion of polypeptide, a protein or a nucleic acid, having a specific structure or perform a specific function. For example, a signaling moiety is a specific unit within the larger structure of the polypeptide or protein or a recombinant nucleic acid, which (or the protein portion encoded by it in case of a nucleic acid) engages in a signal transduction process, for example a phosphorylation. A module, a domain and a moiety, as used herein, can be used interchangeably, unless a specific structural or functional orientation is otherwise defined in the text. A motif is a structural entity in a biomolecule. A signaling motif in a protein or polypeptide, for example, refers to a stretch of amino acids on the protein or polypeptide which contain an amino acid which may be phosphorylated, dephosphorylated or can serve as a binding site of another signaling molecule. Similarly, in case of nucleic acids, for example, TNF mRNA has a conserved motif, UUAUUUAUU, in the 3'UTR to which mRNA destabilizing enzymes such as zinc-finger binding protein 36 family members bind.

A "receptor" is to be understood as meaning a biological molecule or a molecule grouping capable of binding a ligand. A receptor can serve to transmit information in a cell, a cell formation or an organism. The receptor comprises at least one receptor unit and can contain two or more receptor units, where each receptor unit can consist of a protein molecule, e.g., a glycoprotein molecule. The receptor has a structure that complements the structure of a ligand and can complex the ligand as a binding partner. Signaling information can be transmitted by conformational changes of the receptor following binding with the ligand on the surface of a cell. According to the present disclosure, a receptor can refer to proteins of MHC classes I and II capable of forming a receptor/ligand complex with a ligand, e.g., a peptide or peptide fragment of suitable length.

In some embodiments, the phagocytic receptor fusion protein may comprise an extracellular domain, which comprises an antibody or a portion thereof that can bind to a cancer antigen or a cell surface molecule on a cancer cell. The term "antibody" as used herein includes IgG (including IgG1, IgG2, IgG3, and IgG4), IgA (including IgA1 and IgA2), IgD, IgE, IgM, and IgY, and is meant to include whole antibodies, including single-chain whole antibodies, and antigen-binding (Fab) fragments thereof. Antigen-binding antibody fragments include, but are not limited to, Fab, Fab' and F(ab')2, Fd (consisting of VH and CH1), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies can be monoclonal, polyclonal, chimeric, humanized, and human monoclonal and polyclonal antibodies which, e.g., specifically bind an HLA-associated polypeptide or an HLA-peptide complex. A person of skill in the art will recognize that a variety of immunoaffinity techniques are suitable to enrich soluble proteins, such as soluble HLA-peptide complexes or membrane bound HLA-associated polypeptides, e.g., which have been proteolytically cleaved from the membrane. These include techniques in which (1) one or more antibodies capable of specifically binding to the soluble protein are immobilized to a fixed or mobile substrate (e.g., plastic wells or resin, latex or paramagnetic beads), and (2) a solution containing the soluble protein from a biological sample is passed over the antibody coated substrate, allowing the soluble protein to bind to the antibodies. The substrate with the antibody and bound soluble protein is separated from the solution, and optionally the antibody and soluble protein are disassociated, for example by varying the pH and/or the ionic strength and/or ionic composition of the solution bathing the antibodies. Alternatively, immunoprecipitation techniques in which the antibody and soluble protein are combined and allowed to form macromolecular aggregates can be used. The macromolecular aggregates can be separated from the solution by size exclusion techniques or by centrifugation.

The term "recombinant nucleic acid" refers to synthetic nucleic acid having a nucleotide sequence that is not naturally occurring. A recombinant nucleic acid may be synthesized in the laboratory. A recombinant nucleic acid is prepared by using recombinant DNA technology by using enzymatic modification of DNA, such as enzymatic restriction digestion, ligation, and DNA cloning. A recombinant nucleic acid as used herein can be DNA, or RNA. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell.

The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

The term "vectors" refers to a nucleic acid molecule capable of transporting or mediating expression of a heterologous nucleic acid. A plasmid is a species of the genus encompassed by the term "vector." A vector typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

The term "recombinant nucleic acid" refers to synthetic nucleic acid having a nucleotide sequence that is not naturally occurring. A recombinant nucleic acid may be synthesized in the laboratory. A recombinant nucleic acid is prepared by using recombinant DNA technology by using enzymatic modification of DNA, such as enzymatic restriction digestion, ligation, and DNA cloning. A recombinant nucleic acid as used herein can be DNA, or RNA. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell.

The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

The term "vectors" refers to a nucleic acid molecule capable of transporting or mediating expression of a heterologous nucleic acid. A plasmid is a species of the genus encompassed by the term "vector." A vector typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

"Treating" a subject or a patient, as described herein comprises administering a therapeutic composition, such as a drug or a metabolite, or a preventive component, or a nucleic acid, a peptide, or a protein that encodes or otherwise forms a drug, a metabolite or a preventive component. Treating comprises treating a disease or a condition or a syndrome, which may be a pathological disease, condition or syndrome, or a latent disease, condition or syndrome. In some cases, treating, as used herein may comprise administering a therapeutic vaccine. In some embodiments, the engineered phagocytic cell is administered to a patient or a subject. A cell administered to a human subject must be immunocompatible to the subject, having a matching HLA subtype that is naturally expressed in the subject. Subject specific HLA alleles or HLA genotype of a subject can be determined by any method known in the art. In exemplary embodiments, the methods include determining polymorphic gene types that can comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

As used herein, the terms "determining", "assessing", "assaying", "measuring", "detecting" and their grammatical equivalents refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

A "fragment" is a portion of a protein or nucleic acid that is substantially identical to a reference protein or nucleic acid. In some embodiments, the portion retains at least 50%, 75%, or 80%, or 90%, 95%, or even 99% of the biological activity of the reference protein or nucleic acid described herein.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

The terms "neoplasia" and "cancer" refers to any disease that is caused by or results in inappropriately high levels of cell division, inappropriately low levels of apoptosis, or both. Glioblastoma is one non-limiting example of a neoplasia or cancer. The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell.

The term "vaccine" is to be understood as meaning a composition for generating immunity for the prophylaxis and/or treatment of diseases (e.g., neoplasia/tumor/infectious agents/autoimmune diseases). Accordingly, vaccines as used herein are medicaments which comprise recombinant nucleic acids, or cells comprising and expressing a recombinant nucleic acid and are intended to be used in humans or animals for generating specific defense and protective substance by vaccination. A "vaccine composition" can include a pharmaceutically acceptable excipient, carrier or diluent. Aspects of the present disclosure relate to use of the technology in preparing a phagocytic cell-based vaccine.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent. A "pharmaceutically acceptable salt" of pooled disease specific antigens as recited herein can be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluene sulfonic, methane sulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled disease specific antigens provided herein, including those listed by Remington's Pharmaceutical Sciences, 17th ed., Mack Publishing Company, Easton, Pa., p. 1418 (1985).

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having substantial identity to an endogenous sequence are typically capable of hybridizing with at least one strand of a double-stranded nucleic acid molecule. "Hybridize" refers to when nucleic acid molecules pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152: 507). For example, stringent salt concentration can ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions can ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an exemplary embodiment, hybridization can occur at 30° C. in 750 mM NaCl, 75 mM trisodium citrate, and 1% SDS. In another exemplary embodiment, hybridization can occur at 37° C. in 500 mM NaCl, 50 mM trisodium citrate, 1% SDS, 35% formamide, and 100 μg/ml denatured salmon sperm DNA (ssDNA). In another exemplary embodiment, hybridization can occur at 42° C. in 250 mM NaCl, 25 mM trisodium citrate, 1% SDS, 50% formamide, and 200 μg/ml ssDNA. Useful variations on these conditions will be readily apparent to those skilled in the art. For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or at least about 68° C. In exemplary embodiments, wash steps can occur at 25° C. in 30 mM NaCl, 3 mM trisodium citrate, and 0.1% SDS. In other exemplary embodiments, wash steps can occur at 42° C. in 15 mM NaCl, 1.5 mM trisodium citrate, and 0.1% SDS. In another exemplary embodiment, wash steps can occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95%, 96%, 97%, 98%, or even 99% or more identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program can be used, with a probability score between e-3 and e-m° indicating a closely related sequence. A "reference" is a standard of comparison.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which refers to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "prevent", "preventing", "prevention" and their grammatical equivalents as used herein, means avoiding or delaying the onset of symptoms associated with a disease or condition in a subject that has not developed such symptoms at the time the administering of an agent or compound commences.

The term "therapeutic effect" refers to some extent of relief of one or more of the symptoms of a disorder (e.g., a neoplasia, tumor, or infection by an infectious agent or an autoimmune disease) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required.

As used herein, the term "affinity molecule" refers to a molecule or a ligand that binds with chemical specificity to an affinity acceptor peptide. Chemical specificity is the ability of a protein's binding site to bind specific ligands. The fewer ligands a protein can bind, the greater its specificity. Specificity describes the strength of binding between a given protein and ligand. This relationship can be described by a dissociation constant (KD), which characterizes the balance between bound and unbound states for the protein-ligand system.

The terms "specific binding" or "specifically binding" when used in reference to the interaction of an affinity molecule and an affinity acceptor tag or an epitope and an HLA peptide mean that the interaction is dependent upon the presence of a particular structure (e.g., the antigenic determinant or epitope) on the protein; in other words, the affinity molecule is recognizing and binding to a specific affinity acceptor peptide structure rather than to proteins in general.

Phagocytic Cells "Targeted" to Attack Diseased Cells

The present disclosure involves compositions and methods for preparing targeted killer myeloid cells; by leveraging the innate functional role in immune defense, ranging from properties related to detecting foreign bodies, particles, diseased cells, cellular debris, inflammatory signal, chemoattract; activating endogenous DAMP and PAMP signaling pathways; trigger myelopoiesis, extravasation; chemotaxis; phagocytes; pinocytosis; recruitment; engulfment; scavenging; activating intracellular oxidative burst and lysis or killing of pathogens, detecting, engulfing and killing diseased or damaged cells; removing unwanted cellular, tissue or acellular debris in vivo; antigen presentation and role in activating innate immunity; activating and modulating an immune response cascade; activating T cell repertoire; autophagy; inflammatory and non-inflammatory apoptosis; pyroptosis, immune editing to response to stress and restoration of tissue homeostasis. In one aspect, provided herein are methods and compositions to augments one or more functions of a myeloid cell for use in a therapeutic application, the one or more functions may be one or more of: detecting foreign bodies, particles, diseased cells, cellular debris, inflammatory signal, chemoattract; activating endogenous DAMP and PAMP signaling pathways; trigger myelopoiesis, extravasation; chemotaxis; phagocytes; pinocytosis; recruitment; engulfment; scavenging; activating intracellular oxidative burst and intracellular lysis or killing of pathogens, detecting, engulfing and killing diseased or damaged cells; removing unwanted cellular, tissue or acellular debris in vivo; antigen presentation and role in activating innate immunity; activating and modulating an immune response cascade; activating T cell repertoire; autophagy; inflammatory and non-inflammatory apoptosis; pyroptosis, immune editing to response to stress and restoration of tissue homeostasis. In one embodiment, the compositions and methods are also directed to augmenting the targeting, and killing function of certain myeloid cells, by genetic modification of these cells. The compositions and methods described herein are directed to creating engineered myeloid cells, wherein the engineered myeloid cells comprise at least one genetic modification, and can be directed to recognize and induce effector functions against a pathogen, a diseased cell, such as a tumor or cancer cell, such that the engineered myeloid cell is capable of recognizing, targeting, phagocytosing, killing and/or eliminating the pathogen or the diseased cell or the cancer cell, and additionally, may activate a specific immune response cascade following the phagocytosis, killing and/or eliminating the pathogen or the diseased cell.

In one aspect, myeloid cells are known to be short-lived in vivo, phenotypically diverse, sensitive, plastic, and are often found to be difficult to manipulate in vitro. For example, exogenous gene expression in monocytes have lagged behind that of other non-hematopoietic cells for many reasons. There are significant technical difficulties associated with transfecting monocytes/macrophages. As professional phagocytes, myeloid cells, such as monocytes/macrophages comprise many potent degradative enzymes that can disrupt nucleic acid integrity and make gene transfer into these cells an inefficient process. This is especially true of activated macrophages which undergo a dramatic change in their physiology following exposure to immune or inflammatory stimuli. Viral transduction of these cells has been hampered because macrophages are end-stage cells that generally do not divide; therefore, some of the vectors that depend on integration into a replicative genome have met with limited success. Furthermore, macrophages are quite responsive to "danger signals," and therefore several of the original viral vectors that were used for gene transfer induced potent anti-viral responses in these cells making these vectors inappropriate for gene delivery.

In one aspect, the present disclosure provides innovative methods and compositions that can successfully transfect or transduce a myeloid cell, or otherwise induce a genetic modification in a myeloid cell, with the purpose of augmenting a functional aspect of a myeloid cell, additionally, without compromising the cell's differentiation capability, maturation potential, and/or its plasticity.

In one aspect, myeloid cells appear to be the most abundant cells in a tumor (FIG. 1). Myeloid cells are also capable of recognizing a tumor cell over a healthy normal cell of the body and mount an immune response to a tumor cell of the body. As sentinels of innate immune response, myeloid cells are able to sense non-self or aberrant cell types and clear them via a process called phagocytosis. This can be directed to a therapeutic advantage in driving myeloid cell mediated phagocytosis and lysis of tumor cells. However, these naturally occurring tumor-infiltrating myeloid cells (TIMs) may be subjected to influence of the tumor microenvironment (TME). TIMs constitute a heterogeneous population of cells. Man TIMs originate from circulating monocytes and granulocytes, which in turn stem from bone marrow-derived hematopoietic stem cells. However, in the presence of persistent stimulation by tumor-derived factors the monocyte and granulocyte progenitors divert from their intrinsic pathway of terminal differentiation into mature macrophages, DCs or granulocytes, and may become tumor promoting myeloid cell types. Differentiation into pathological, alternatively activated immature myeloid cells is favored. These immature myeloid cells include tumor-associated DCs (TADCs), tumor-associated neutrophils (TANS), myeloid-derived suppressor cells (MDSCs), and tumor-associated macrophages (TAMs). Alternative to this emergency myelopoiesis, TAMs may also originate from tissue-resident macrophages, which in turn can be of embryonic or monocytic origin. These tissue-resident macrophages undergo changes in phenotype and function during carcinogenesis, and proliferation seems key to maintain TAMS derived from tissue-resident macrophages. In essence a tumor microenvironment may drive a tumor infiltrating myeloid cell to become myeloid derived suppressor cells and acquire the ability to suppress T cells. As a result, innovative methods are necessary to create therapeutically effective TIMs that can infiltrate a tumor, and can target tumor cells for phagocytic uptake and killing.

In one aspect, provided herein are engineered myeloid cells that are potent in infiltrating, targeting, and killing tumor cells. An engineered myeloid/phagocytic cell described herein is designed to comprise a recombinant nucleic acid, which encodes one or more proteins that help target the phagocytic cell to a "target cell," for example a tumor cell or a cancer cell. In one embodiment, the engineered myeloid cell is capable of readily infiltrating a tumor. In one embodiment, the engineered myeloid cell has high specificity for the target cell, with none or negligible cross-reactivity to a non-tumor, non-diseased cell of the subject while in circulation. In one embodiment, the engineered myeloid/phagocytic cell described herein is designed to comprise a recombinant nucleic acid, which will help the cell to overcome/bypass the TME influence and mount a potent anti-tumor response. In one embodiment, the engineered myeloid/phagocytic cell described herein is designed to comprise a recombinant nucleic acid, which augments phagocytosis of the target cell. In another embodiment, the engineered myeloid/phagocytic cell described herein is designed to comprise a recombinant nucleic acid, which augments reduce or eliminate trogocytosis and/or enhance phagocytic lysis or of the target cell.

Accordingly, in some embodiments, the compositions disclosed herein comprises a myeloid cell, comprising a recombinant nucleic acid encoding a chimeric receptor, for example, a phagocytic receptor (PR) fusion protein (PFP). The recombinant nucleic acid has a PR subunit comprising: (i) a transmembrane domain, and (ii) an intracellular domain comprising a PR intracellular signaling domain; and an extracellular antigen binding domain specific to an antigen of a target cell; wherein the transmembrane domain and the extracellular antigen binding domain are operatively linked; wherein the PR intracellular signaling domain is derived from a receptor with a signal transduction domain. The recombinant nucleic acid further encodes for one or more polypeptides that constitute one or more plasma membrane receptors that helps engage the phagocytic cell to the target cell, and enhance its phagocytic activity.

In one embodiment, the myeloid cell described herein comprises one or more recombinant proteins comprising a chimeric receptor, wherein the chimeric receptor is capable of responding to a first phagocytic signal directed to a target cell, which may be a diseased cell, a tumor cell or a pathogen, and a second signal, which is an inflammatory signal, that augments the phagocytic and killing response to target initiated by the first signal.

Phagocytes

Provided herein are methods and compositions for immunotherapy, comprising 'improving' or 'modifying' or 'engineering' a phagocytic cell and targeting it towards a specific target, which can be a specific cell type or class of cells in a patient or a subject. In some embodiments, the subject is a patient having a disease. The terms subject and patient may often be used interchangeably in this section. In some embodiments, the phagocytic cell is derived from the subject having a disease, wherein the disease is, for example, cancer. The autologous cells from the subject may be modified in vitro and administered into the cell, where the modified phagocytic cell is redesigned to specifically attack and kill the cancer cells in the subject.

In some embodiments, the subject has a disease that is not a cancer.

In some embodiments, the subject has a disease that is an infection. In some embodiments, the methods and compositions for immunotherapy provided herein are for 'improving' or 'modifying' or 'engineering' a phagocytic cell and targeting it towards an infection, for example an infected cell within the subject.

In some embodiments, the subject has a disease that is a viral, a bacterial, a fungal or a protozoal infection. In some embodiments, the methods and compositions for immunotherapy provided herein are for 'improving' or 'modifying' or 'engineering' a phagocytic cell and targeting it towards a virus infected cell, a bacteria infected cell, a fungus infected cell or a protozoa infected cell inside the infected subject. In some embodiments the methods and compositions for immunotherapy provided herein are for 'improving' or 'modifying' or 'engineering' a phagocytic cell and targeting it towards a virus, a bacteria, a fungus or any pathogen in a subject, such that the virus, the bacteria, the fungus or the pathogen in a subject is phagocytosed, and/or killed. In some embodiments the methods and compositions for immunotherapy provided herein are for 'improving' or 'modifying' or 'engineering' a phagocytic cell and targeting it towards a viral antigen, a bacterial antigen, a fungal antigen or an antigen of a pathogen in a subject, such that there is at least one improved immune response within the subject to the virus, the bacteria, the fungus or the pathogen in the subject.

In some embodiments, the phagocytic cells are allogeneic. In one embodiment, the methods and compositions for immunotherapy provided herein comprises obtaining phagocytic cells derived from an allogeneic source, the phagocytic cells are thereafter modified or engineered and introduced into a diseased subject, such that the modified or engineered phagocytic cells from the allogeneic source are capable of attacking a diseased cell of the subject, phagocytose the diseased cell and/or kill the diseased cell, or improve at least one immune response of the subject to the disease. In some embodiments, the allogeneic source is a human. In some embodiments, the allogeneic source is a healthy human.

Phagocytes are the natural sentinels of the immune system and form the first line of defense in the body. They engulf a pathogen, a pathogen infected cell a foreign body or a cancerous cell and remove it from the body. Most potential pathogens are rapidly neutralized by this system before they can cause, for example, a noticeable infection. This can involve receptor-mediated uptake through the clathrin coated pit system, pinocytosis, particularly macropinocytosis as a consequence of membrane ruffling and phagocytosis. The phagocytes therefore can be activated by a variety of non-self (and self) elements and exhibit a level of plasticity in recognition of their "targets".

Mononuclear phagocytic system (MPS), comprised of monocytes, macrophages, and dendritic cells, is essential in tissue homeostasis and in determining the balance of an immune response through its role in antigen presentation. The MPS is defined as a cell lineage which originates from bone marrow progenitor cells and gives rise to blood monocytes, tissue macrophages and dendritic cells. Thus, the process of generating a macrophage from the MPS begins with a promonocyte in the BM which undergoes a differentiation process into a monocyte that is ready to enter the systemic circulation. After a short period (<48 h) in the circulation, these newly formed monocytes rapidly infiltrate into peripheral tissues where a majority of them differentiate into macrophages or dendritic cells (DC). Anti-microbe phagocytosis clears and degrades disease-causing microbes, induces pro-inflammatory signaling through cytokine and chemokine secretion, and recruits immune cells to mount an effective inflammatory response. This type of phagocytosis is often referred to as "inflammatory phagocytosis" (or "immunogenic phagocytosis"). However, in some instances, such as with certain persistent infections, anti-inflammatory responses may follow microbial uptake. Anti-microbe phagocytosis is commonly performed by professional phagocytes of the myeloid lineage, such as immature dendritic cells (DCs) and macrophages and by tissue-resident immune cells. Phagocytosis of damaged, apoptotic cells or cell is typically a non-inflammatory (also referred to as a "nonimmunogenic") process. Transformed or malignant cells (self-cells), and cells are phagocytosed and apoptotic cells are removed promptly without causing damage to the surrounding tissues or inducing a pro-inflammatory immune response. This type of apoptotic cell clearance is non-inflammatory and include release of "find me" signals from apoptotic cells to recruit phagocytes to the location of apoptotic cells; accompanied by "eat me" signals exposed on the surface of apoptotic cells are bound by phagocytes via specific receptors; cytoskeletal rearrangement to engulf the apoptotic cell; followed by the ingested apoptotic cell is digested and specific phagocytic responses are elicited (e.g., secretion of anti-inflammatory cytokines).

Phagocytosis, defined as the cellular uptake of particulates (>0.5 m) within a plasma-membrane envelope, is closely relate to and partly overlaps the endocytosis of soluble ligands by fluid-phase macropinocytic and receptor pathways. Variants associated with the uptake of apoptotic cells, also known as efferocytosis, and that of necrotic cells arising from infection and inflammation (necroptosis and pyroptosis). The uptake of exogenous particles (heterophagy) has features in common with autophagy, an endogenous process of sequestration and lysosomal disposal of damaged intracellular organelles There is a spectrum of uptake mechanisms depending on the particle size, multiplicity of receptor-ligand interactions, and involvement of the cytoskeleton. Once internalized, the phagosome vacuole can fuse selectively with primary lysosomes, or the product of the endoplasmic reticulum (ER) and Golgi complex, to form a secondary phagolysosome (Russell, D. G. (2011). Immunol. Rev. 240, 252-268). This pathway is dynamic in that it undergoes fusion and fission with endocytic and secretory vesicles macrophages, DCs, osteoclasts, and eosinophils. Anti-microbe phagocytosis clears and degrades disease-causing microbes, induces pro-inflammatory signaling through cytokine and chemokine secretion, and recruits immune cells to mount an effective inflammatory response. This type of phagocytosis is often referred to as "inflammatory phagocytosis" (or "immunogenic phagocytosis"). However, in some instances, such as with certain persistent infections, anti-inflammatory responses may follow microbial uptake. Anti-microbe phagocytosis is commonly performed by professional phagocytes of the myeloid lineage, such as immature dendritic cells (DCs) and macrophages and by tissue-resident immune cells. Phagocytosis of damaged, self-derived apoptotic cells or cell debris (e.g., efferocytosis), in contrast, is typically a non-inflammatory (also referred to as a "nonimmunogenic") process. Billions of damaged, dying, and unwanted cells undergo apoptosis each day. Unwanted cells include, for example, excess cells generated during development, senescent cells, infected cells (intracellular bacteria or viruses), transformed or malignant cells, and cells irreversibly damaged by cytotoxic agents.

The bone marrow is the source of circulating neutrophils and monocytes that will replace selected tissue-resident macrophages and amplify tissue myeloid populations during inflammation and infection. After phagocytosis, newly recruited monocytes and tissue macrophages secrete their products by generating them from pre-existing phospholipids and arachidonates in the plasma membrane and by releasing radicals generated by activation of a respiratory burst or induction of inducible nitric oxide synthesis; apart from being achieved by synthesis of the low-molecular-weight products (arachidonate metabolites, superoxide anions, and nitric oxide) generated as above, secretion induced by phagocytosis in macrophages is mainly achieved by new synthesis of RNA and changes in pH, resulting in progressive acidification.

In some embodiments, the phagocytes of the invention are monocytes or cells of the monocyte lineage.

In some embodiments, phagocytic macrophages are MARCO+SignR1+ and are found in the outer marginal zone rapidly clear capsulated bacteria. Similar CD169+F4/80− macrophages line the subcapsular sinus in lymph nodes and have been implicated in virus infection. It was noted that endothelial macrophages, including Kupffer cells in the liver, clear microbial and antigenic ligands from blood and lymph nodes to provide a sinusoidal immune function comparable to but distinct from mucosal immunity. Not all tissue macrophages are constitutively phagocytic, even though they still express typical macrophage markers. In the marginal zone of the rodent spleen, metallophilic macrophages, which lack F4/80, strongly express CD169, sialic acid-binding immunoglobulin (Ig)-like lectin 1 (SIGLEC1 [sialoadhesin]), but are poorly phagocytic. Non-professional phagocytes include epithelial cells, and fibroblasts. Fibroblasts are "working-class phagocytes" clear apoptotic debris by using integrins other than CD11b-CD18 through adhesion molecules ICAM and vitronectin receptors. Astrocytes have also been reported to engulf, even if not efficiently degrade, apoptotic corpses. Plasma-membrane receptors relevant to phagocytosis can be opsonic, FcRs (activating or inhibitory) for mainly the conserved domain of IgG antibodies, and complement receptors, such as CR3 for iC3b deposited by classical (IgM or IgG) or alternative lectin pathways of complement activation. CR3 can also mediate recognition in the absence of opsonins, perhaps by depositing macrophage-derived complement. Anti-microbe phagocytosis is commonly performed by professional phagocytes of the myeloid lineage, such as immature dendritic cells (DCs) and macrophages and by tissue-resident immune cells.

In some embodiments, for the purpose of the instant cellular engineering program disclosed herein, cells that are used for engineering for use in immunotherapy are potentially phagocytic.

In some embodiments, for the purpose of the instant cellular engineering program disclosed herein, cells that are used for engineering for use in immunotherapy are potently phagocytic.

In some embodiments, for the purpose of the instant cellular engineering program disclosed herein, cells that are used for engineering for use in immunotherapy are obtained from whole blood, peripheral blood mononuclear cells, bone marrow, lymph node tissue, cord blood, thymus tissue, tissue from a site of infection, ascites, pleural effusion, spleen tissue.

In some embodiments, cells that are used for engineering for use in immunotherapy are obtained from peripheral blood.

Notably, a considerable degree of heterogeneity is observed among phagocytic cells. For example, among the liver MPS, a variety of structural and functional distinctions have been characterized, both stimulatory and inhibitory with respect to the purpose of generation of cells for cancer immunotherapy.

TABLE 1

Exemplary phenotypic characteristics of liver monocytes, macrophages and DCs

| | Molecularly defined | Other characteristics |
| --- | --- | --- |
| Liver monocytes | CD14+ + CD16−<br>CD14+ + CD16+<br>DC-like phenotype -<br>High DR, CD80+<br>Macrophage-like<br>phenotype - CD163+,<br>CD68+<br>CD16+ CD14dim<br>CD14 "DC"-Postulated<br>to be monocyte derived | CD16+ monocytes (undefined as to whether they CD14+ + CD16+ or CD16+ CD14dim) possess superior phagocytosis compared to blood monocytes and can efficiently activate CD4+ T cells |
| Liver macrophages | Pan CD68 | Liver Macrophages appear to be predominantly tolerogenic in nature, with a regulatory and scavenging role |

TABLE 1-continued

Exemplary phenotypic characteristics of liver monocytes, macrophages and DCs

| | Molecularly defined | Other characteristics |
|---|---|---|
| Liver dendritic cells | BDCA1 (CD1c+) DC<br>BDCA2 (CD303+) DC<br>BDCA3 (CD141hi) DC | Tolerogenic in nature; Lower expression of costimulation markers compared to spleen; Produce IL-10 on LPS stimulation; Stimulate T-cells that are IL-10 producing and hypo-responsive on re-stimulation; Produce higher numbers of FoxP3+ Treg cells on naïve T cell stimulation; Weak MLR response compared to blood. |

In some embodiments the phagocytic cells that are engineered for use in immunotherapy in the instant application comprise phagocytic cell selected from the group consisting of macrophages, dendritic cells, mast cells, monocytes, neutrophils, microglia, and astrocytes.

In some embodiments the phagocytic cells that are engineered for use in immunotherapy are myeloid cells. In some embodiments, the phagocytic cells are monocytes.

In some embodiments, the phagocytic cells that are engineered for use in immunotherapy in the instant application are monocytes, monocyte derived macrophages, and/or dendritic cells.

In some embodiments the phagocytic cells that are engineered for use in immunotherapy in the instant application are monocytes or macrophages.

In some embodiments the cells that are macrophages or myeloid cells obtained from the peripheral blood.

In some embodiments, the macrophages or myeloid cells are selected by selection marker $CD14^+CD16^{low}$.

In some embodiments, the macrophages or myeloid cells are isolated from leukapheresis column of the subject. In some embodiments the subject is the same subject who is administered the pharmaceutical composition comprising engineered cells.

In some embodiments the subject is not the same subject who is administered the pharmaceutical composition comprising engineered cells.

In some embodiments, the leukapheresis is performed on the same subject once a week to collect more macrophages or myeloid cells. In some embodiments, the leukapheresis is performed on the same subject more than once in a span of 8-10 days to collect more macrophages. In some embodiments, the leukapheresis is performed on the same subject more than twice in a span of one months to collect more macrophages.

In some embodiments, myeloid cells are isolated from a leukapheresis sample or a peripheral blood sample. In some embodiments, the myeloid cell is a progenitor cell. In some embodiments, the myeloid cell is a monocyte precursor cell. In some embodiments, a myeloid cell described herein is not differentiated into a terminal cell and do not exhibit a terminal cell phenotype, such as tissue macrophages. In some embodiments, the myeloid cells comprise CD14+ cells. In some embodiments, the myeloid cells do not express CD16. In some embodiments the myeloid cells express low amounts of CD16. In some embodiments, the myeloid cells are pre-selected for the purpose of engineering from a biological sample, such as peripheral blood or an apheresis sample by selection of CD14+ cells. In some embodiments, the selection is performed without contacting with or engaging with the myeloid cell to be selected. In some embodiments, the myeloid cells are selected prior to engineering from a biological sample by sorting, for example a flow cytometry based cell sorter (FACS). In some embodiments, the myeloid cells expressing CD16 are captured by an antibody and the remaining myeloid cells were collected and used for engineering. In some embodiments, one or more other cell surface molecules are targeted for capturing in the negative selection process in addition to CD16, in order to obtain the myeloid cells, for example CD3, CD8, CD11c, CD40, or CD206.

In one aspect, provided herein are myeloid cells, comprising at least one exogenous recombinant nucleic acid that encodes for a fusion protein, the fusion protein is a chimeric protein, and the fusion protein comprises at least a transmembrane domain and an extracellular domain that comprises a region that can bind to a target cell. In some embodiments, the target cell is a cancer cell, and the extracellular domain that comprises a region that can bind to a target on a cancer cell. A target is a cancer antigen. When the chimeric protein is expressed in the myeloid cell, it activates the myeloid cell to overcome TME induced suppressive signal and act as an activated pro-inflammatory myeloid cell. In one embodiment, the chimeric protein that is expressed in the myeloid cell is capable of being responsive to a second signal other than the target (the first signal), wherein the second signal is a pro-inflammatory signal and an activating signal.

In another embodiment, the chimeric protein that is expressed in the myeloid cell is specific for binding to a target. In some embodiments, the target is a cancer antigen. Expression of the chimeric protein endows target specificity to the myeloid cell.

In one embodiment, the chimeric protein that is expressed in the myeloid cell is capable of multiplexing, for example, has multiple domains for activation and processing of more than one signal or signal types. In some embodiments, activation of the multiple domains simultaneously lead to an augmented effector response to the myeloid cell. An effector response for the myeloid cell encompasses, for example, enhanced phagocytosis, pro-inflammatory activation, and killing of target cell. In some embodiments, the chimeric protein that is expressed in the myeloid cell, capable of multiplexing is capable of binding to more than one ligands, such as a target antigen and a helper molecule. In some embodiments, the chimeric protein is capable of binding to multiple target antigens on a cancer cell. In some embodiments, the chimeric protein is capable of multiplexing is capable of binding to multiple target antigens on multiple cells. In some embodiments, the chimeric protein may bind to an macrophage-monocyte inhibitory target on a cancer cell, and create a stimulatory signal upon contact using the pro-inflammatory domain fused to the intracellular end, a process termed as "signal switch". For example, an extracellular domain of the chimeric protein may comprise a CD47-binding domain, whereas, the chimeric fusion protein lacks the transmembrane and/or intracellular domain of the native CD47 receptor, but comprises a PI3K recruiter domain at the intracellular region, thereby converting the macrophage-monocyte inhibitory signal from contact with the tumor cell to a pro-inflammatory phagocytosis enhancing signal.

In some embodiments, the chimeric protein is capable multiplexing is capable of binding to multiple units of the expressed chimeric protein, for example, multimerizing. Multimerizing comprises dimer, trimer, tetramer, pentamer, hexamer, heptamer, octamer, nonamer, or decamer formations. In some embodiments, multimerizing can occur via association of the transmembrane region, the extracellular region or the intracellular region or combinations thereof. For example, a chimeric protein comprising a region of the collagenous domain of the phagocytic receptor MARCO may form a trimer for its effective function. In some embodiments, the chimeric protein is capable of associating with other molecules for example, another receptor. For example, the chimeric protein comprises an Fc-alpha transmembrane domain that dimerizes with Fc-gamma TM domain, wherein the Fc-gamma may be an endogenous receptor.

In some embodiments, chimeric protein is capable multiplexing comprises multiple intracellular domains that can be activated by more than one signal and can in turn activate multiple intracellular signaling molecules. For example, the chimeric protein may comprise, a phagocytosis receptor domain and a pro-inflammatory domain. For example, the chimeric protein comprises a FcR signaling domain and an additional phosphorylation domain that recruits pro-caspases.

Phagocytic Receptor (PR) Subunit of PFP Fusion Protein

Provided herein is recombinant nucleic acid encoding a phagocytic receptor (PSR) fusion protein (PFP). The PFP comprises a PSR subunit comprising: a transmembrane (TM) domain, and an intracellular domain (ICD) comprising a PR intracellular signaling domain. In some embodiments, the recombinant nucleic acid encoding the PFP when expressed in a cell, the PFP functionally incorporates into the cell membrane of the cell. In some embodiments, the recombinant nucleic acid encodes for a transmembrane domain that specifically incorporates in the membrane of a phagocytic cell, e.g., a macrophage.

In some embodiments, the suitable PR is selected after screening a library of membrane spanning proteins. The PR subunit is fused at the extracellular domain with a cancer cell binding antibody. In some embodiments, the PR may be fused with one or more additional domains at the intracellular end.

Intracellular Domain of PFP Fusion Protein

In some embodiments the PSP subunit comprises a TM domain of a phagocytic receptor.

In some embodiments the PSP subunit comprises an ICD domain of a phagocytic receptor.

In some embodiments, the phagocytic receptor is a scavenger receptor. Whilst many scavenger receptors collaborate in the detection and ingestion of materials, not all the receptors engaged in the course of phagocytosis trigger engulfment alone. The engagement of certain phagocytosis and scavenger receptors can have dramatic impacts on the downstream immune response. For example, triggering the type A scavenger receptor MARCO with 500 nm negatively charge nanoparticles is associated with an anti-inflammatory tolerogenic immune response. Whereas, particles with positive charge are engulfed by a subset of phagocytosis receptors that activate proinflammatory pathways such as NLRP3 and/or fibrotic responses. Furthermore, certain scavenger receptor pathways such as the scavenger receptor expressed by endothelial cells (SREC-I), have been shown to play a role in antigen cross presentation. Therefore, identifying and understanding potential receptors that can be harnessed to enhance macrophage activity and clinical efficacy is important step in the PFP development platform.

Non-opsonic receptors variably expressed naturally by professional phagocytes include lectin-like recognition molecules, such as CD169, CD33, and related receptors for sialylated residues. In addition, phagocytes also express Dectin-1 (a receptor for fungal beta-glucan with well-defined signaling capacity), related C-type lectins (e.g., MICL, Dectin-2, Mincle, and DNGR-1), and a group of scavenger receptors. SR-A, MARCO, and CD36 vary in domain structure and have distinct though overlapping recognition of apoptotic and microbial ligands. CD36-related family member revealed that apoprotein ligands bind to receptor helical bundles, whereas their exofacial domains form a channel through which lipids such as cholesterol are translocated to the membrane bilayer. Notably, toll-like receptors (TLRs) are sensors and not phagocytic entry receptors, although they often collaborate with other non-opsonic receptors to promote uptake and signaling.

TABLE 2

Scavenger receptors in human

| Gene names, aliases | NCBI Acc # |
|---|---|
| MSR1, SR-AI,, CD204, SCARA1, SR-A1 | NM_138715 |
| Alternatively spliced form of SR-AI SR-AII SR-A1.1 | NM_002445 |
| MARCO, SCARA2, SR-A6 | NM_006770 |
| SCARA3, MSRL1, SR-A3 | NM_016240 |
| COLEC12, SCARA4, SRCLI, SRCLII, CL-P1, SR-A4 | NM_130386 |
| SCARA5, TESR, NET33 SR-A5 | NM_173833 |
| CD36 SCARB3, FAT, GPIV, PAS4 SR-B2 | NM_001001548 |
| SCARB1 SR-BI, CD36L1 SR-B1 | NM_005505 |
| CD68 gp110, SCARD1, LAMP4 SR-D1 | NM_001251 |
| OLR1 LOX-1, SCARE1, CLEC8A SR-E1 | NM_002543 |
| Alternatively spliced form of SRE-1 LOXIN SR-E1.1 | NM_001172632 |
| CLEC7A, Dectin-1, SCARE2, CD369, SR-E2 | NM_197947 |
| CD206/MRC1, Mannose receptor 1 SR-E3 | NM_002438 |
| ASGPR ASGR1, CLEC4H1, HL-1 SR-E4 | NM_001197216 |
| SCARF1, SREC-I, SR-F1 | NM_003693 |
| MEGF10, EMARDD, SR-F2 | NM_032446 |
| CXCL16, SR-PSOX SR-G1 | NM_001100812 |
| STAB1, FEEL-1, SR-H1 | NM_015136 |
| STAB2, FEEL-2, SR-H2 | NM_017564 |
| CD163 M130, CD163A, SR-I1 | NM_004244 |
| CD163L1 CD163B, M160 SR-I2 | NM_001297650 |
| SCART1 CD163c-a SR-I3 | NR_002934.3 |
| RAGE (membrane form) AGER SR-J1 | NM_001136 |
| RAGE (soluble form) AGER SR-J1.1 | AB061668 |
| CD44 Pgp-1 SR-K1 | NM_000610 |
| LRP1 A2MR, APOER, CD91 SR-L1 | NM_002332 |
| LRP2 Megalin, gp330 SR-L2 | NM_004525 |
| SRCRB4D | NM_080744 |
| SSC5D | NM_001144950 |
| CD14 | NM_000591 |
| Ly75/CD205 | NM_002349 |
| CD207/Langerin | NM_015717 |
| CD209/DC-SIGN CLEC4L | NM_021155 |

TABLE 3

Selected ligands of SR family members

| SR molecules | Ligands |
| --- | --- |
| SR-AI/II | Undefined protein in serum, Activated B cells, β amyloid protein, Apoptotic cells AGE-modified proteins Ox-LDL, Ac-LDL, LPS, LTA, $G^+$ and $G^-$ bacteria |
| MARCO | Splenic B cells UGRP-1 in lung clara cells, Ox-LDL, Ac-LDL, $G^+$ and $G^-$ bacteria |
| SRCL-I/II | T and Tn antigen, Ox-LDL, $G^+$ and $G^-$ bacteria, yeast |
| LOX-1 | Fibronectin, AGE-modified protein, Apoptotic cells, Ox-LDL, $G^+$ and $G^-$ bacteria |
| SR-PSOX | Chemokine receptor, Phosphatidyl serine CXCR6, $G^+$ and $G^-$ bacteria, Apoptotic cells, Ox-LDL |
| FEEL-I/II | AGE- modified protein, Ac-LDL, $G^+$ and $G^-$ bacteria |
| dSR-CI | Ac-LDL, $G^+$ and $G^-$ bacteria, glucan, laminarin |
| CD-36 | Thrombospondin, Collagen, AGE, Apoptotic cells, Ox-LDL, PfEMP protein on plasmodium infected RBC Diacylated lipids on bacteria |
| SR-BI | AGE-modified proteins, Apoptotic cells Ox-LDL |
| CLA-I/human SR-BI | Apoptotic cells, Ox-LDL, LPS, Hepatitis C virus E2 glycoprotein |
| gp-340 | Surfactant protein-A, surfactant protein-D, $G^+$ and $G^-$ bacteria Influenza A virus, gp-120 |

(ND, not defined)

In some embodiments, the recombinant nucleic acid encodes a chimeric antigenic receptor for phagocytosis (CAR-P). The CARP described herein is a phagocytic scavenger receptor (PSR) fusion protein (PFP). PSP comprising an ICD and/or a TM derived from a phagocytic receptor.

In some embodiments, the ICD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor.

In some embodiments, the ICD comprises the signaling domain derived from any one or more of: lectin, dectin 1, mannose receptor (CD206), scavenger receptor A1 (SRA1), MARCO (Macrophage Receptor with Collagenous Structure, aliases: SRA6, SCARA2), CD36 (Thrombospondin receptor, aliases: Scavenger Receptor class B, member 3), CD163 (Scavenger receptor, cysteine rich-type 1), MSR1, SCARA3, COLEC12 (aliases: Scavenger Receptor With C-Type Lectin, SCARA4, or Collectin 12), SCARA5, SCARB1, SCARB2, CD68 (SCARD, microsialin), OLR1 (Oxidized Low Density Lipoprotein Receptor 1, LOX1, or C-Type Lectin Domain Family 8 Member A), SCARF1, SCARF2, SRCRB4D, SSC5D, and CD169 (aliases, Sialoadhesin receptor, SIGLEC1).

In some embodiments, the recombinant nucleic acid encodes, for example, an intracellular domain of human MARCO. The PSR subunit comprises an intracellular domain having a 44 amino acid ICD of human MARCO having an amino acid sequence: MRNKKILKEDELL-SETQQAAFHQIAMEPFEINVPKPKRRNGVNF (SEQ ID NO: 24). In some embodiments the PSR subunit comprises a variant which is at least 70%, 75%, 80%, 85%, 90% or 95% identical to the intracellular domain of MARCO.

In some embodiments, for example, the PSR comprises a transmembrane region of human MARCO.

In some embodiments, the recombinant nucleic acid encodes an intracellular domain of human SRA1. The PSR subunit comprises an intracellular domain having a 50 amino acid ICD of human SRA1 having an amino acid sequence: MEQWDHFHNQQEDTDSCSESVKF-DARSMTA LLPPNPKNSPSLQEKLKSFK (SEQ ID NO: 25). In some embodiments the PSR subunit comprises a variant which is at least 70%, 75%, 80%, 85%, 90% or 95% identical to the intracellular domain of human SRA1. The intracellular region of SRA has a phosphorylation site.

In some embodiments, the PSR comprises a transmembrane region of human SRA1.

In some embodiments, for example, the recombinant nucleic acid comprises an intracellular domain of CD36. In some embodiments, the recombinant nucleic acid comprises a TM domain of CD36. Naturally occurring full length CD36 has two TM domains and two short intracellular domains, and an extracellular domain of CD36 binds to oxidized LDL. Both of the intracellular domains contain pairs of cysteines that are fatty acid acylated. It lacks known signaling domains (e.g. kinase, phosphatase, g-protein binding, or scaffolding domains). N-terminal cytoplasmic domain is extremely short (5-7 amino acid residues) and is closely associated with the internal leaflet of the plasma membrane. The carboxy-terminal domain contains 13 amino acids, containing a CXCXSK motif homologous to a region in the intracellular domain of CD4 and CD8 that is known to interact with signaling molecules. The intracellular domain of CD36 is capable of assembling a signaling complex that activates lyn kinases, MAP kinases and Focal Adhesion Kinases (FAK), and inactivation of src homology 2-containing phosphotyrosine phosphatase (SHP-2). Members of the guanine nucleotide exchange factors (GEFs) have been identified as potential key signaling intermediates.

In some embodiments, the recombinant nucleic acid encodes for example, an intracellular domain of human SCARA3. The PSR subunit comprises an intracellular domain having a 56 amino acid ICD of human SCARA3 having an amino acid sequence: MKVRSAGGDGDALCV-TEEDL AGDDEDMPTFPCTQKGRPGPRCSRCQKNLS LHTSVR (SEQ ID NO: 26). In some embodiments the PSR subunit comprises a variant which is at least 70%, 75%, 80%, 85%, 90% or 95% identical to the intracellular domain of human SCARA3. In some embodiments the PSR comprises the TM domain of SCARA3.

In some embodiments, the TM domains are about 20-30 amino acids long. TM domains of SRs are about 20-30 amino acids long.

Scavenger receptors may occur as homo or hetero dimers. MARCO, for example occurs as a homo trimer.

In some embodiments, the TM domain or the ICD domain of the PSP is not derived from FcR, Megf10, Bai1 or MerTK. In some embodiments, the ICD of the PSR does not comprise a CD3 zeta intracellular domain.

In some embodiments, the intracellular domain and transmembrane domains are derived from FcR beta.

In one aspect the recombinant nucleic acid encodes a chimeric antigenic receptor for enhanced phagocytosis (CAR-P), which is a phagocytic scavenger receptor (PSR) fusion protein (PFP) comprising: (a) an extracellular domain comprising an extracellular antigen binding domain specific to an antigen of a target cell, (b) a transmembrane domain, and (c) a recombinant PSR intracellular signaling domain, wherein the recombinant PSR intracellular signaling domain comprises a first portion derived from a phagocytic and a second portion derived from non-phagocytic receptor.

In some embodiments, the second portion is not a PI3K recruitment domain.

The second portion derived from non-phagocytic receptor may comprise an intracellular signaling domain that enhances phagocytosis, and/or inflammatory potential of the engineered phagocytic cells expressing the recombinant nucleic acid. In some embodiment, the second portion derived from non-phagocytic receptor comprises more than one intracellular domains (ICD). In some embodiments, the second portion derived from non-phagocytic receptor comprises a second ICD. In some embodiments, the second portion derived from non-phagocytic receptor comprises a second and a third ICD. In some embodiments, the second portion derived from non-phagocytic receptor comprises a second, a third and a fourth ICD, wherein the second portion is encoded by the recombinant nucleic acid. The respective second portions comprising a second, or third or fourth ICD derived from non-phagocytic receptor are described as follows.

Chimeric Antigen Receptors for Enhancing Intracellular Signaling and Inflammation Activation In one aspect, the recombinant nucleic acid encodes a second intracellular domain in addition to the phagocytic ICD, which confers capability of potent pro-inflammatory immune activation, such as when macrophages engage in fighting infection. The second intracellular domain (second ICD) is fused to the cytoplasmic terminus of the first phagocytic ICD. The second intracellular domain provides a second signal is necessary to trigger inflammasomes and pro-inflammatory signals. Nod-like receptors (NLRs) are a subset of receptors that are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2.

The tumor microenvironment (TME) constitutes an immunosuppressive environment. Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the phagocytic receptor (PR) fusion protein (PFP) comprising the cytoplasmic domain for inflammatory response in the engineered macrophages confers potent pro-inflammatory response similar to the M1 phenotype.

In some embodiments, the cytoplasmic domain for inflammatory response can comprise an intracellular signaling domain of TLR3, TLR4, TLR9, MYD88, TRIF, RIG-1, MDA5, CD40, IFN receptor, NLRP-1, NLRP-2, NLRP-3, NLRP-4, NLRP-5, NLRP-6, NLRP-7, NLRP-8, NLRP-9, NLRP-10, NLRP-11, NLRP-12, NLRP-13, NLRP-14, NOD1, NOD2, Pyrin, AIM2, NLRC4 and/or CD40.

In some embodiments, the expression of the recombinant nucleic acid encoding the phagocytic scavenger receptor (PSR) fusion protein (PFP) comprises a pro-inflammatory cytoplasmic domain for activation of IL-1 signaling cascade.

In some embodiments, the cytoplasmic portion of the chimeric receptor (for example, phagocytic receptor (PR) fusion protein (PFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9).

In some embodiments, the cytoplasmic portion of the chimeric receptor comprises a suitable region from interleukin-1 receptor-associated kinase 1 (IRAK1).

In some embodiments, the cytoplasmic portion of the chimeric receptor comprises a suitable region from differentiation primary response protein (MYD88).

In some embodiments, the cytoplasmic portion of the chimeric receptor comprises a suitable region from myelin and lymphocyte protein (MAL).

In some embodiments, the cytoplasmic portion of the chimeric receptor comprises a suitable region from retinoic acid inducible gene (RIG-1).

In some embodiments the transmembrane domain of the PSR comprises the transmembrane domain of any one of MYD88, TLR3, TLR4, TLR7, TLR8, TLR9, MAL, IRAK1, proteins.

In some embodiments, the recombinant PSR intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the PFP in addition to the first cytoplasmic portion.

In some embodiments, the phosphorylation is a Tyrosine phosphorylation.

In some embodiments the second intracellular domain is an Immune receptor Tyrosine Activation Motif (ITAM). The ITAM motif is present in mammalian a and β immunoglobulin proteins, TCR γ receptors, FCR γ receptors subunits, CD3 chains receptors and NFAT activation molecule.

In some embodiments the PFP intracellular domain comprises one ITAM motif. In some embodiments the PFP intracellular domain comprises more than one ITAM motifs. In some embodiments the PFP intracellular domain comprises two or more ITAM motifs. In some embodiments the PFP intracellular domain comprises three or more ITAM motifs. In some embodiments the PFP intracellular domain comprises four or more ITAM motifs. In some embodiments the PFP intracellular domain comprises five or more ITAM motifs. In some embodiments the PFP intracellular domain comprises six or more ITAM motifs. In some embodiments the PFP intracellular domain comprises seven or more ITAM motifs. In some embodiments the PFP intracellular domain comprises eight or more ITAM motifs. In some embodiments the PFP intracellular domain comprises nine or more ITAM motifs. In some embodiments the PFP intracellular domain comprises ten or more ITAM motifs.

In some embodiments one or more domains in the first phagocytic ICD comprises a mutation.

In some embodiments one or more domains in the second ICD comprises a mutation to enhance a kinase binding domain, to generate a phosphorylation site, to generate an SH2 docking site or a combination thereof.

Co-Expression of an Inflammatory Gene

In one aspect, the recombinant nucleic acid comprises a coding sequence for a pro-inflammatory gene, which is co-expressed with the PFP in the engineered cell. In some embodiments, the pro-inflammatory gene is a cytokine. Examples include but not limited to TNF-□, IL-1α, IL-1β, IL-6, CSF, GMCSF, or IL-12 or interferons.

The recombinant nucleic acid encoding the proinflammatory gene can be monocistronic, wherein the two coding sequences for (a) the PSP and (b) the proinflammatory gene are post-transcriptionally or post-translationally cleaved for independent expression.

In some embodiments, the two coding sequences comprise a self-cleavage domain, encoding a P2A sequence, for example.

In some embodiments the two coding regions are separated by a IRES site.

In some embodiments the two coding sequences are encoded by a bicistronic genetic element. The coding regions for (a) the PSP and (b) the proinflammatory gene can be unidirectional, where each is under a separate regulatory control. In some embodiments the coding regions for both are bidirectional and drive in opposite directions. Each coding sequence is under a separate regulatory control.

Coexpression of the proinflammatory gene is designed to confer strong inflammatory stimulation of the macrophage and activate the surrounding tissue for inflammation.

Integrin Activation Domains

Cell-cell and cell-substratum adhesion is mediated by the binding of integrin extracellular domains to diverse protein ligands; however, cellular control of these adhesive interactions and their translation into dynamic cellular responses, such as cell spreading or migration, requires the integrin cytoplasmic tails. These short tails bind to intracellular ligands that connect the receptors to signaling pathways and cytoskeletal networks (Calderwood DA, 2004, Integrin Activation, Journal of Cell Science 117, 657-666). Integrins are heterodimeric adhesion receptors formed by the non-covalent association of α and β subunits. Each subunit is a type I transmembrane glycoprotein that has relatively large extracellular domains and, with the exception of the β4 subunit, a short cytoplasmic tail. Individual integrin family members have the ability to recognize multiple ligands. Integrins can bind to a large number of extracellular matrix proteins (bone matrix proteins, collagens, fibronectins, fibrinogen, laminins, thrombospondins, vitronectin, and von Willebrand factor), reflecting the primary function of integrins in cell adhesion to extracellular matrices. Many "counter-receptors" are ligands, reflecting the role of integrins in mediating cell-cell interactions. Integrins undergo conformational changes to increase ligand affinity.

The Integrin $β_2$ subfamily consists of four different integrin receptors, $α_Mβ_2$ (CD11b/CD18, Mac-1, CR3, Mo-1), $α_Lβ_2$ (CD11a/CD18, LFA-1), $α_Xβ_2$ (CD11c/CD18), and $α_Dβ_2$ (CD11d/CD18). These leukocyte integrins are involved in virtually every aspect of leukocyte function, including the immune response, adhesion to and transmigration through the endothelium, phagocytosis of pathogens, and leukocyte activation.

The a subunits of all 132 integrins contain an inserted region of −200 amino acids, termed the I or A domain. Highly conserved I domains are found in several other integrin a subunits and other proteins, such as certain coagulation and complement proteins. I domains mediate protein-protein interactions, and in integrins, they are integrally involved in the binding of protein ligands. Although the I domains dominate the ligand binding functions of their integrins, other regions of the a subunits do influence ligand recognition. As examples, in $α_Mβ_2$ a mAb (OKM1) recognizing an epitope outside the I domain but in the am subunit inhibits ligand binding; and the EF-hand regions in $α_Lβ_2$ and $α_2β_1$, integrins with I domains in their a subunits, contribute to ligand recognition. The am subunit, and perhaps other a subunits, contains a lectin-like domain, which is involved in engagement of non-protein ligands, and occupancy may modulate the function of the I domain.

As integrins lack enzymatic activity, signaling is instead induced by the assembly of signaling complexes on the cytoplasmic face of the plasma membrane. Formation of these complexes is achieved in two ways; first, by receptor clustering, which increases the avidity of molecular interactions thereby increasing the on-rate of binding of effector molecules, and second, by induction of conformational changes in receptors that creates or exposes effector binding sites. Within the ECM, integrins have the ability to bind fibronectin, laminins, collagens, tenascin, vitronectin and thrombospondin. Clusters of integrin/ECM interactions form focal adhesions, concentrating cytoskeletal components and signaling molecules within the cell. The cytoplasmic tail of integrins serve as a binding site for α-actinin and talin which then recruit vinculin, a protein involved in anchoring F-actin to the membrane. Talin is activated by kinases such as protein kinase C (PKCα).

Integrins are activated by selectins. Leucocytes express L-selectin, activated platelets express P-selectin, and activated endothelial cells express E- and P-selectin. P-selectin-mediated adhesion enables chemokine- or platelet-activating factor-triggered activation of β2 integrins, which stabilizes adhesion. It also facilitates release of chemokines from adherent leucocytes. The cytoplasmic domain of P-selectin glycoprotein ligand I formed a constitutive complex with Nef-associated factor I. After binding of P-selectin, Src kinases phosphorylated Nef-associated factor I, which recruit the phosphoinositide-3-OH kinase p85-p110δ heterodimer and result in activation of leukocyte integrins. E-selectin ligands transduce signals that also affect β2 integrin function. Selectins trigger activation of Src family kinases. SFKs activated by selectin engagement phosphorylate the immunoreceptor tyrosine-based activation motifs (ITAMs) in the cytoplasmic domains of DAP12 and FcRγ. In some respects, CD44 is sufficient to transduce signals from E-selectin. CD44 triggers the inside-out signaling of integrins. A final common step in integrin activation is binding of talin to the cytoplasmic tail of the β subunit. Kindlins, another group of cytoplasmic adaptors, bind to a different region of integrin β tails. Kindlins increase the clustering of talin-activated integrins. Kindlins are responsive to selectin signaling, however, kindlins are found mostly in hematopoietic cells, such as neutrophils. Selectin signaling as well as signaling upon integrin activation by chemokines components have shared components, including SFKs, Syk, and SLP-76.

In some embodiments, the intracellular domain of the recombinant PSR fusion protein comprises an integrin activation domain. The integrin activation domain comprises an intracellular domain of a selectin, for example, a P-selectin, L-selectin or E-selectin.

In some embodiments, the intracellular domain of the recombinant PSR fusion protein comprises an integrin activation domain of laminin.

In some embodiments, the intracellular domain of the recombinant PSR fusion protein comprises an integrin activation domain for activation of Talin.

In some embodiments, the intracellular domain of the recombinant PSR fusion protein comprises an integrin activation domain fused to the cytoplasmic end of the phagocytic receptor ICD domain.

Chimeric Receptor for Enhancing Antigen Cross presentation

In some embodiments, the recombinant nucleic acid encodes a domain capable of enabling cross presentation of antigens. In general, MHC class I molecules present self- or pathogen-derived antigens that are synthesized within the cell, whereas exogenous antigens derived via endocytic uptake are loaded onto MHC class II molecules for presentation to CD4+ T cells. MHC I-restricted presentation of endogenous antigens, in which peptides are generated by the proteasome. However, in some cases, DC can process exogenous antigens into the MHC-I pathway for presentation to CD8+ T cells. This is referred to as cross presentation of antigens. Soluble or exogenous antigenic components may get degraded by lysosomal proteases in the vacuoles and cross presented by DCs, instead of following the endocytic pathway. In some instances, chaperones, such as heat shock protein 90 (Hsp90) have shown to help cross present antigens by certain APCs. HSP-peptide complexes are known to be internalized by a distinct group of receptors compared to free polypeptides. These receptors were from the scavenger receptor families and included LOX-1, SREC-I/SCARF-I, and FEEL1/Stabilin-1. Both SREC-I and LOX-1 have been shown to mediate the cross presentation of molecular chaperone bound antigens and lead to activation of CD8+ T lymphocytes.

SREC-1 (scavenger receptor expressed by endothelial cells) has no significant homology to other types of scavenger receptors but has unique domain structures. It contains 10 repeats of EGF-like cysteine-rich motifs in the extracellular domain. Recently, the structure of SREC-I was shown to be similar to that of a transmembrane protein with 16 EGF-like repeats encoded by the *Caenorhabditis elegans* gene ced-I, which functions as a cell surface phagocytic receptor that recognizes apoptotic cells.

Cross presentation of cancer antigens through the Class-1 MHC pathway results in enhanced CD8+ T cell response, which is associated with cytotoxicity and therefore beneficial in tumor regression. In some embodiments, the intracellular domain of the PFP comprises a SREC1 intracellular domain. In some embodiments, the intracellular domain of the PFP comprises a SRECII intracellular domain.

In some embodiments, the PSR subunit comprises: an intracellular domain comprising a PSR intracellular signaling domain from SREC1 or SRECII.

In some embodiments, the PSR subunit comprises: (i) a transmembrane domain, and (ii) an intracellular domain comprising a PSR intracellular signaling domain from SREC1 or SRECII.

In some embodiments, the PSR subunit comprises: (i) a transmembrane domain, (ii) an intracellular domain comprising a PSR intracellular signaling domain, and (iii) an extracellular domain from SREC1 or SRECII.

Transmembrane Domain of PFP Fusion Protein

In some embodiments, the TM encoded by the recombinant nucleic acid comprises a domain of a scavenger receptor (SR). In some embodiments, the TM can be the TM domain of or derived from any one or more of lectin, dectin 1, mannose receptor (CD206), SRA1, MARCO, CD36, CD163, MSR1, SCARA3, COLEC12, SCARA5, SCARB1, SCARB2, CD68, OLR1, SCARF1, SCARF2, SRCRB4D, SSC5D, and CD169.

In some embodiments, the TM domains are about 20-30 amino acids long. TM domains of SRs are about 20-30 amino acids long.

The TM domain or the ICD domain of the PSP is not derived from Megf10, Bai1 or MerTK. The ICD of the PSR does not comprise a CD3 zeta intracellular domain.

In some embodiments the TM is derived from the same phagocytic receptor as the ICD.

In some embodiments, the TM region is derived from a plasma membrane protein. The TM can be selected from an Fc receptor (FcR). In some embodiments, nucleic acid sequence encoding domains from specific FcRs are used for cell-specific expression of a recombinant construct. An FCR-alpha region comprising the TM domain may be used for macrophage specific expression of the construct. FcRα recombinant protein expresses in mast cells.

In some embodiments, the PFP comprises the TM of an FCR-beta (FcRβ).

In some embodiments, the PFP comprises both the FcRβ and ICD domains. In some embodiments, the PFP comprises both the FcRα and ICD domains.

In some embodiments, the TM domain is derived from CD8.

In some embodiments, the TM is derived from CD2.

In some embodiments the TM is derived from FCR alpha.

Extracellular Domain of PFP Fusion Protein

The extracellular domain comprises an antigen binding domain that binds to one or more target antigens on a target cell. The target binding domain is specific for the target. The extracellular domain can include an antibody or an antigen-binding domain selected from intrabodies, peptibodies, nanobodies, single domain antibodies. SMIPs, and multispecific antibodies.

An antibody fragment comprises a portion of an intact antibody, such as the antigen binding or variable region of the intact antibody. In a further aspect of the invention, an anti-HIV antibody according to any of the above embodiments is a monoclonal antibody, including a chimeric, humanized or human antibody. Antibody fragments include, but are not limited to, Fab, Fab', Fab'-SH, F(ab')$_2$, Fv, diabody, linear antibodies, multispecific formed from antibody fragments antibodies and scFv fragments, and other fragments described below. In another embodiment, the antibody is a full length antibody, e.g., an intact IgG1 antibody or other antibody class or isotype as described herein. (See, e.g., Hudson et al. Nat. Med. 9:129-134 (2003); Pluckthiin, The Pharmacology of Monoclonal Antibodies, vol. 113, pp. 269-315 (1994); Hollinger et al., Proc. Natl. Acad. Sci. USA 90: 6444-6448 (1993); WO93/01161; and U.S. Pat. Nos. 5,571,894, 5,869,046, 6,248,516, and 5,587, 458). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., *E. coli* or phage), as described herein.

An Fv is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

A single-chain Fv (sFv or scFv) is an antibody fragment that comprises the $V_H$ and $V_L$ antibody domains connected into a single polypeptide chain. The sFv polypeptide can further comprise a polypeptide linker between the VH and VL domains that enables the sFv to form the desired structure for antigen binding. (See, e.g., Pluckthun in The Pharmacology of Monoclonal Antibodies, vol. 113, Rosenburg and Moore eds., Springer-Verlag, New York, pp. 269-315 (1994); Borrebaeck 1995, infra. The sFv can be used in a chimeric antigen receptor (CAR).

A diabody is a small antibody fragment prepared by constructing an sFv fragment with a short linker (about 5-10 residues) between the VH and VL domains such that interchain but not intra-chain pairing of the V domains is achieved, resulting in a bivalent fragment. Bispecific diabodies are heterodimers of two crossover sFv fragments in which the $V_H$ and $V_L$ domains of the two antibodies are present on different polypeptide chains. (See, e.g., EP 404, 097; WO 93/11161; and Hollinger et al, Proc. Natl. Acad. Sci. USA, 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability can be formatted into larger molecules to create drugs with prolonged serum half-lives or other pharmacological activities. (See, e.g., WO9425591 and US20030130496).

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. The antibody fragment also can be a "linear antibody. (See, e.g., U.S. Pat. No. 5,641,870). Such linear antibody fragments can be monospecific or bispecific.

In some embodiments, the extracellular domain includes a Fab binding domain. In yet other such embodiments, the extracellular domain includes a scFv.

In some embodiments the chimeric antigen receptor comprises an extracellular antigen binding domain is derived from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the antigens are cancer antigens, and the target cell is a target cancer cell. In some embodiments, the antigen for a target cancer cell is selected from the group consisting of CD3, CD4, CD5, CD7, CD19, CCR2, CCR4, CD30, CD37, TCRB1/2, TCR αβ, TCRγδ. CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-11Ra, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRCSD, CD97, CD179a, ALK, and IGLL1.

Various cancer antigen targets can be selected from cancer antigens known to one of skill in the art. Depending on the cancer and the cell type involved cancer antigens are mutated native proteins. The antigen binding domains are screened for specificity towards mutated/cancer antigens and not the native antigens.

In some embodiments, for example, the cancer antigen for a target cancer cell can be one or more of the mutated/cancer antigens: MUC16, CCAT2, CTAG1A, CTAG1B, MAGE A1, MAGEA2, MAGEA3, MAGE A4, MAGEA6, PRAME, PCA3, MAGE C1, MAGEC2, MAGED2, AFP, MAGEA8, MAGE9, MAGEA11, MAGEA12, IL13RA2, PLAC1, SDCCAG8, LSP1, CT45A1, CT45A2, CT45A3, CT45A5, CT45A6, CT45A8, CT45A10, CT47A1, CT47A2, CT47A3, CT47A4, CT47A5, CT47A6, CT47A8, CT47A9, CT47A10, CT47A11, CT47A12, CT47B1, SAGE1, and CT55.

In some embodiments, for example, the cancer antigen for a target cancer cell can be one or more of the mutated/cancer antigens: CD2, CD3, CD4, CD5, CD7, CD8, CD20, CD30, CD45, CD56, where the cancer is a T cell lymphoma.

In some embodiments, for example, the cancer antigen for a target cancer cell can be one or more of the mutated/cancer antigens: IDH1, ATRX, PRL3, or ETBR, where the cancer is a glioblastoma.

In some embodiments, for example, the cancer antigen for a target cancer cell can be one or more of the mutated/cancer antigens: CA125, beta-hCG, urinary gonadotropin fragment, AFP, CEA, SCC, inhibin or extradiol, where the cancer is ovarian cancer.

In some embodiments the cancer antigen for a target cancer cell may be HER2.

In some embodiments the cancer antigen for a target cancer cell may be EGFR Variant III.

In some embodiments the cancer antigen for a target cancer cell may be CD19.

In some embodiments, the SR subunit region comprises an extracellular domain (ECD) of the scavenger receptor. In some embodiments, the ECD of the scavenger receptor comprises an ECD domain of the SR comprising the ICD and the TM domains. In some embodiments the target antigen is the SR-ligand on the cancer cell, for example, any one of the ligand components from Table 2 or Table 3. In some embodiments, the SR-ECD contributes to the binding of the phagocyte to the target cell, and in turn is activated, and activates the phagocytosis of the target cell.

In some embodiments, the PSR domain optionally comprises the ECD domain or portion thereof of the respective scavenger receptor the ICD and TM domains of which is incorporated in the PSR. Therefore, in some embodiments, In some embodiments, the ECD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor. The extracellular domains of most macrophage scavenger receptors contain scavenger receptors with a broad binding specificity that may be used to discriminate between self and non-self in the nonspecific antibody-independent recognition of foreign substances. The type I and II class A scavenger receptors (SR-AII and SR-AII) are trimeric membrane glycoproteins with a small NH2-terminal intracellular domain, and an extracellular portion containing a short spacer domain, an a-helical coiled-coil domain, and a triple-helical collagenous domain. The type I receptor additionally contains a cysteine-rich COOH-terminal (SRCR) domain. These receptors are present in macrophages in diverse tissues throughout the body and exhibit an unusually broad ligand binding specificity. They bind a wide variety of polyanions, including chemically modified proteins, such as modified LDL, and they have been implicated in cholesterol deposition during atherogenesis. They may also play a role in cell adhesion processes in macrophage-associated host defense and inflammatory conditions.

In some embodiments, the SR ECD is designed to bind to pro-apoptotic cells. In some embodiments, the scavenger receptor ECD comprises a binding domain for a cell surface molecule of a cancer cell or an infected cell.

In some embodiments, the extracellular domain of the PR subunit is linked by a linker to a target cell binding domain, such as an antibody or part thereof, specific for a cancer antigen.

In some embodiments, the extracellular antigen binding domain comprises one antigen binding domain. In some embodiments, the extracellular antigen binding domain comprises more than one binding domain. In some embodiments the binding domain are scFvs. FIG. 2 shows a diagrammatic representation of an embodiment, where the PFP targets a single target on a cancer cell (left) or multiple targets (right). The one or more than one scFvs are fused to the recombinant PR at the extracellular domain. In some embodiments the scFv fraction and the extracellular domain of the PR are linked via a linker.

In some embodiments, the ECD antigen binding domain can bind to an intracellular antigen. In some embodiments, the intracellular antigen is a cancer antigen.

In some embodiments, the extracellular antigen binding domain binds to the target ligand with an affinity of less than 1000 nM. In some embodiments, the extracellular antigen binding domain binds to the target ligand with an affinity of less than 500 nM. In some embodiments, the extracellular antigen binding domain binds to the target ligand with an affinity of less than 450 nM. In some embodiments, the extracellular antigen binding domain binds to the target ligand with an affinity of less than 400 nM. In some embodiments, the extracellular antigen binding domain binds to the target ligand with an affinity of less than 350 nM. In some embodiments, the extracellular antigen binding domain binds to the target ligand with an affinity of less than 250 nM. In some embodiments, the extracellular antigen binding domain binds to the target ligand with an affinity of less than 200 nM. In some embodiments, the extracellular antigen binding domain binds to the target ligand with an affinity of less than 100 nM. In some embodiments, the extracellular antigen binding domain binds to the target ligand with an affinity ranging between than 200 nM to 1000 nM. In some embodiments, the extracellular antigen binding domain binds to the target ligand with an affinity ranging between than 300 nM to 1.5 mM. In some embodiments, the antigen binding domain binds to the target ligand with an affinity >200 nM, >300 nM or >500 nM.

In some embodiments, the extracellular antigen binding domain binds to the target ligand, where the target ligand is a T cell, the binding characteristics are such that the target T cell is not triggered to activate T cell mediated lysis of the engineered cell. In some embodiments, binding of the TCR to a ligand on the engineered cell is avoided, bypassed or inhibited.

Linker

In some embodiments, the extracellular antigen binding domains comprising the antibody specific for the antigen on a target cell, parts of an antibody that can specifically bind to an antigen on a target cell, or scFvs specific for an antigen on a target cell are linked to the TM domain or other extracellular domains by a linker. In some embodiments, where there are more than one scFv at the extracellular antigen binding domain, the more than scFvs are linked with each other by linkers.

Linkers are usually short peptide sequences. In some embodiments the linkers are stretches of Glycine and one or more Serine residues. Other amino acids preferred for short peptide linkers include but are not limited to threonine (Thr), serine (Ser), proline (Pro), glycine (Gly), aspartic acid (Asp), lysine (Lys), glutamine (Gln), asparagine (Asn), and alanine (Ala) arginine (Arg), phenylalanine (Phe), glutamic acid (Glu). Of these Pro, Thr, and Gln are frequently used amino acids for natural linkers. Pro is a unique amino acid with a cyclic side chain which causes a very restricted conformation. Pro-rich sequences are used as interdomain linkers, including the linker between the lipoyl and E3 binding domain in pyruvate dehydrogenase (GA$_2$PA$_3$PAKQEA$_3$PAPA$_2$KAEAPA$_3$PA$_2$KA) (SEQ ID NO: 27). For the purpose of the disclosure, the empirical linkers may be flexible linkers, rigid linkers, and cleavable linkers. Sequences such as (G4S)x (where x is multiple copies of the moiety, designated as 1, 2, 3, 4, and so on) (SEQ ID NO: 28) comprise a flexible linker sequence. Other flexible sequences used herein include several repeats of glycine, e.g., (Gly)6 (SEQ ID NO: 29) or (Gly)8 (SEQ ID NO: 30). On the other hand, a rigid linker may be used, for example, a linker (EAAAK)x, where x is an integer, 1, 2, 3, 4 (SEQ ID NO: 31) etc. gives rise to a rigid linker.

In some embodiments the linkers are flexible. In some embodiments the linkers comprise a hinge region. Where included, such a spacer or linker domain may position the binding domain away from the host cell surface to further enable proper cell/cell contact, binding, and activation. The length of the extracellular spacer may be varied to optimize target molecule binding based on the selected target molecule, selected binding epitope, binding domain size and affinity. In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. In some embodiments, a linker or a spacer used herein comprises an IgG4 hinge region, having a sequence: ESKYGPPCPPCP (SEQ ID NO: 32). In some embodiments, the hinge region comprises a hinge or a spacer comprising a sequence present in the extracellular regions of type 1 membrane proteins, such as CD8a, CD4, CD28 and CD7, which may be wild-type or variants thereof. In some embodiments, an extracellular spacer domain comprises all or a portion of an immunoglobulin Fc domain selected from: a CH1 domain, a CH2 domain, a CH3 domain, or combinations thereof. In some embodiments the spacer or the linker may be further modified by post-translation modifications, such as glycosylation.

In some embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D. In yet further embodiments, an extracellular spacer domain may be derived from scavenger receptor MERTK In some embodiments, the linker comprises at least 2, or at least 3 amino acids. In some embodiments, the linker comprises 4 amino acids. In some embodiments, the linker comprises 5 amino acids. In some embodiments, the linker comprises 6 amino acids. In some embodiments, the linker comprises 7 amino acids. In some embodiments, the linker comprises 8 amino acids. In some embodiments, the linker comprises 9 amino acids. In some embodiments, the linker comprises 8 amino acids. In some embodiments, the linker comprises 10 amino acids. In some embodiments the linker comprises greater than 10 amino acids. In some embodiments, the linker comprises 11, 12, 13, 14, 15, 16, 17, 18, 19, or 20 amino acids. In some embodiments there are 12 or more amino acids in the linker. In some embodiments, there are 14 or more amino acids in the linker. In some embodiments, there are 15 or more amino acids in the linker.

Other Fusion Proteins for Enhancement of Phagocytosis

In one aspect of the disclosure, recombinant nucleic acids are prepared which encode one or more chimeric receptors that enhance phagocytosis in macrophages principally by blocking inhibitory signals. Macrophages, especially in the tumor environment encounter phagocytosis dampening or inhibitory signals, such as CD47 mediated anti-phagocytic activity on target cells, e.g., cancer cells. Chimeric receptors are generated which when expressed in a phagocytic cell blocks CD47 signaling.

In some embodiments, other CAR fusion protein may be designed for expression in a phagocytic cell that may enhance phagocytosis. In one embodiment, provided herein is a composition comprising a recombinant nucleic acid encoding a chimeric antigen receptor (CAR) fusion protein (CFP) comprising: (a) a subunit comprising: (i) an extracellular domain; and (ii) a transmembrane domain; (b) an extracellular antigen binding domain specific to CD47 of a target cell; wherein: the extracellular domain of the subunit and the extracellular antigen binding domain are operatively linked; and the subunit does not comprise a functional intracellular domain of an endogenous receptor that binds CD47, or does not comprise an intracellular domain that activates a phosphatase. In some embodiments, the extracellular antigen binding domain is derived from signal-regulatory protein alpha (SIRPα). In some embodiments, the extracellular antigen binding domain is derived from signal-regulatory protein alpha (SIRPβ). In some embodiments, the transmembrane domain is derived from SIRPα. In some embodiments, the transmembrane domain is derived from SIRPβ.

In some embodiments, the additional CAR fusion protein (CFP) may be co-transfected with the recombinant PFP described above. In some embodiments, the scavenger receptor intracellular domain comprises a second intracellular domain comprising a signaling domain that activates phagocytosis; or a proinflammatory domain at the cytoplasmic terminus, which are operably linked. The signaling domain that activates phagocytosis is derived from a receptor selected from the group consisting of the receptors listed in Table 2.

In some embodiments, the intracellular domain with a phagocytosis signaling domain comprises a domain having one or more Immunoreceptor Tyrosine-based Activation Motif (ITAM) motifs. ITAMs are conserved sequences present in the cytoplasmic tails of several receptors of the immune system, such as T cell receptors, immunoglobulins (Ig) and FcRs. They have a conserved amino acid sequence motif consisting of paired YXXL/I motifs (Y=Tyrosine, L=Lysine and I=Isoleucine) separated by a defined interval (YXXL/I-X$_{6-8}$-YXXL/I). In addition, most ITAMs contain a negatively charged amino acid (D/E) in the +2 position relative to the first ITAM tyrosine. Phosphorylation of residues within the ITAM recruits several signaling molecules that activate phagocytosis. ITAM motifs are also present in the intracellular adapter protein, DNAX Activating Protein of 12 kDa (DAP12).

In some embodiments, the phagocytic signaling domain in the intracellular region can comprise a PI3kinase (PI3K) recruitment domain (also called PI3K binding domain). The PI3K binding domains used herein can be the respective PI3K binding domains of CD19, CD28, CSFR or PDGFR. PI3 kinase recruitment to the binding domain leads to the Akt mediated signaling cascade and activation of phagocytosis. The PI3K-Akt signaling pathway is important in phagocytosis, regulation of the inflammatory response, and other activities, including vesicle trafficking and cytoskeletal reorganization. The PI3kinase recruitment domain is an intracellular domain in a plasma membrane protein, which has tyrosine residues that can be phosphorylated, and which can in turn be recognized by the Src homology domain (SH2) domain of PI3Kp85. The SH2 domain of p85 recognizes the phosphorylated tyrosines on the cytosolic domain of the receptor. This causes an allosteric activation of p110 and the production of phosphatidylinositol-3,4,5-trisphosphate ($PIP_3$) that is recognized by the enzymes Akt and the constitutively active 3'-phosphoinositide-dependent kinase 1 (PDK1) through their plekstrin homology domains. The interaction of Akt with $PIP_3$ causes a change in the Akt conformation and phosphorylation of the residues Thr308 and Ser473 by PDK1 and rictor-mTOR complex, respectively. Phosphorylation of these two residues causes the activation of Akt which in turn phosphorylates, among other substrates, the enzyme glycogen synthase kinase-3 (GSK-3). GSK-3 has two isoforms, GSK-3a and GSK-3β both of which are constitutively active. The isoforms are structurally related but functionally nonredundant. Inactivation of GSK-3 is observed when the residues Ser21 in GSK-3a or Ser9 in GSK-3β, located in their regulatory N-terminal domains, are phosphorylated by Akt and other kinases. Inhibition of GSK-3 by phosphorylation is important for the modulation of the inflammation and in phagocytosis processes.

In some embodiments, a recombinant PFP comprises (a) an extracellular CD47 binding domain SIRPα, (b) a SIRPβ transmembrane domain, and (c) an intracellular domain of SIRPβ. SIRPβ signaling can activate pro-phagocytic signaling by engaging DAP12 activation.

Various members of the family transduce checkpoint signal upon contact with sialylated glycans on membrane proteins. In some members, the intracellular domains of the Siglec proteins comprise multiple immunoreceptor tyrosine-based inhibitory motifs (ITIMs). ITIMs share a consensus amino acid sequence in their cytoplasmic tail, namely (IN/L/S)—X—Y-X-X-(LN), where X denotes any amino acid, I=Isoleusine, V=valine, L=Lysine, S=Serine, Y=Tyrosine. Phosphorylation of the Tyrosine residues at the ITIM motif recruit either of two SH2 domain—containing negative regulators: the inositol phosphatase SHIP (Src homology 2-containing inositol polyphosphate 5-phosphatase) or the tyrosine phosphatase SHP-1 (Src homology 2-containing protein tyrosine phosphatase-1). A leucine in the (Y+2) position favors binding to SHIP, whereas an isoleucine in the (Y-2) position favors SHP-1 binding. ITIMs can also bind to another tyrosine phosphatase, SHP-2, but evidence for SHP-2 playing a functional role in ITIM-mediated inhibition is less clear than for the other mediators. Therefore, activation of the Siglec membrane proteins at the extracellular ligand binding domain by binding with a sialic acid residue, (e.g. in sialylated membrane glycan proteins), the ITIMs receive the intracellular signals, which are phosphorylated, and initiate the SHP mediated signaling for immunomodulation, including reduction in phagocytic potential.

In some embodiments the composition described herein comprises a recombinant nucleic acid construct encoding a chimeric Siglec receptor (SgR) fusion protein (SgFP), comprising: (a) a SgR subunit which comprises: (i) a transmembrane domain, and (ii) an intracellular domain comprising an intracellular signaling domain; an (a) an extracellular domain comprising an antigen binding domain specific to a sialylated glycan of a cell surface protein of a target cell; (b) wherein the transmembrane domain and the extracellular domain are operatively linked; and wherein: (i) the SgFP does not comprise a functional intracellular domain of an endogenous receptor that binds a sialylated glycan, or (ii) the SgFP comprises an intracellular signaling domain that activates phagocytosis or an inflammatory pathway. In some embodiments, the chimeric receptor is deficient in an intracellular domain, and therefore acts as a blocker for Siglec induced immunoregulatory intracellular signaling. Such is achieved by deletion of the nucleic acid region encoding the intracellular domain and cloning the remainder of the coding sequence of the Siglec receptor. This construct can be designated as a siglec intracellular domain deletion construct [SiglecAICD]. In some embodiments, the recombinant nucleic acid construct encodes a recombinant chimeric antigenic receptor comprising a cancer antigen specific scfv fused with the extracellular domain (ECD) of a siglec receptor. This allows targetability of the construct to the cancer cell. The chimeric receptor comprises the TM and the ICD of the siglec receptor, which can be the endogenous ICD, or the ICD fused with additional phagocytosis promoting domains, such as PI3K binding domain or the domains. In some embodiment, a chimeric receptor comprising an extracellular siglec domain, is co-expressed with a sialidase. The nucleic acid encoding a sialidase may be incorporated in the expression vector expressing the chimeric domain with a signal sequence for secretion. Since the sialidase is expressed by the same cell that expressed the CAR-siglec receptor, expression of sialidase deprives the ECD of the siglec from binding to its natural ligand, but is activated by the scfv binding to its receptor, thereby ensuring the specificity of action of the chimeric receptor on a cancer-antigen expressing cell.

In some embodiments, the chimeric receptors comprise one or more domains from TREM proteins, fused at the extracellular region with an antigen binding domain that can specifically bind to a cancer antigen, such as a cancer antigen-specific antibody or part or fragment thereof. In some embodiments, recombinant nucleic acids encoding a TREM chimeric antigen receptor encode a fusion proteins that comprises: (a) the at least a TREM transmembrane domain (TM) and a TREM intracellular domain (ICD); and (b) an extracellular domain (ECD) comprising an antigen binding domain that can specifically bind to a cancer antigen. The fusion proteins are designed to target cancer cells and bind to the target cancer cells via the ECD comprising the antigen binding domain, and the binding triggers and enhance phagocytosis via signaling through the TREM TM and/or the intracellular domains. The transmembrane domain of TREM trimerizes with DAP12 transmembrane domains and trigger intracellular pro-phagocytosis signaling cascade. In some embodiments, the TREM domains are contributed by TREM1, or by TREM2, or by TREM3 members. The extracellular antigen binding domain is fused to the extracellular terminus of the TREM domains through a short spacer or linker.

In some embodiments, the extracellular antigen binding domain comprises an antibody, specific to a cancer antigen. In some embodiments, the extracellular antigen binding domain comprises an antibody or an antigen binding part thereof that binds specifically to an antigen on the surface of a cancer cell.

In some embodiments the extracellular antigen binding domain is an antibody specific for a cancer antigen. In some embodiments, the extracellular antigen binding domain is a fraction of an antibody, wherein the fragment can bind specifically to the cancer antigen on a cancer cell. In some embodiments the antigen binding domain comprises a single chain variable fraction (scfv) specific for a cancer antigen binding domain.

In some embodiments, the chimeric PFP comprises an extracellular domain (ECD) targeted to bind to CD5 (CD5 binding domain), for example, comprising a heavy chain variable region (VH) having an amino acid sequence as set forth in SEQ ID NO: 1. In some embodiments, the chimeric PFP comprises a CD5 binding heavy chain variable domain comprising an amino acid sequence that has at least 80%, 85%, 90%, 95%, 96%, 97%, 98%, 99% sequence identity to SEQ ID NO: 1. In some embodiments, the extracellular domain (ECD) targeted to bind to CD5 (CD5 binding domain) comprises a light chain variable domain (VL) having an amino acid sequence as set forth in SEQ ID NO: 2. In some embodiments, the chimeric PFP comprises a CD5 binding light chain variable domain comprising an amino acid sequence that has at least 80%, 85%, 90%, 95%, 96%, 97%, 98%, 99% sequence identity to SEQ ID NO: 2.

In some embodiments, the chimeric PFP comprises an extracellular domain targeted to bind to HER2 (HER2 binding domain) having for example a heavy chain variable domain amino acid sequence as set forth in SEQ ID NO: 8 and a light chain variable domain amino acid sequence as set forth in SEQ ID NO: 9. In some embodiments, the chimeric PFP comprises a HER2 binding heavy chain variable domain comprising an amino acid sequence that has at least 80%, 85%, 90%, 95%, 96%, 97%, 98%, 99% sequence identity to SEQ ID NO: 8. In some embodiments, the chimeric PFP comprises a HER2 binding light chain variable domain comprising an amino acid sequence that has at least 80%, 85%, 90%, 95%, 96%, 97%, 98%, 99% sequence identity to SEQ ID NO: 9.

In some embodiments, the chimeric PFP comprises a hinge connecting the ECD to the transmembrane (TM). In some embodiments the hinge comprises the amino acid sequence of the hinge region of a CD8 receptor. In some embodiments, the PFP may comprise a hinge having the amino acid sequence set forth in SEQ ID NO: 7 (CD8 alpha chain hinge domain). In some embodiments, the PFP hinge region comprises an amino acid sequence that is at least 80%, 85%, 90%, 95%, 96%, 97%, 98%, 99% sequence identity to SEQ ID NO: 7.

In some embodiments, the chimeric PFP comprises a CD8 transmembrane region, for example having an amino acid sequence set forth in SEQ ID NO: 6. In some embodiments, the PFP TM region comprises an amino acid sequence that is at least 80%, 85%, 90%, 95%, 96%, 97%, 98%, 99% sequence identity to SEQ ID NO: 6.

In some embodiments, the chimeric PFP comprises an intracellular domain having an FcR domain. In some embodiments, the PFP comprises an FcR domain intracellular domain comprises an amino acid sequence set forth in SEQ ID NO: 3, or at least a sequence having 80%, 85%, 90%, 95%, 96%, 97%, 98%, 99% sequence identity to SEQ ID NO: 3.

In some embodiments, the chimeric PFP comprises an intracellular domain having a PI3K recruitment domain. In some embodiments the PI3K recruitment domain comprises an amino sequence set forth in SEQ ID NO: 4. In some embodiments the PI3K recruitment domain comprises an amino acid sequence that has at least 80%, 85%, 90%, 95%, 96%, 97%, 98%, 99% sequence identity to SEQ ID NO: 4.

In some embodiments, the chimeric PFP comprises an intracellular domain having a CD40 intracellular domain. In some embodiments the CD40 ICD comprises an amino sequence set forth in SEQ ID NO: 5. In some embodiments the CD40 ICD comprises an amino acid sequence that has at least 80%, 85%, 90%, 95%, 96%, 97%, 98%, 99% sequence identity to SEQ ID NO: 5.

TABLE 4

Structural domains of the chimeric PFP

| SEQ ID NO | Domain | Sequence |
|---|---|---|
| 1 | Anti-CD5 heavy chain variable domain | EIQLVQSGGGLVKPGGSVRISCAASGYTFTNYGMNWVRQAPG KGLEWMGWINTHTGEPTYADSFKGRFTFSLDDSKNTAYLQINS LRAEDTAVYFCTRRGYDWYFDVWGQGTTVTV |
| 2 | Anti-CD5 light chain variable domain | DIQMTQSPSSLSASVGDRVTITCRASQDINSYLSWFQQKPGKAP KTLIYRANRLESGVPSRFSGSGSGTDYTLTISSLQYEDFGIYYCQ QYDESPWTFGGGTKLEIK |
| 3 | FcR intracellular signaling domain | LYCRRLKIQVRKAAITSYEKSDGVYTGLSTRNQETYETLKHEK PPQ |
| 4 | PI3K recruitment domain | YEDMRGILYAAPQLRSIRGQPGPNHEEDADSYENM |
| 5 | CD40 intracellular domain | KKVAKKPTNKAPHPKQEPQEINFPDDLPGSNTAAPVQETLHGC QPVTQEDGKESRISVQERQ |
| 6 | CD8 alpha chain transmembrane domain | IYIWAPLAGTCGVLLLSLVIT |
| 7 | CD8 alpha chain hinge domain | ALSNSIMYFSHFVPVFLPAKPTTTPAPRPPTPAPTIASQPLSLRPE ACRPAAGGAVHTRGLD |
| 8 | Anti-HER2 heavy chain variable domain | DIQMTQSPSSLSASVGDRVTITCRASQDVNTAVAWYQQKPGK APKLLIYSASFLYSGVPSRFSGSRSGTDFTLTISSLQPEDFATYYC QQHYTTPPTFGQGTKVEIKRTGSTSGSGKPGSGEGSEVQLVE |

TABLE 4-continued

Structural domains of the chimeric PFP

| SEQ ID NO | Domain | Sequence |
|---|---|---|
| 9 | Anti-HER2 light chain variable domain | LVQPGGSLRLSCAASGFNIKDTYIHWVRQAPGKGLEWVARIYP TNGYTRYADSVKGRFTISADTSKNTAYLQMNSLRAEDTAVYY CSRWGGDGFYAMDVWGQGTLVTV |
| 17 | Signal peptide | MWLQSLLLLGTVACSIS |

TABLE 5

Linker sequences

| SEQ ID | Sequence |
|---|---|
| 10 | SSGGGGSGGGGSGGGGS |
| 11 | SGGGGSG |
| 12 | SGGG |
| 13 | GSGS |

Characteristics of the PFP:

The PFP structurally incorporates into the cell membrane of the cell in which it is expressed. Specific leader sequences in the nucleic acid construct, such as the signal peptide directs plasma membrane expression of the encoded protein. The transmembrane domain encoded by the construct incorporates the expressed protein in the plasma membrane of the cell.

In some embodiments the transmembrane domain comprises a TM domain of an FcRalpha receptor, which dimerizes with endogenous FcR-gamma receptors in the macrophages, ensuring macrophage specific expression.

The PFP renders the cell expressing it as potently phagocytic. When the recombinant nucleic acid encoding the PFP is expressed in a cell, the cell exhibits an increased phagocytosis of a target cell having the antigen of a target cell, compared to a cell not expressing the recombinant nucleic acid. When the recombinant nucleic acid is expressed in a cell, the cell exhibits an increased phagocytosis of a target cell having the antigen of a target cell, compared to a cell not expressing the recombinant nucleic acid. In some embodiments, the recombinant nucleic acid when expressed in a cell, the cell exhibits at least 2-fold increased phagocytosis of a target cell having the antigen of a target cell, compared to a cell not expressing the recombinant nucleic acid. In some embodiments, the recombinant nucleic acid when expressed in a cell, the cell exhibits at least 3-fold, 4-fold, 5-fold, 6-fold, 7-fold, 8-fold, 9-fold, 10-fold, 20-fold 30-fold or at least 5-fold increased phagocytosis of a target cell having the antigen of a target cell, compared to a cell not expressing the recombinant nucleic acid. In some embodiments, the composition comprises a recombinant nucleic acid encoding a phagocytic or tethering receptor (PR) fusion protein (PFP) comprising: (a) a PR subunit comprising: (i) a transmembrane domain, and (ii) an intracellular domain comprising an intracellular signaling domain; and (b) an extracellular domain comprising an antigen binding domain specific to an antigen of a target cell; wherein the transmembrane domain and the extracellular domain are operatively linked; and wherein upon binding of the PFP to the antigen of the target cell, the killing or phagocytosis activity of a cell expressing the PFP is increased by at least greater than 10% compared to a cell not expressing the PFP. In some embodiments, the phagocytosis activity of a cell expressing the PFP is increased by at least greater than 10% compared to a cell not expressing the PFP. In some embodiments, the phagocytosis activity of a cell expressing the PFP is increased by at least greater than 11% compared to a cell not expressing the PFP. In some embodiments, the phagocytosis activity of a cell expressing the PFP is increased by at least greater than 12% compared to a cell not expressing the PFP. In some embodiments, the phagocytosis activity of a cell expressing the PFP is increased by at least greater than 13% compared to a cell not expressing the PFP. In some embodiments, the phagocytosis activity of a cell expressing the PFP is increased by at least greater than 14% compared to a cell not expressing the PFP. In some embodiments, the phagocytosis activity of a cell expressing the PFP is increased by at least greater than 15% compared to a cell not expressing the PFP. In some embodiments, the phagocytosis activity of a cell expressing the PFP is increased by at least greater than 16% compared to a cell not expressing the PFP. In some embodiments, the phagocytosis activity of a cell expressing the PFP is increased by at least greater than 17% compared to a cell not expressing the PFP. In some embodiments, the phagocytosis activity of a cell expressing the PFP is increased by at least greater than 18% compared to a cell not expressing the PFP. In some embodiments, the phagocytosis activity of a cell expressing the PFP is increased by at least greater than 19% compared to a cell not expressing the PFP. In some embodiments, the phagocytosis activity of a cell expressing the PFP is increased by at least greater than 20% compared to a cell not expressing the PFP. In some embodiments, the phagocytosis activity of a cell expressing the PFP is increased by at least greater than 30% compared to a cell not expressing the PFP. In some embodiments, the phagocytosis activity of a cell expressing the PFP is increased by at least greater than 40% compared to a cell not expressing the PFP. In some embodiments, the phagocytosis activity of a cell expressing the PFP is increased by at least greater than 50% compared to a cell not expressing the PFP. In some embodiments, the phagocytosis activity of a cell expressing the PFP is increased by at least greater than 60% compared to a cell not expressing the PFP. In some embodiments, the phagocytosis activity of a cell expressing the PFP is increased by at least greater than 70% compared to a cell not expressing the PFP. In some embodiments, the phagocytosis activity of a cell expressing the PFP is increased by at least greater than 80% compared to a cell not expressing the PFP. In some embodiments, the phagocytosis activity of a cell expressing the PFP is increased by at least greater than 90% compared to a cell not expressing the PFP. In some embodiments, the phagocytosis activity of a cell expressing the PFP is increased by at least greater than 100% compared to a cell not expressing the PFP.

In some embodiments, the phagocytosis activity of a cell expressing the PFP is increased by at least greater than 2-fold compared to a cell not expressing the PFP. In some embodiments, the phagocytosis activity of a cell expressing the PFP is increased by at least greater than 4-fold compared to a cell not expressing the PFP. In some embodiments, the phagocytosis activity of a cell expressing the PFP is increased by at least greater than 6-fold compared to a cell not expressing the PFP. In some embodiments, the phagocytosis activity of a cell expressing the PFP is increased by at least greater than 8-fold compared to a cell not expressing the PFP. In some embodiments, the phagocytosis activity of a cell expressing the PFP is increased by at least greater than 10-fold compared to a cell not expressing the PFP. In some embodiments, the phagocytosis activity of a cell expressing the PFP is increased by at least greater than 20-fold compared to a cell not expressing the PFP. In some embodiments, the phagocytosis activity of a cell expressing the PFP is increased by at least greater than 50-fold compared to a cell not expressing the PFP. In some embodiments, the phagocytosis activity of a cell expressing the PFP is increased by about 50-fold compared to a cell not expressing the PFP.

In some embodiments, the phagocytosis associated killing activity of a cell expressing the PFP is increased by at least greater than 10% compared to a cell not expressing the PFP. In some embodiments, the phagocytosis associated killing activity of a cell expressing the PFP is increased by at least greater than 20% compared to a cell not expressing the PFP. In some embodiments, the phagocytosis associated killing activity of a cell expressing the PFP is increased by at least greater than 30% compared to a cell not expressing the PFP. In some embodiments, the phagocytosis associated killing activity of a cell expressing the PFP is increased by at least greater than 40% compared to a cell not expressing the PFP. In some embodiments, the phagocytosis associated killing activity of a cell expressing the PFP is increased by at least greater than 50% compared to a cell not expressing the PFP. In some embodiments, the phagocytosis associated killing activity of a cell expressing the PFP is increased by at least greater than 60% compared to a cell not expressing the PFP. In some embodiments, the phagocytosis associated killing activity of a cell expressing the PFP is increased by at least greater than 70% compared to a cell not expressing the PFP. In some embodiments, the phagocytosis associated killing activity of a cell expressing the PFP is increased by at least greater than 80% compared to a cell not expressing the PFP. In some embodiments, the phagocytosis associated killing activity of a cell expressing the PFP is increased by at least greater than 90% compared to a cell not expressing the PFP. In some embodiments, the phagocytosis associated killing activity of a cell expressing the PFP is increased by at least greater than 100% compared to a cell not expressing the PFP.

In some embodiments, the phagocytosis associated killing activity of a cell expressing the PFP is increased by at least greater than 2-fold compared to a cell not expressing the PFP. In some embodiments, the phagocytosis associated killing activity of a cell expressing the PFP is increased by at least greater than 4-fold compared to a cell not expressing the PFP. In some embodiments, the phagocytosis associated killing activity of a cell expressing the PFP is increased by at least greater than 6-fold compared to a cell not expressing the PFP. In some embodiments, the phagocytosis associated killing activity of a cell expressing the PFP is increased by at least greater than 8-fold compared to a cell not expressing the PFP. In some embodiments, the phagocytosis associated killing activity of a cell expressing the PFP is increased by at least greater than 10-fold compared to a cell not expressing the PFP. In some embodiments, the phagocytosis associated killing activity of a cell expressing the PFP is increased by at least greater than 20-fold compared to a cell not expressing the PFP. In some embodiments, the phagocytosis associated killing activity of a cell expressing the PFP is increased by at least greater than 30-fold compared to a cell not expressing the PFP. In some embodiments, the phagocytosis associated killing activity of a cell expressing the PFP is increased by at least greater than 40-fold compared to a cell not expressing the PFP. In some embodiments, the phagocytosis associated killing activity of a cell expressing the PFP is increased by at least greater than 50-fold compared to a cell not expressing the PFP. In some embodiments, the phagocytosis associated killing activity of a cell expressing the PFP is increased by at least greater than 100-fold compared to a cell not expressing the PFP. In some embodiments, the phagocytosis associated killing activity of a cell expressing the PFP is increased by about 100-fold compared to a cell not expressing the PFP.

In some embodiments, the phagocytosis associated killing activity of a cell expressing the PFP is increased by at least greater than 2-fold compared to a cell not expressing the PFP.

In some embodiments, when the recombinant nucleic acid is expressed in a cell, the cell exhibits an increased cytokine production. The cytokine can comprise any one of: IL-1, IL-6, IL-12, IL-23, TNF, CXCL9, CXCL10, CXCL11, IL-18, IL-23, IL-27 and interferons.

In some embodiments, when the recombinant nucleic acid is expressed in a cell, the cell exhibits an increased cell migration. Enhanced cell migration may be detected in cell culture by standard motility assays. In some embodiments, actin filament rearrangements may be detected and monitored using phalloidin staining and fluorescent microscopy. In some instances, time-lapsed microscopy is used for the purpose.

In some embodiments, when the recombinant nucleic acid is expressed in a cell, the cell exhibits an increased immune activity. In some embodiments, when the recombinant nucleic acid is expressed in a cell, the cell exhibits an increased expression of MHC II. In some embodiments, when the recombinant nucleic acid is expressed in a cell, the cell exhibits an increased expression of CD80. In some embodiments, when the recombinant nucleic acid is expressed in a cell, the cell exhibits an increased expression of CD86. In some embodiments, when the recombinant nucleic acid is expressed in a cell, the cell exhibits an increased iNOS production.

In some embodiments, when the recombinant nucleic acid is expressed in a cell, the cell exhibits decreased trogocytosis of a target cell expressing the antigen of a target cell compared to a cell not expressing the recombinant nucleic acid.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked. In embodiments any one of the chimeric receptors may be enzymatically or functionally active such that, when the extracellular domain is bound by a ligand, a signal is transduced to polarize a macrophage.

Methods for Preparing Chimeric Phagocytic Receptors (CAR-P) and Engineered CAR-P Macrophages The method for preparing CAR-Ps comprise the steps of (1) screening for PSR subunit framework; (2) screening for antigen binding specificity; (3) CAR-P recombinant nucleic acid constructs; (4) engineering cells and validation.

Screening for PSR subunit framework: As described above, the design of the receptor comprises at least of one phagocytic receptor domain, which enables the enhanced signaling of phagocytosis. In essence a large body of plasma membrane proteins can be screened for novel phagocytic functions or enhancements domains. Methods for screening phagocytic receptor subunits are known to one of skill in the art. Additional information can be found in The Examples section. In general, functional genomics and reverse engineering is often employed to obtain a genetic sequence encoding a functionally relevant protein polypeptide or a portion thereof. In some embodiments, primers and probes are constructed for identification, and or isolation of a protein, a polypeptide or a fragment thereof or a nucleic acid fragment encoding the same. In some embodiments, the primer or probe may be tagged for experimental identification. In some embodiments, tagging of a protein or a peptide may be useful in intracellular or extracellular localization.

Potential antibodies are screened for selecting specific antigen binding domains of high affinity. Methods of screening for antibodies or antibody domains are known to one of skill in the art. Specific examples provide further information. Examples of antibodies and fragments thereof include, but are not limited to IgAs, IgDs, IgEs, IgGs, IgMs, Fab fragments, F(ab')2 fragments, monovalent antibodies, ScFv fragments, scRv-Fc fragments, IgNARs, hcIgGs, VhH antibodies, nanobodies, and alphabodies.

Commercially available antibodies can be adapted to generate extracellular domains of a chimeric receptor. Examples of commercially available antibodies include, but are not limited to: anti-HGPRT, clone 13H11.1 (EMD Millipore), anti-ROR1 (ab135669) (Abcam), anti-MUC1 [EP1024Y] (ab45167) (Abcam), anti-MUC16 [X75] (ab1107) (Abcam), anti-EGFRvIII [L8A4] (Absolute antibody), anti-Mesothelin [EPR2685 (2)] (ab134109) (Abcam), HER2 [3B5] (ab16901) (Abcam), anti-CEA (LS-C84299-1000) (LifeSpan BioSciences), anti-BCMA (ab5972) (Abcam), anti-Glypican 3 [9C2] (ab129381) (Abcam), anti-FAP (ab53066) (Abcam), anti-EphA2 [RM-0051-8F21] (ab73254) (Abcam), anti-GD2 (LS-0546315) (LifeSpan BioSciences), anti-CD19 [2E2B6B10] (ab31947) (Abeam), anti-CD20 [EP459Y] (ab78237) (Abeam), anti-CD30 [EPR4102] (ab134080) (Abeam), anti-CD33 [SP266] (ab199432) (Abcam), anti-CD123 (ab53698) (Abcam), anti-CD133 (BioLegend), anti-CD123 (1A3H4) ab181789 (Abeam), and anti-CD171 (L1.1) (Invitrogen antibodies). Techniques for creating antibody fragments, such as ScFvs, from known antibodies are routine in the art.

The recombinant nucleic acid can be generated following molecular biology techniques known to one of skill in the art. The methods include but are not limited to designing primers, generating PCR amplification products, restriction digestion, ligation, cloning, gel purification of cloned product, bacterial propagation of cloned DNA, isolation and purification of cloned plasmid or vector. General guidance can be found in: Molecular Cloning of PCR Products: by Michael Finney, Paul E. Nisson, Ayoub Rashtchian in Current Protocols in Molecular Biology, Volume 56, Issue 1 (First published: 1 Nov. 2001); Recombinational Cloning by Jaehong Park, Joshua LaBaer in Current Protocols in Molecular Biology Volume 74, Issue 1 (First published: 15 May 2006) and others. In some embodiments specific amplification techniques may be used, such as TAS technique (Transcription-based Amplification System), described by Kwoh et al. in 1989; the 3SR technique, which are hereby incorporated by reference. (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

In some embodiments the recombinant nucleic acid sequence is optimized for expression in human.

DNA, mRNA and Circular RNA: In some embodiments, naked DNA or messenger RNA (mRNA) may be used to introduce the nucleic acid inside the cell. In some embodiments, DNA or mRNA encoding the PFP is introduced into the phagocytic cell by lipid nanopaticle (LNP) encapsulation. mRNA is single stranded and may be codon optimized. In some embodiments the mRNA may comprise one or more modified or unnatural bases such as 5'-Methylcytosine, or Pseudouridine. mRNA may be 50-10,000 bases long. In one aspect the transgene is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. LNP encapsulated DNA or RNA can be used for transfecting a macrophage or can be administered to a subject.

In some embodiments, circular RNA (circRNAs) encoding the PFP is used. In circular RNAs (circRNAs) the 3' and 5' ends are covalently linked, constitute a class of RNA. CircRNA may be delivered inside a cell or a subject using LNPs.

Transcription Regulatory Elements in the Recombinant Nucleic Acid Construct

In some embodiments, the recombinant nucleic comprises one or more regulatory elements within the noncoding regions that can be manipulated for desired expression profiles of the encoded proteins. In some embodiments, the noncoding region may comprise suitable enhancer. In some embodiments, the enhancer comprises a binding region for a regulator protein or peptide may be added to the cell or the system comprising the cell, for commencement of expression of the protein encoded under the influence of the enhancer. Conversely, a regulatory element may comprise a protein binding domain that remains bound with the cognate protein and continue to inhibit transcription and/or translation of recombinant protein until an extracellular signal is provided for the protein to decouple from the bound position to allow commencement of the protein synthesis. Examples include but are not limited to Tetracyclin-inducible (Tet-Inducible or Tet-on) and Tetracyclin repressible (Tet-off) systems known to one of skill in the art.

Construct Comprising Metabolic Switch:

In some embodiments the 5' and 3' untranslated regions flanking the coding regions of the construct may be manipulated for regulation of expression of the recombinant protein encoded by the nucleic acid constructs described above. For instance, the 3'UTR may comprise one or more elements that are inserted for stabilizing the mRNA. In some embodiments, AU-Rich Elements (ARE) sequences are inserted in the 3' UTR that result in binding of RNA binding proteins that stabilize or destabilize the mRNA, allowing control of the mRNA half-life.

In some embodiments the 3'UTR may comprise a conserved region for RNA binding proteins (eg GAPDH) binding to mature mRNA strand preventing translation. In some embodiments, glycolysis results in the uncoupling of the RNA binding proteins (eg GAPDH) allowing for mRNA strand translation. The principle of the metabolic switch is to trigger expression of target genes when a cell enters a certain metabolic state. In resting cells, for example, GAPDH is a RNA binding protein (RBP). It binds to ARE sequences in the 3'UTR, preventing translation of mRNA. When the cell enters glycolysis, GAPDH is required to convert glucose into ATP, coming off the mRNA allowing for translation of the protein to occur. In some embodiments, the environment in which the cell comprising the recombinant nucleic acid is present, provides the metabolic switch to the gene expression. For example, hypoxic condition can trigger the metabolic switch inducing the disengaging of GAPDH from the mRNA. The expression of the mRNA therefore can be induced only when the macrophage leaves the circulation and enters into a tumor environment, which is hypoxic. This allows for systemic administration of the nucleic acid or a cell comprising the nucleic acid, but ensures a local expression, specifically targeting the tumor environment.

In some embodiments the nucleic acid construct can be a split construct, for example, allowing a portion of the construct to be expressed under the control of a constitutive expression system whereas another portion of the nucleic acid is expressed under control of a metabolic switch, as described above. In some embodiments the nucleic acid may be under bicistronic control. In some embodiments, the bicistronic vector comprises a first coding sequence under a first regulatory control, comprising the coding sequence of a target recognition moiety which may be under constitutive control; and a second coding sequence encoding an inflammatory gene expression which may be under the metabolic switch. In some embodiments the bicistronic vector may be unidirectional. In some embodiments the bicistronic vector may be bidirectional.

In some embodiments, the ARE sequences comprise protein binding motifs for binding ARE sequence that bind to ADK, ALDH18A1, ALDH6A1, ALDOA, ASS1, CCBL2, CS, DUT, ENO1, FASN, FDPS, GOT2, HADHB, HK2, HSD17B10, MDH2, NME1, NQO1, PKM2, PPP1CC, SUCLG1, TP11, GAPDH, or LDH.

Delivery of Nucleic Acids into a Cell:

In some embodiments the plasmid vector is introduced or incorporated in the cell by known methods of transfection, such as using lipofectamine, or calcium phosphate, or via physical means such as electroporation or nucleofection. In some embodiments the viral vector is introduced or incorporated in the cell by infection, a process commonly known as viral transduction.

In some embodiments, recombinant nucleic acid is integrated or incorporated in an expression vector. A vector comprises one or more promoters, and other regulatory components, including enhancer binding sequence, initiation and terminal codons, a 5'UTR, a 3'UTR comprising a transcript stabilization element, optional conserved regulatory protein binding sequences and others. In some embodiments, the vector for expression of the chimeric antigen receptor PFP is a plasmid.

In some embodiments the vectors of use in the application are specifically enhanced for expression. Other exemplary vectors of use throughout the process include phages, cosmids, or artificial chromosomes.

Viral Vectors: In some embodiments, the vector for expression of the PFP is of a viral origin, namely a lentiviral vector or an adenoviral vector. In some embodiments, the nucleic acid encoding the recombinant nucleic acid is encoded by a lentiviral vector. In some embodiments the lentiviral vector is prepared in-house and manufactured in large scale for the purpose. In some embodiments, commercially available lentiviral vectors are utilized, as is known to one of skill in the art.

In some embodiments the viral vector is an Adeno-Associated Virus (AAV) vector.

Lipid nanoparticle mediated delivery: Lipid nanoparticles (LNP) may comprise a polar and or a nonpolar lipid. In some embodiments cholesterol is present in the LNPs for efficient delivery. LNPs are 100-300 nm in diameter provide efficient means of mRNA delivery to various cell types, including macrophages. In some embodiments, LNP may be used to introduce the recombinant nucleic acids into a cell in in vitro cell culture. In some embodiments, the LNP encapsulates the nucleic acid wherein the nucleic acid is a naked DNA molecule. In some embodiments, the LNP encapsulates the nucleic acid wherein the nucleic acid is an mRNA molecule. In some embodiments, the LNP encapsulates the nucleic acid wherein the nucleic acid is inserted in a vector, such as a plasmid vector. In some embodiments, the LNP encapsulates the nucleic acid wherein the nucleic acid is a circRNA molecule.

In some embodiments, the LNP is used to deliver the nucleic acid into the subject. LNP can be used to deliver nucleic acid systemically in a subject. It can be delivered by injection. In some embodiments, the LNP comprising the nucleic acid is injected by intravenous route. In some embodiments the LNP is injected subcutaneously.

Pharmaceutical Composition

Provided herein is a pharmaceutical composition, comprising engineered macrophages comprising a recombinant nucleic acid encoding the PFP and a pharmaceutically acceptable excipient.

Also provided herein is a pharmaceutical composition, comprising a recombinant nucleic acid encoding the PFP and a pharmaceutically acceptable excipient. The pharmaceutical composition may comprise DNA, mRNA or circRNA or a liposomal composition of any one of these. The liposome is a LNP.

Also provided herein is a pharmaceutical composition comprising a vector comprising the recombinant nucleic acid encoding the PFP and a pharmaceutically acceptable excipient. The pharmaceutical composition may comprise DNA, mRNA or circRNA inserted in a plasmid vector or a viral vector.

In some embodiments the engineered macrophages are grown in cell culture sufficient for a therapeutic administration dose, and washed, and resuspended into a pharmaceutical composition.

In some embodiments the excipient comprises a sterile buffer, (e.g. HEPES or PBS) at neutral pH. In some embodiment, the pH of the pharmaceutical composition is at 7.5. In some embodiments, the pH may vary within an acceptable range. In some embodiments, the engineered cells may be comprised in sterile enriched cell suspension medium comprising complement deactivated or synthetic serum. In some embodiments the pharmaceutic composition further comprises cytokines, chemokines or growth factors for cell preservation and function.

In some embodiments, the pharmaceutical composition may comprise additional therapeutic agents, co-administered with the engineered cells.

Treatment Methods

Provided herein are methods for treating cancer in a subject using a pharmaceutical composition comprising engineered phagocytic cells, particularly macrophages, expressing recombinant nucleic acid encoding a phagocytic receptor (PR) fusion protein (PFP), which is specifically designed to target, attack and kill cancer cells. The PFP is also designated as a chimeric antigenic receptor for phagocytosis (CAR-P), and both the terms may be used interchangeably herein. The engineered phagocytic cells are also designated as CAR-P cells in the descriptions herein.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells. In some aspects a patient or a subject having cancer, is treated with autologous cells, the method comprising, isolation of PBMC-derived macrophages, modifying the macrophages ex vivo to generate highly phagocytic macrophages capable of tumor lysis by introducing into the macrophages a recombinant nucleic acid encoding chimeric antigenic receptor for phagocytosis which is a phagocytic receptor fusion protein (PFP), and administering the modified macrophages into the patient or the subject.

In some aspects, a subject is administered one or more doses of a pharmaceutical composition comprising therapeutic phagocytic cells, wherein the cells are allogeneic. An HLA may be matched for compatibility with the subject, and such that the cells do not lead to graft versus Host Disease, GVHD. A subject arriving at the clinic is HLA typed for determining the HLA antigens expressed by the subject.

HLA-typing is conventionally carried out by either serological methods using antibodies or by PCR-based methods such as Sequence Specific Oligonucleotide Probe Hybridization (SSOP), or Sequence Based Typing (SBT).

The sequence information may be identified by either sequencing methods or methods employing mass spectrometry, such as liquid chromatography—mass spectrometry (LC-MS or LC-MS/MS, or alternatively HPLC-MS or HPLC-MS/MS). These sequencing methods may be well-known to a skilled person and are reviewed in Medzihradszky K F and Chalkley R J. Mass Spectrom Rev. 2015 January-February; 34(1):43-63.

In some aspects, the phagocytic cell is derived from the subject, transfected or transduced with the recombinant nucleic acid in vitro, expanded in cell culture in vitro for achieving a number suitable for administration, and then administered to the subject. In some embodiments, the steps of transfected or transduced with the recombinant nucleic acid in vitro, expanded in cell culture in vitro for achieving a number suitable for administration takes 2 days, or 3 days, or 4 days or 5 days or 6 days or 7 days or 8 days or 9 days or 10 days.

In some embodiments, sufficient quantities of transfected or transduced macrophages comprising the recombinant nucleic acid are preserved aseptically, which are administered to the subject as "off the shelf" products after HLA typing and matching the product with the recipients HLA subtypes. In some embodiments, the engineered phagocytes are cryopreserved. In some embodiments, the engineered phagocytes are cryopreserved in suitable media to withstand thawing without considerable loss in cell viability.

In some embodiment, the subject is administered a pharmaceutical composition comprising the DNA, or the mRNA or the circRNA in a vector, or in a pharmaceutically acceptable excipient described above.

In some embodiments the administration of the off the shelf cellular products may be instantaneous, or may require 1 day, 2 days or 3 days or 4 days or 5 days or 6 days or 7 days or more prior to administration. The pharmaceutical composition comprising cell, or nucleic acid may be preserved over time from preparation until use in frozen condition. In some embodiments, the pharmaceutical composition may be thawed once. In some embodiments, the pharmaceutical composition may be thawed more than once. In some embodiments, the pharmaceutical composition is stabilized after a freeze-thaw cycle prior administering to the subject. In some embodiments the pharmaceutical composition is tested for final quality control after thawing prior administration.

In some embodiments, a composition comprising 10^6 engineered cells are administered per administration dose. In some embodiments, a composition comprising 10^7 engineered cells are administered per administration dose. In some embodiments, a composition comprising 5×10^7 engineered cells are administered per administration dose. In some embodiments, a composition comprising 10^8 engineered cells are administered per administration dose. In some embodiments, a composition comprising 2×10^8 engineered cells are administered per administration dose. In some embodiments, a composition comprising 5×10^8 engineered cells are administered per administration dose. In some embodiments, a composition comprising 10^9 engineered cells are administered per administration dose. In some embodiments, a composition comprising 10^10 engineered cells are administered per administration dose.

In some embodiments, the engineered phagocytic cells are administered once.

In some embodiments, the engineered phagocytic cells are administered more than once.

In some embodiments, the engineered phagocytic cells are twice, thrice, four times, five times, six times, seven times, eight times, nine times, or ten times or more to a subject over a span of time comprising a few months, a year or more.

In some embodiments, the engineered phagocytic cells are administered twice weekly.

In some embodiments, the engineered phagocytic cells are administered once weekly.

In some embodiments, the engineered phagocytic cells are administered once every two weeks.

In some embodiments, the engineered phagocytic cells are administered once every three weeks.

In some embodiments, the engineered phagocytic cells are administered once monthly.

In some embodiments, the engineered phagocytic cells are administered once in every 2 months, once in every 3 months, once in every 4 months, once in every 5 months or once in every 6 months.

In some embodiments, the engineered phagocytic cells are administered by injection.

In some embodiments, the engineered phagocytic cells are administered by infusion.

In some embodiments, the engineered phagocytic cells are administered by intravenous infusion.

In some embodiments, the engineered phagocytic cells are administered by subcutaneous infusion.

EMBODIMENTS

1. A composition comprising a recombinant nucleic acid encoding a phagocytic or tethering receptor (PR) fusion protein (PFP) comprising:
(a) a PR subunit comprising:
(i) a transmembrane domain, and
(ii) an intracellular domain comprising an intracellular signaling domain; and
(b) an extracellular domain comprising an antigen binding domain specific to an antigen of a target cell;
wherein the transmembrane domain and the extracellular domain are operatively linked; and wherein upon binding of the PFP to the antigen of the target cell, the killing or phagocytosis activity of a cell expressing the PFP is increased by at least greater than 20% compared to a cell not expressing the PFP.

2. The composition of embodiment 1, wherein the intracellular signaling domain is derived from a phagocytic or tethering receptor or wherein the intracellular signaling domain comprises a phagocytosis activation domain.

3. The composition of embodiment 1 or 2, wherein the intracellular signaling domain is derived from a receptor other than a phagocytic receptor selected from Megf10, MerTk, FcR-alpha, or Bai1.

4. The composition of any one of embodiments 1-3, wherein the intracellular signaling domain is derived from a receptor selected from the group consisting of the receptors listed in Table 2.

5. The composition of any one of embodiments 1-4, wherein the intracellular signaling domain comprises a pro-inflammatory signaling domain.

6. The composition of embodiment 5, wherein the intracellular signaling domain comprises a pro-inflammatory signaling domain that is not a PI3K recruitment domain.

7. A composition comprising a recombinant nucleic acid encoding a phagocytic or tethering receptor (PR) fusion protein (PFP) comprising:
(a) a PR subunit comprising:
(i) a transmembrane domain, and
(ii) an intracellular domain comprising an intracellular signaling domain; and
(b) an extracellular domain comprising an antigen binding domain specific to an antigen of a target cell;
wherein the transmembrane domain and the extracellular domain are operatively linked; and
wherein the intracellular signaling domain is derived from a phagocytic receptor other than a phagocytic receptor selected from Megf10, MerTk, FcR-alpha, or Bai1.

8. The composition of embodiment 7, wherein upon binding of the PFP to the antigen of the target cell, the killing activity of a cell expressing the PFP is increased by at least greater than 20% compared to a cell not expressing the PFP.

9. The composition of embodiment 7 or 8, wherein the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169.

10. The composition of any one of embodiments 7-9, wherein the intracellular signaling domain comprises a pro-inflammatory signaling domain.

11. A composition comprising a recombinant nucleic acid encoding a phagocytic or tethering receptor (PR) fusion protein (PFP) comprising:
(a) a PR subunit comprising:
(i) a transmembrane domain, and
(ii) an intracellular domain comprising an intracellular signaling domain; and (b) an extracellular domain comprising an antigen binding domain specific to an antigen of a target cell;
wherein the transmembrane domain and the extracellular domain are operatively linked; and
wherein the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169.

12. The composition of embodiment 11, wherein upon binding of the PFP to the antigen of the target cell, the killing activity of a cell expressing the PFP is increased by at least greater than 55% compared to a cell not expressing the PFP.

13. The composition of embodiment 11 or 12, wherein the intracellular signaling domain is derived from a phagocytic receptor other than a phagocytic receptor selected from Megf10, MerTk, FcR-alpha, or Bai1.

14. The composition of any one of embodiments 11-13, wherein the intracellular signaling domain comprises a pro-inflammatory signaling domain 15. The composition of embodiment 14, wherein the intracellular signaling domain comprises a pro-inflammatory signaling domain that is not a PI3K recruitment domain.

16. A composition comprising a recombinant nucleic acid encoding a phagocytic or tethering receptor (PR) fusion protein (PFP) comprising:
(a) a PR subunit comprising:
(i) a transmembrane domain, and
(ii) an intracellular domain comprising an intracellular signaling domain; and
(b) an extracellular domain comprising an antigen binding domain specific to an antigen of a target cell;
wherein the transmembrane domain and the extracellular domain are operatively linked; and
wherein the intracellular signaling domain comprises a pro-inflammatory signaling domain that is not a PI3K recruitment domain.

17. The composition of embodiment 16, wherein upon binding of the PFP to the antigen of the target cell, the killing activity of a cell expressing the PFP is increased by at least greater than 20% compared to a cell not expressing the PFP.

18. The composition of embodiment 16 or 17, wherein the intracellular signaling domain is derived from a phagocytic receptor.

19. The composition of any one of embodiments 16-18, wherein the intracellular signaling domain is derived from a phagocytic receptor other than a phagocytic receptor selected from Megf10, MerTk, FcR-alpha, or Bai1.

20. The composition of any one of embodiments 16-19, wherein the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169.

21. The composition of any one of embodiments 1-15, wherein the intracellular signaling domain comprises a PI3K recruitment domain.

22. The composition of any one of the preceding embodiments, wherein the PFP functionally incorporates into a cell membrane of a cell when the PFP is expressed in the cell.

23. The composition of any one of the preceding embodiments, wherein a cell expressing the PFP exhibits an increase in phagocytosis of a target cell expressing the antigen compared to a cell not expressing the PFP.

24. The composition of embodiment 23, wherein a cell expressing the PFP exhibits at least a 1.1-fold increase in phagocytosis of a target cell expressing the antigen compared to a cell not expressing the PFP.

25. The composition of any one of the preceding embodiments, wherein a cell expressing the PFP exhibits at least a 2-fold, 3-fold, 4-fold, 5-fold, 6-fold, 7-fold, 8-fold, 9-fold, 10-fold, 20-fold, 30-fold or 50-fold increase in phagocytosis of a target cell expressing the antigen compared to a cell not expressing the PFP.

26. The composition of any one of the preceding embodiments, wherein the target cell expressing the antigen is a cancer cell.

27. The composition of any one of the preceding embodiments, wherein the target cell expressing the antigen is at least 0.8 microns in diameter.

28. The composition of any one of the preceding embodiments, wherein the intracellular signaling domain is derived from a scavenger receptor.

29. The composition of any one of the preceding embodiments, wherein a cell expressing the PFP exhibits an increase in production of a cytokine compared to a cell not expressing the PFP.

30. The composition according to embodiment 29, wherein the cytokine is selected from the group consisting of IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon and combinations thereof.

31. The composition of any one of the preceding embodiments, wherein a cell expressing the PFP exhibits an increase in effector activity compared to a cell not expressing the PFP.

32. The composition of any one of the preceding embodiments, wherein a cell expressing the PFP exhibits an increase in cross-presentation compared to a cell not expressing the PFP.

33. The composition of any one of the preceding embodiments, wherein a cell expressing the PFP exhibits an increase in expression of an MHC class II protein compared to a cell not expressing the PFP 34. The composition of any one of the preceding embodiments, wherein a cell expressing the PFP exhibits an increase in expression of CD80 compared to a cell not expressing the PFP.

35. The composition of any one of the preceding embodiments, wherein a cell expressing the PFP exhibits an increase in expression of CD86 compared to a cell not expressing the PFP.

36. The composition of any one of the preceding embodiments, wherein a cell expressing the PFP exhibits an increase in expression of MHC class I protein compared to a cell not expressing the PFP.

37. The composition of any one of the preceding embodiments, wherein a cell expressing the PFP exhibits an increase in expression of TRAIL/TNF Family death receptors compared to a cell not expressing the PFP.

38. The composition of any one of the preceding embodiments, wherein a cell expressing the PFP exhibits an increase in expression of B7-H2 compared to a cell not expressing the PFP.
39. The composition of any one of the preceding embodiments, wherein a cell expressing the PFP exhibits an increase in expression of LIGHT compared to a cell not expressing the PFP.
40. The composition of any one of the preceding embodiments, wherein a cell expressing the PFP exhibits an increase in expression of HVEM compared to a cell not expressing the PFP.
41. The composition of any one of the preceding embodiments, wherein a cell expressing the PFP exhibits an increase in expression of CD40 compared to a cell not expressing the PFP.
42. The composition of any one of the preceding embodiments, wherein a cell expressing the PFP exhibits an increase in expression of TL1A compared to a cell not expressing the PFP.
43. The composition of any one of the preceding embodiments, wherein a cell expressing the PFP exhibits an increase in expression of 41BBL compared to a cell not expressing the PFP.
44. The composition of any one of the preceding embodiments, wherein a cell expressing the PFP exhibits an increase in expression of OX40L compared to a cell not expressing the PFP.
45. The composition of any one of the preceding embodiments, wherein a cell expressing the PFP exhibits an increase in expression of GITRL death receptors compared to a cell not expressing the PFP.
46. The composition of any one of the preceding embodiments, wherein a cell expressing the PFP exhibits an increase in expression of CD30L compared to a cell not expressing the PFP.
47. The composition of any one of the preceding embodiments, wherein a cell expressing the PFP exhibits an increase in expression of TIM4 compared to a cell not expressing the PFP.
48. The composition of any one of the preceding embodiments, wherein a cell expressing the PFP exhibits an increase in expression of TIM1 ligand compared to a cell not expressing the PFP.
49. The composition of any one of the preceding embodiments, wherein a cell expressing the PFP exhibits an increase in expression of SLAM compared to a cell not expressing the PFP.
50. The composition of any one of the preceding embodiments, wherein a cell expressing the PFP exhibits an increase in expression of CD48 compared to a cell not expressing the PFP.
51. The composition of any one of the preceding embodiments, wherein a cell expressing the PFP exhibits an increase in expression of CD58 compared to a cell not expressing the PFP.
52. The composition of any one of the preceding embodiments, wherein a cell expressing the PFP exhibits an increase in expression of CD155 compared to a cell not expressing the PFP.
53. The composition of any one of the preceding embodiments, wherein a cell expressing the PFP exhibits an increase in expression of CD112 compared to a cell not expressing the PFP.
54. The composition of any one of the preceding embodiments, wherein a cell expressing the PFP exhibits an increase in expression of PDL1 compared to a cell not expressing the PFP.
55. The composition of any one of the preceding embodiments, wherein a cell expressing the PFP exhibits an increase in expression of B7-DC compared to a cell not expressing the PFP.
56. The composition of any one of the preceding embodiments, wherein a cell expressing the PFP exhibits an increase in respiratory burst compared to a cell not expressing the PFP.
57. The composition of any one of the preceding embodiments, wherein a cell expressing the PFP exhibits an increase in ROS production compared to a cell not expressing the PFP.
58. The composition of any one of the preceding embodiments, wherein a cell expressing the PFP exhibits an increase in iNOS production compared to a cell not expressing the PFP.
59. The composition of any one of the preceding embodiments, wherein a cell expressing the PFP exhibits an increase in iNOS production compared to a cell not expressing the PFP.
60. The composition of any one of the preceding embodiments, wherein a cell expressing the PFP exhibits an increase in extra-cellular vesicle production compared to a cell not expressing the PFP.
61. The composition of any one of the preceding embodiments, wherein a cell expressing the PFP exhibits a increase in trogocytosis with a target cell expressing the antigen compared to a cell not expressing the PFP.
62. The composition of any one of the preceding embodiments, wherein a cell expressing the PFP exhibits an increase in resistance to CD47 mediated inhibition of phagocytosis compared to a cell not expressing the PFP.
63. The composition of any one of the preceding embodiments, wherein a cell expressing the PFP exhibits an increase in resistance to LILRB1 mediated inhibition of phagocytosis compared to a cell not expressing the PFP.
64. The composition of any one of the preceding embodiments, wherein the intracellular domain comprises a Rac inhibition domain, a Cdc42 inhibition domain or a GTPase inhibition domain.
65. The composition of embodiment 64, wherein the Rac inhibition domain, the Cdc42 inhibition domain or the GTPase inhibition domain inhibits Rac, Cdc42 or GTPase at a phagocytic cup of a cell expressing the PFP.
66. The composition of any one of the preceding embodiments, wherein the intracellular domain comprises an F-actin disassembly activation domain, a ARHGAP12 activation domain, a ARHGAP25 activation domain or a SH3BP1 activation domain 67. The composition of any one of the preceding embodiments, wherein a cell expressing the PFP exhibits an increase in phosphatidylinositol 3,4,5-trisphosphate production.
68. The composition of any one of the preceding embodiments, wherein the extracellular domain comprises an Ig binding domain.
69. The composition of any one of the preceding embodiments, wherein the extracellular domain comprises an IgA, IgD, IgE, IgG, IgM, FcγRI, FcγRIIA, FcγRIIB, FcγRIIC, FcγRIIIA, FcγRIIIB, FcRn, TRIM21, FcRL5 binding domain.
70. The composition of any one of the preceding embodiments, wherein the extracellular domain comprises an FcR extracellular domain.

71. The composition of any one of the preceding embodiments, wherein the extracellular domain comprises an FcR-alpha, FcR-beta, FcR-Epsilon or FcR-gamma extracellular domain.
72. The composition of any one of the preceding embodiments, wherein the extracellular domain comprises an FcαR (FCAR) extracellular domain.
73. The composition of any one of the preceding embodiments, wherein the extracellular domain comprises an FcR-beta extracellular domain.
74. The composition of any one of the preceding embodiments, wherein the extracellular domain comprises an FcεR (FCER1A) extracellular domain.
75. The composition of any one of the preceding embodiments, wherein the extracellular domain comprises an FcγR (FDGR1A, FCGR2A, FCGR2B, FCGR2C, FCGR3A, FCGR3B) extracellular domain.
76. The composition of any one of the preceding embodiments, wherein the extracellular domain comprises an integrin domain.
77. The composition of any one of the preceding embodiments, wherein the extracellular domain comprises one or more integrin α1, α2, αIIb, α3, α4, α5, α6, α7, α8, α9, α10, α11, αD, αE, αL, αM, αV, αX, β1, β2, β3, β4, β5, β6, β7, or β8 domains.
78. The composition of any one of the preceding embodiments, wherein the intracellular domain comprises a CD47 inhibition domain.
79. The composition of any one of the preceding embodiments, wherein the PSR subunit further comprises an extracellular domain operatively clinked to the transmembrane domain and the extracellular antigen binding domain.
80. The composition of embodiment 79, wherein the extracellular domain further comprises an extracellular domain of a receptor, a hinge, a spacer or a linker.
81. The composition of embodiment 80, wherein the extracellular domain comprises an extracellular portion of a PSR.
82. The composition of embodiment 81, wherein the extracellular portion of the PSR is derived from the same PSR as the PSR intracellular signaling domain.
83. The composition of any one of the embodiments 79-82, wherein the extracellular domain comprises an extracellular domain of a scavenger receptor or an immunoglobulin domain.
84. The composition of embodiment 83, wherein the immunoglobulin domain comprises an extracellular domain of an immunoglobulin or an immunoglobulin hinge region.
85. The composition of any one of the embodiments 79-84, wherein the extracellular domain comprises a phagocytic engulfment marker.
86. The composition of any one of the embodiments 79-85, wherein the extracellular domain comprises a structure capable of multimeric assembly.
87. The composition of any one of the embodiments 79-86, wherein the extracellular domain comprises a scaffold for multimerization.
88. The composition of any one of the preceding embodiments, wherein the extracellular domain is at least 10, 20, 30, 40, 50, 60, 70, 80, 90, 100, 150, 200, 300, 300, 400, or 500 amino acids in length.
89. The composition of any one of the preceding embodiments, wherein the extracellular domain is at most 500, 400, 300, 200, or 100 amino acids in length.
90. The composition of any one of the preceding embodiments, wherein the extracellular antigen binding domain specifically binds to the antigen of a target cell.
91. The composition of any one of the preceding embodiments, wherein the extracellular antigen binding domain comprises an antibody domain.
92. The composition of any one of the preceding embodiments, wherein the extracellular antigen binding domain comprises a receptor domain, antibody domain, wherein the antibody domain comprises a functional antibody fragment, a single chain variable fragment (scFv), an Fab, a single-domain antibody (sdAb), a nanobody, a VH domain, a VL domain, a VNAR domain, a VI-IH domain, a bispecific antibody, a diabody, or a functional fragment or a combination thereof.
93. The composition of any one of any one of the preceding embodiments, wherein the extracellular antigen binding domain comprises a ligand, an extracellular domain of a receptor or an adaptor.
94. The composition of any one of the preceding embodiments, wherein the extracellular antigen binding domain comprises a single extracellular antigen binding domain that is specific for a single antigen.
95. The composition of any one of any one of the preceding embodiments, wherein the extracellular antigen binding domain comprises at least two extracellular antigen binding domains, wherein each of the at least two extracellular antigen binding domains is specific for a different antigen.
96. The composition of any one of the preceding embodiments, wherein the antigen is a cancer antigen or a pathogenic antigen or an autoimmune antigen.
97. The composition of any one of the preceding embodiments, wherein the antigen comprises a viral antigen.
98. The composition of any one of the preceding embodiments, wherein the antigen is a T-lymphocyte antigen.
99. The composition of any one of the preceding embodiments, wherein the antigen is an extracellular antigen.
100. The composition of any one of the preceding embodiments, wherein the antigen is an intracellular antigen.
101. The composition of any one of the preceding embodiments, wherein the antigen is selected from the group consisting of Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), Mesothelin, EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFR-beta, SSEA-4, EGFR, NCAM, prostase, PAP, ELF2M, GM3, TEM7R, CLDN6, TSHR, GPRCSD, ALK, IGLL1 and combinations thereof
102. The composition of any one of the preceding embodiments, wherein the antigen is selected from the group consisting of CD2, CD3, CD4, CD5, CD7, CCR4, CD8, CD30, CD45, CD56.

103. The composition of any one of the preceding embodiments, wherein the antigen is an ovarian cancer antigen or a T lymphoma antigen.
104. The composition of any one of the preceding embodiments, wherein the antigen is an integrin receptor.
105. The composition of any one of the preceding embodiments, wherein the antigen is an integrin receptor selected from the group consisting of α1, α2, αIIb, α3, α4, α5, α6, α7, α8, α9, α10, α11, αD, αE, αL, αM, αV, αX, β1, β2, β3, β4, β5, β6, β7, and 138.
106. The composition of any one of the preceding embodiments, wherein the antigen comprises 2 or more antigens.
107. The composition of any one of the preceding embodiments, wherein the transmembrane domain and the extracellular antigen binding domain is operatively linked through a linker.
108. The composition of any one of the preceding embodiments, wherein the transmembrane domain and the extracellular antigen binding domain is operatively linked through a linker such as the hinge region of CD8a, IgG1 or IgG4.
109. The composition of any one of the preceding embodiments, wherein the extracellular domain comprises a multimerization scaffold.
110. The composition of any one of the preceding embodiments, wherein the transmembrane domain comprises an FcR transmembrane domain.
111. The composition of any one of the preceding embodiments, wherein the transmembrane domain comprises an FcR-ε with no more than 20, 10 or 5 modifications transmembrane domain.
112. The composition of any one of the preceding embodiments, wherein the transmembrane domain comprises a transmembrane domain from a syntaxin such as syntaxin 3 or syntaxin 4 or syntaxin 5.
113. The composition of any one of the preceding embodiments, wherein the transmembrane domain oligomerizes with a transmembrane domain of an endogenous receptor when the PFP is expressed in a cell.
114. The composition of any one of the preceding embodiments, wherein the transmembrane domain oligomerizes with a transmembrane domain of an exogenous receptor when the PFP is expressed in a cell.
115. The composition of any one of the preceding embodiments, wherein the transmembrane domain dimerizes with a transmembrane domain of an endogenous receptor when the PFP is expressed in a cell.
116. The composition of any one of the preceding embodiments, wherein the transmembrane domain dimerizes with a transmembrane domain of an exogenous receptor when the PFP is expressed in a cell.
117. The composition of any one of the preceding embodiments, wherein the transmembrane domain is derived from a protein that is different than the protein from which the intracellular signaling domain is derived.
118. The composition of any one of the preceding embodiments, wherein the transmembrane domain is derived from a protein that is different than the protein from which the extracellular domain is derived.
119. The composition of any one of the preceding embodiments, wherein the transmembrane domain comprises a transmembrane domain of a phagocytic receptor.
120. The composition of any one of the preceding embodiments, wherein the transmembrane domain and the extracellular domain are derived from the same protein.
121. The composition of any one of the preceding embodiments, wherein the transmembrane domain is derived from the same protein as the intracellular signaling domain.
122. The composition of any one of the preceding embodiments, wherein the recombinant nucleic acid encodes a DAP12 recruitment domain.
123. The composition of any one of the preceding embodiments, wherein the transmembrane domain comprises a transmembrane domain that oligomerizes with DAP12.
124. The composition of any one of the preceding embodiments, wherein the transmembrane domain is at least 12, 13, 14, 15, 16, 17, 18, 19, 20, 21, 22, 23, 24, 25, 26, 27, 28, 29, 30, 31 or 32 amino acids in length.
125. The composition of any one of the preceding embodiments, wherein the transmembrane domain is at most 12, 13, 14, 15, 16, 17, 18, 19, 20, 21, 22, 23, 24, 25, 26, 27, 28, 29, 30, 31 or 32 amino acids in length.
126. The composition of any one of the preceding embodiments, wherein the intracellular domain comprises a phosphatase inhibition domain.
127. The composition of any one of the preceding embodiments, wherein the intracellular domain comprises an ARP2/3 inhibition domain.
128. The composition of any one of the preceding embodiments, wherein the intracellular domain comprises at least one ITAM domain.
129. The composition of any one of the preceding embodiments, wherein the intracellular domain comprises at least 1, 2, 3, 4, 5, 6, 7, 8, 9, or 10 ITAM domains.
130. The composition of any one of the preceding embodiments, wherein the intracellular domain further comprises at least one ITAM domain.
131. The composition of any one of the preceding embodiments, wherein the intracellular domain further comprises at least one ITAM domain select from a group CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto.
132. The composition of embodiment 129, wherein the at least one ITAM domain comprises a Src-family kinase phosphorylation site.
133. The composition of embodiment 129, wherein the at least one ITAM domain comprises a Syk recruitment domain.
134. The composition of any one of the preceding embodiments, wherein the intracellular domain comprises a F-actin depolymerization activation domain.
135. The composition of any one of the preceding embodiments, wherein the intracellular domain lacks enzymatic activity.
136. The composition of any one of the preceding embodiments, wherein the intracellular domain does not comprise a domain derived from a CD3 zeta intracellular domain.
137. The composition of any one of the preceding embodiments, wherein the intracellular domain comprises a CD47 inhibition domain.

138. The composition of any one of the preceding embodiments, wherein the intracellular signaling domain comprises a domain that activate integrin such as the intracellular region of PSGL-1.
139. The composition of any one of the preceding embodiments, wherein the intracellular signaling domain comprises a domain that activate Rap1 GTPase, such as that from EPAC and C3G.
140. The composition of any one of the preceding embodiments, wherein the intracellular signaling domain are from paxillin.
141. The composition of any one of the preceding embodiments, wherein the intracellular signaling domain activates focal adhesion kinase.
142. The composition of any one of the preceding embodiments, wherein the intracellular signaling domain is derived from a single phagocytic receptor.
143. The composition of any one of the preceding embodiments, wherein the intracellular signaling domain is derived from a single scavenger receptor.
144. The composition of any one of the preceding embodiments, wherein the intracellular domain further comprises a phagocytosis enhancing domain.
145. The composition of any one of the preceding embodiments, wherein the intracellular domain comprises a pro-inflammatory signaling domain.
146. The composition of embodiment 145, wherein the pro-inflammatory signaling domain comprises a kinase activation domain or a kinase binding domain.
147. The composition of embodiment 145 or 146, wherein the pro-inflammatory signaling domain comprises an IL-1 signaling cascade activation domain.
148. The composition of any one of embodiments 145-147, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, an NLRP family member, NLRP1-14, NOD1, NOD2, Pyrin, AIM2, NLRC4, FCGR3A, FCERIG, CD40, a caspase domain or a pro-caspase binding domain or any combination thereof
149. The composition of any one of the preceding embodiments, wherein the PFP does not comprise a full length intracellular signaling domain.
150. The composition of any one of the preceding embodiments, wherein the intracellular domain is at least 5, 10, 20, 30, 40, 50, 60, 70, 80, 90, 100, 150, 200, 300, 300, 400, or 500 amino acids in length.
151. The composition of any one of the preceding embodiments, wherein the intracellular domain is at most 10, 20, 30, 40, 50, 60, 70, 80, 90, 100, 150, 200, 300, 300, 400, or 500 amino acids in length.
152. The composition of any one of the preceding embodiments, wherein the recombinant nucleic acid encodes an FcR alpha chain extracellular domain, an FcR alpha chain transmembrane domain and/or an FcR alpha chain intracellular domain.
153. The composition of any one of the preceding embodiments, wherein the recombinant nucleic acid encodes an FcR beta chain extracellular domain, an FcR beta chain transmembrane domain and/or an FcR beta chain intracellular domain.
154. The composition of embodiment 152 or 153, wherein the FcR alpha chain or the FcR beta chain forms a complex with FcR-gamma when expressed in a cell.
155. The composition of embodiment 154, wherein the FcR alpha chain or FcR beta chain forms a complex with endogenous FcR-gamma when expressed in a cell.
156. The composition of any one of embodiments 152-155, wherein the FcR alpha chain or the FcR beta chain does not incorporate into a cell membrane of a cell that does not express FcR gamma.
157. The composition of any one of embodiments 152-156, wherein the PFP does not comprise an FcR alpha chain intracellular signaling domain.
158. The composition of any one of embodiments 152-157, wherein the PFP does not comprise an FcR beta chain intracellular signaling domain.
159. The composition of any one of the preceding embodiments, wherein the recombinant nucleic acid encodes a TREM extracellular domain, a TREM transmembrane domain and/or a TREM intracellular domain.
160. The composition of embodiment 159, wherein the TREM is TREM1, TREM 2 or TREM 3.
161. The composition of any one of the preceding embodiments, wherein the recombinant nucleic acid comprises a sequence encoding coding a pro-inflammatory polypeptide.
162. The composition of any one of the preceding embodiments, wherein the composition further comprises a pro-inflammatory polypeptide.
163. The composition of embodiment 162, wherein the pro-inflammatory polypeptide is a chemokine, cytokine and nucleotides.
164. The composition of embodiment 163, wherein the chemokine is selected from the group consisting of IL-1, IL3, IL5, IL-6, i18, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon.
165. The composition of embodiment 163, wherein the cytokine is selected from the group consisting of IL-1, IL3, IL5, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon.
166. The composition of embodiment 163, wherein the nucleotide is selected from ATP, ADP, UTP, UDP, and/or UDP-glucose.
167. The composition of any one of the preceding embodiments, wherein the recombinant nucleic acid comprises a homeostatic regulator of inflammation.
168. The composition of embodiment 167, wherein the homeostatic regulator of inflammation is a sequence in an untranslated region (UTR) of an mRNA.
169. The composition of embodiment 168, wherein the sequence in the UTR is a sequence that binds to an RNA binding protein.
170. The composition of embodiment 168 or 169, wherein translation is inhibited or prevented upon binding of the RNA binding protein to the sequence in an untranslated region (UTR).
171. The composition of embodiment 169 or 170, wherein the sequence in the UTR comprises a consensus sequence of WWWU(AUUUA)UUUW (SEQ ID NO: 23), wherein W is A or U.
172. The composition of any one of the preceding embodiments, wherein the recombinant nucleic acid is expressed on a bicistronic vector.
173. The composition of any one of the preceding embodiments, wherein the target cell is a mammalian cell.
174. The composition of any one of the preceding embodiments, wherein the target cell is a human cell.
175. The composition of any one of the preceding embodiments, wherein the target cell comprises a cell infected with a pathogen.

176. The composition of any one of the preceding embodiments, wherein the target cell is a cancer cell.
177. The composition of any one of the preceding embodiments, wherein the target cell is a cancer cell that is a lymphocyte.
178. The composition of any one of the preceding embodiments, wherein the target cell is a cancer cell that is an ovarian cancer cell.
179. The composition of any one of the preceding embodiments, wherein the target cell is a cancer cell that is an ovarian pancreatic cell.
180. The composition of any one of the preceding embodiments, wherein the target cell is a cancer cell that is an glioblastoma cell.
181. The composition of any one of the preceding embodiments, wherein the recombinant nucleic acid is DNA.
182. The composition of any one of the preceding embodiments, wherein the recombinant nucleic acid is RNA.
183. The composition of any one of the preceding embodiments, wherein the recombinant nucleic acid is mRNA.
184. The composition of any one of the preceding embodiments, wherein the recombinant nucleic acid is a circRNA.
185. The composition of any one of the preceding embodiments, wherein the recombinant nucleic acid is a tRNA.
186. The composition of any one of the preceding embodiments, wherein the recombinant nucleic acid is a microRNA.
187. A vector comprising the composition of any one of embodiments 1-186.
188. The vector of embodiment 187, wherein the vector is viral vector.
189. The vector of embodiment 188, wherein the viral vector is retroviral vector or a lentiviral vector.
190. The vector of any one of embodiments 187-189, wherein the vector further comprises a promoter operably linked to at least one nucleic acid sequence encoding one or more polypeptides.
191. The vector of any one of embodiments 187-190, wherein the vector is polycistronic.
192. The vector of embodiment 190 or 191, wherein each of the at least one nucleic acid sequence is operably linked to a separate promoter.
193. The vector of any one of embodiments 187-192, wherein the vector further comprises one or more internal ribosome entry sites (IRESs).
194. The vector of any one of embodiments 187-192, wherein the vector further comprises a 5'UTR and/or a 3'UTR flanking the at least one nucleic acid sequence encoding one or more polypeptides.
195. The vector of any one of embodiments 187-192, wherein the vector further comprises one or more regulatory regions.
196. A polypeptide encoded by the recombinant nucleic acid of the composition of any one of embodiments 1-186.
197. A cell comprising the composition of any one of embodiments 1-186, the vector of any one of embodiments 187-195 or the polypeptide of embodiment 196.
198. The cell of embodiment 197, wherein the cell is a phagocytic cell.
199. The cell of embodiment 197 or 198, wherein the cell is a stem cell derived cell, myeloid cell, macrophage, a dendritic cell, lymphocyte, mast cell, monocyte, neutrophil, microglia, or an astrocyte.
200. The cell of any one of embodiments 197-199, wherein the cell is an autologous cell.
201. The cell of any one of embodiments 197-199, wherein the cell is an allogeneic cell.
202. The cell of any one of embodiments 197-201, wherein the cell is an M1 macrophage cell.
203. The cell of any one of embodiments 197-201, wherein the cell is an M2 macrophage cell.
204. A pharmaceutical composition comprising
(a) the composition of any one of embodiments 1-186, the vector of any one of embodiments 187-195, the polypeptide of embodiment 196 or the cell of any one of embodiments 197-203; and
(b) a pharmaceutically acceptable excipient.
205. The pharmaceutical composition of embodiment 204, further comprising an additional therapeutic agent.
206. The pharmaceutical composition of embodiment 204 or 205, wherein the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof.
207. The pharmaceutical composition of any one of embodiments 204-206, wherein the pharmaceutically acceptable excipient comprises serum free media, a lipid, or a nanoparticle.
208. A method of treating a disease in a subject in need thereof comprising administering to the subject the pharmaceutical composition of any one of embodiments 204-207.
209. The method of embodiment 208, wherein the disease is cancer.
210. The method of embodiment 209, wherein the cancer is a solid cancer.
211. The method of embodiment 210, wherein the solid cancer is selected from the group consisting of ovarian cancer, suitable cancers include ovarian cancer, renal cancer, breast cancer, prostate cancer, liver cancer, brain cancer, lymphoma, leukemia, skin cancer, pancreatic cancer, colorectal cancer, lung cancer
212. The method of embodiment 209, wherein the cancer is a liquid cancer.
213. The method of embodiment 212, wherein the liquid cancer is a leukemia or a lymphoma.
214, The method of embodiment 212, wherein the liquid cancer is a T cell lymphoma.
215. The method of embodiment 208, wherein the disease is a T cell malignancy.
216. The method of any one of embodiments 208-215, wherein the method further comprises administering an additional therapeutic agent to the subject.
217. The method of embodiment 216, wherein the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof.

218. The method of any one of embodiments 208-217, wherein administering comprises infusing or injecting.
219. The method of any one of embodiments 208-218, wherein administering comprises administering directly to the solid cancer.
220. The method of any one of embodiments 208-219, wherein administering comprises a circRNA, mRNA, viral-, particle-, liposome-, or exosome-based delivery procedure.
221. The method of any one of embodiments 208-220, wherein a CD4+ T cell response or a CD8+ T cell response is elicited in the subject.
222. A method of preparing a cell, the method comprising contacting a cell with the composition of any one of embodiments 1-186, the vector of any one of embodiments 187-195 or the polypeptide of embodiment 196.
223. The method of embodiment 222, wherein contacting comprises transducing.
224. The method of embodiment 223, where transducing comprises chemical transfection, electroporation, nucleofection, or viral infection.
225. A method of preparing a pharmaceutical composition comprising contacting a lipid to the composition of any one of embodiments 1-186 or the vector of any one of embodiments 187-195.
226. The method of embodiment 225, where contacting comprises forming a lipid nanoparticle.
227. A method of preparing a pharmaceutical composition comprising contacting an antibody to the composition of any one of embodiments 1-186 or the vector of any one of embodiments 187-195.
228. The method of embodiment 225, where contacting comprises forming a lipid nanoparticle.

EXAMPLES

Example 1. Generation of Novel Phagocytic Receptors Fusion Proteins (PFP) Constructs In this section, an exemplary design for identification of useful PR and antigen binding domains for the generation of novel PFP is described. Briefly, a large number of potential candidate proteins are screened for enhanced phagocytic properties and their respective phagocytosis related intracellular signaling. The useful domains are then used for generation of novel PFPs. The screen can be divided in two parts: A. Screening for the PR domains; B. Screening for the extracellular antigen binding domains.

Screening for the PR Domains:

5,800 plasma membrane proteins are screened for their phagocytic potential. J774 macrophage cells are transiently transfected with the library of 5800 plasma proteins. High-throughput multiplex assays (ranging from 6-well plate assay set up to up to 384-well plate assay with robotic handling) are set up to evaluate various potential functions of the plasma membranes. Exemplary assays include, but are not limited to phagocytosis assay, cytokine production assay, inflammasome activation assay, and iNOS activation assay. Exemplary simplified methods are described in the following paragraphs. Variations of each method are also used and are understood by a skilled artisan. Variations of each method are also used and are understood by a skilled artisan. Exemplary intracellular signaling domains tested for include but are not limited to CD40-FcR; FcR-CD40; NLRP3; FcR-SH2-Procaspase; FcR-Myd88; FcR-IFN gamma R; FcR-TNFR1; FcR-TNFR2; FcR-AIM2; FcR-TRIFN; FcR-Procaspase; TR1FC; RIG1; MDA5; TBK; CD64; CD16A; CD89; FcR epsilon; SIRPbeta; (two consecutive intracellular domains are represented as hyphenated terms, for example, FcR-Myd88 refers to an intracellular domain comprising an FcR ICD domain as signaling domain 1; and an Myd88 ICD as signaling domain 2). The extracellular linker domains screened include but are not limited to CD64, CD16A, CD89, SIRPalpha, FcR epsilon, CD8 hinge. The transmembrane domains tested include but are not limited to CD8, CD64, CD16A, CD89, FcRepsilon, SIRPalpha.

Phagocytosis Assay:

Antigen-linked silica or polysterene beads ranging in diameters 1 nm, 5 nm or 10 nm were used for a screen of macrophages. Inert beads are coated in a supported lipid bilayer and the antigens are ligated to the lipid bilayer. J774 macrophage cell lines are prepared, each cell line expressing a cloned recombinant plasma membrane protein. The recombinant plasma membrane protein may also express a fluorescent tag. The cell lines are maintained and propagated in complete RPMI media with heat inactivated serum and antibiotics (Penicillin/Streptomycin). On the day of the assay, cells are plated at a density of $1\times10^{\wedge}6$ cells/ml per well in 6 well plates or in a relative proportion in 12 or 24 well plates, and incubated for 2-6 hours. The cells are then washed once in Phosphate Buffer Saline, and the beads are added in serum depleted or complement depleted nutrient media. Cells are visualized by light microscopy at 30 minutes and 2 hours after addition of the beads. Immunofluorescence reaction may be performed using tagged antibody, and fluorescent confocal microscopy is used to detect the interaction and co-localization of cellular proteins at engulfment. Confidence levels are determined by Kruskal-Wallis test with Dunn's multiple comparison correction.

In some examples, dye loaded tumor cells are fed to macrophage cell lines and phagocytosis is assessed by microscopy.

Cytokine Production:

Macrophage cell lines are cultured as above. In one assay, each J774 cell line expressing a plasma membrane protein is plated in multi-wells and challenged with antigen-linked beads and cytokine production was assayed by collecting the supernatants at 4 hours and 24 hours. Cytokines are assayed from the supernatant by ELISA. In another fraction, cells are collected at 4 and 24 hours after incubation with the beads and flow cytometry is performed for detection of cytokines. In each case, multiple cytokines are assayed in a multiplex format, which can be selected from: IL-1α, IL-1β, IL-6, IL-12, IL-23, TNF-α, GMCSF, CXCL1, CXCL3, CXCL9, CXCL-10, MIP1-α and MIP-2. Macrophage inflammatory cytokine array kit (R&D Systems) is used.

Intracellular signaling pathway for inflammatory gene and cytokine activation can be identified by western blot analysis for phosphorylation of MAP kinases, JNK, Akt signaling pathway, Interferon activation pathway including phosphorylation and activation of STAT-1.

Inflammasome activation assay: Activation of NLRP3 inflammasome is assayed by ELISA detection of increased IL-1 production and detection caspase-1 activation by western blot, detecting cleavage of procaspase to generate the shorter caspase. In a microwell plate multiplex setting, Caspase-Glo (Promega Corporation) is used for faster readout of Caspase 1 activation.

iNOS Activation Assay:

Activation of the oxidative burst potential is measured by iNOS activation and NO production using a fluorimetric assay NOS activity assay kit (AbCAM).

Cancer Cell Killing Assay:

Raji B cells are used as cancer antigen presenting cells. Raji cells are incubated with whole cell crude extract of cancer cells, and co-incubated with J774 macrophage cell lines. The macrophages can destroy the cells after 1 hour of infection, which can be detected by microscopy or detected by cell death assay.

Screening for High Affinity Antigen Binding Domains:

Cancer ligands are subjected to screening for antibody light chain and heavy chain variable domains to generate extracellular binding domains for the PFPs. Human full length antibodies or scFv libraries are screened. Also potential ligands are used for immunizing llama for development of novel immunoglobulin binding domains in llama, and preparation of single domain antibodies.

Figure 5A:
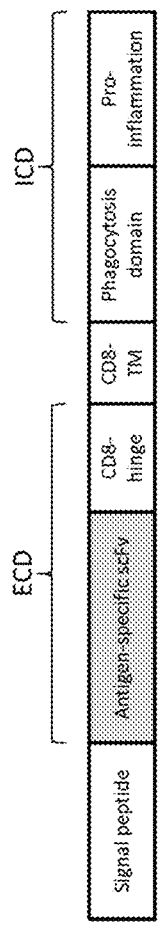
FIG. 5A is a schematic depicting an exemplary recombinant nucleic acid encoding a chimeric receptor fusion protein (M1-CAR) containing a signal peptide fused to an antigen-specific scFv that is fused to a CD8 hinge domain, a CD8 transmembrane domain and intracellular phagocytosis domain of and an intracellular pro-inflammation domain.
Figure 5B:
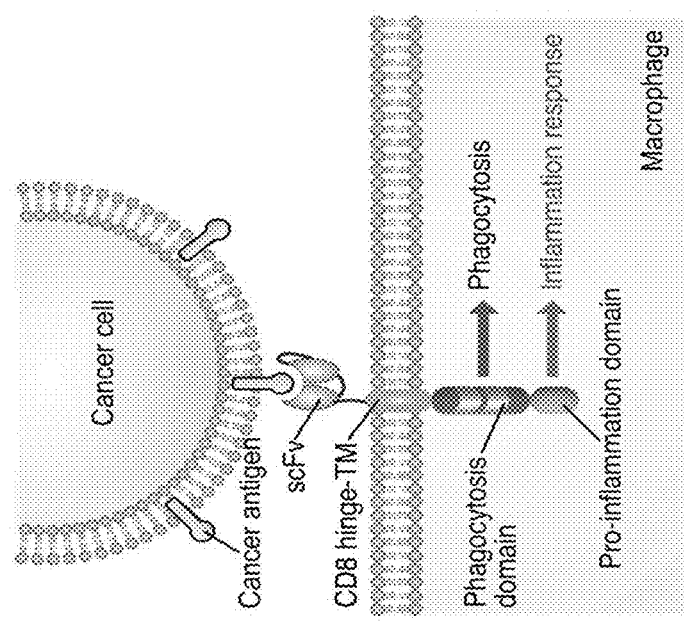
FIG. 5B is a schematic depicting the chimeric receptor fusion protein (M1-CAR) of FIG. 5A incorporated within a cell membrane of a macrophage cell. The depicted M1-CAR contains an scFv bound to a cancer antigen of a cancer cell.
Figure 5C:
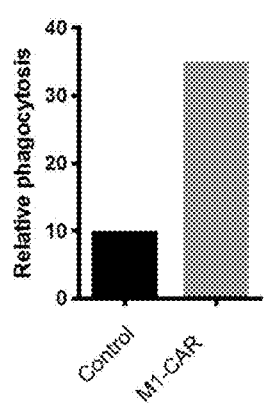
FIG. 5C is an exemplary graph depicting expected results of relative phagocytosis in human primary macrophage cells transduced with empty vector (control) or a vector encoding a chimeric receptor fusion protein (M1-CAR) co-cultured with dye loaded tumor cells. Phagocytosis is quantified using flow cytometry.
Figure 5D:
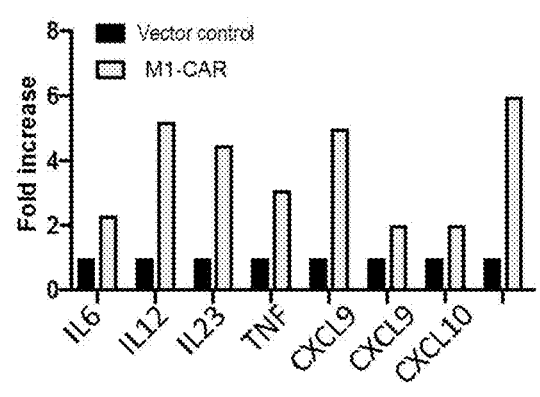
FIG. 5D is an exemplary graph depicting expected results of fold increase in production of the depicted cytokines in cells transduced with a vector control or a vector encoding a chimeric receptor fusion protein (M1-CAR).
Figure 5E:
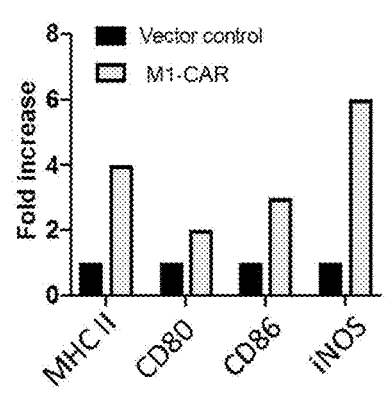
FIG. 5E is an exemplary graph depicting expected results of fold increase in production of the depicted M1 markers in human primary macrophage cells transduced with a vector control or a vector encoding a chimeric receptor fusion protein (M1-CAR).
Figure 5F:
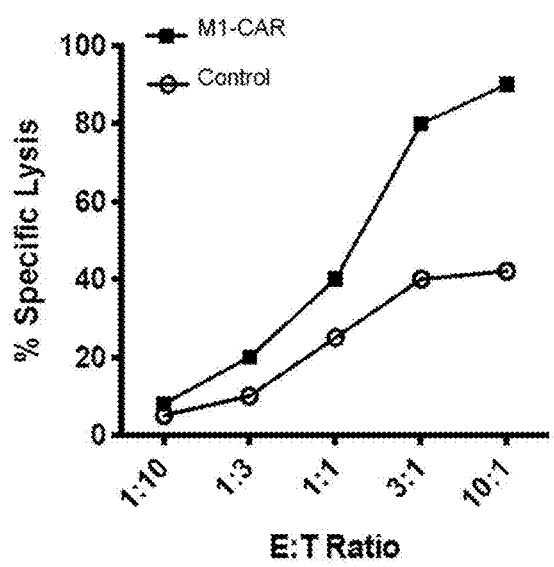
FIG. 5F is an exemplary graph depicting expected results of percent specific lysis of tumor cells when incubated in the presence of human primary macrophage cells (effector cells) transduced with empty vector (control) or a vector encoding a chimeric receptor fusion protein (M1-CAR) co-cultured with tumor cells (target cells) expressing luciferase at the indicated effector cell:target cell ratios (E:T ratio). Specific lysis is quantified using a luciferase assay.
Figure 5G:
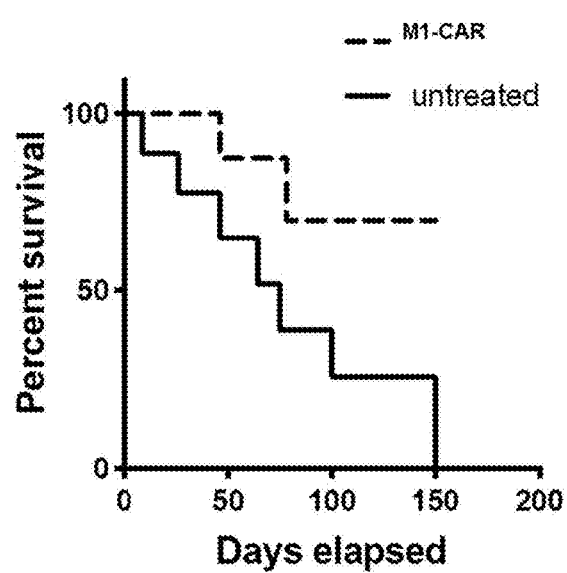
FIG. 5G is an exemplary graph depicting expected results of percent survival in a mouse xenograft tumor model after treatment with human primary macrophage cells transduced with empty vector (control) or a vector encoding a chimeric receptor fusion protein (M1-CAR).

Specific useful domains identified from the screens are then reverse transcribed, and cloned into lentiviral expression vectors to generate the chimeric PFP constructs. A recombinant nucleic acid for PFP can generated using one or more domains from the extracellular, TM and cytoplasmic regions of the highly phagocytic receptors generated from the screen. Briefly plasma membrane receptors showing high activators of pro-inflammatory cytokine production and inflammasome activation are identified. Bioinformatics studies are performed to identify functional domains including extracellular activation domains, transmembrane domains and intracellular signaling domains, for example, specific kinase activation sites, SH2 recruitment sites. These screened functional domains are then cloned in modular constructions for generating novel PFP. These are candidate PFPs, and each of these chimeric construct is tested for phagocytic enhancement and/or tumor cell killing in vitro and/or in vivo. Plasmid or lentiviral constructions of the designer PFPs are then prepared and tested in macrophage cells for cancer cell lysis.

Exemplary functional domain containing PFPs are described in the following sections.

Example 2. Generation of Recombinant PFP Having Scavenger Receptor ECD, TM and ICD (SR-CAR)

A chimeric antigen receptor (CAR) designed for the purpose of the present application is modular, having an extracellular target binding domain primarily comprising of an ScFv, or an Fab region or VHH domain, that can bind to a target, e.g. CD5, a short hinge, a transmembrane domain, and an intracellular domain comprising one or two or more signaling domains (FIGS. 2A-2C). Additionally, the extracellular domain can be designed to bind to a single or a multiple target (FIG. 3). An exemplary design of a phagocytic scavenger receptor is illustrated in FIGS. 4A and 4B. The recombinant nucleic acid encoding the PFP is constructed as follows: a signal peptide sequence which encodes for the membrane localization signal for the recombinant protein is placed upstream of the coding sequence of the extracellular antigen binding domain. Then the nucleic acid sequence encoding extracellular antigen binding scFv domain is synthesized and cloned into an expression vector, downstream of the signal peptide sequence. The PSR subunit is made up of the sequence encoding the extracellular domain, the TM domain and the intracellular domain of the scavenger receptor of choice is ligated at the 3'end of the scFv, and preferably with a linker peptide sequence in between the 3'end of the scFv and the 5'end of the scavenger receptor ECD. A linker peptide is a nucleotide sequence encoding the tetramer: GGGS, and optionally the linker is a sequence that has two or more repeats of the tetramer. The basic construct designs are shown in FIG. 2A-FIG. 4B shows the structural layout of the PFP. Once translated, the scavenger receptor TM domain is incorporated in the TM.

Lentiviral constructs of SR-CAR are prepared and purified for use in transduction studies.

Example 3. Expression and Functional Analysis of the Recombinant SR-CAR

To test the function of the PFP, human macrophages are transduced with pCMV-SRCAR using lipofectamine. In parallel, control cells are transfected with an empty vector. After stabilization of the cells for 48 hours, the cells are subjected to phagocytosis assay. FIG. 4C shows the expected result in an in vitro phagocytosis assay. Human primary macrophage transduced with control empty vector or SR-CAR are co-cultured with dye loaded tumor cells, and phagocytosis is quantified using flow cytometry. The cells with the SR CAR plasmid show increased phagocytosis over control cells.

FIG. 4D shows the expected result in an in vitro cell lysis assay. Human primary macrophage transduced with control vector or SR-CAR are co-cultured with tumor cells expressing luciferase at different E:T ratio, and specific lysis is quantified using luciferase assay.

FIG. 4E shows the expected result in a mouse xenograft model. On day 0, NSG mice were injected with tumor cells expressing luciferase. Mice are either untreated or injected with human primary macrophage transduced with SR-CAR, and survival curve is generated.

Example 4. Generation of Recombinant PFP Protein Having a Second Intracellular Domain-Inflammatory Response Domain (IR-CAR)

This example shows an exemplary PFP design with an extracellular scFv domain, a linker with a hinge, a CD8 transmembrane domain an intracellular phagocytic receptor domain, and additionally another intracellular inflammatory response (IR) domain from a pro-inflammatory protein (FIGS. 5A-5B). The recombinant nucleic acid encoding the PFP is constructed as follows: a signal peptide sequence which encodes for the membrane localization signal for the recombinant protein is placed upstream of the coding sequence of the extracellular antigen binding domain. Then the nucleic acid sequence encoding extracellular antigen binding scFv domain is synthesized and cloned into an expression vector, downstream of the signal peptide sequence. The PR subunit is made up of the sequence encoding an extracellular and transmembrane domain of CD8 receptor. The scFv and the CD8 region are connected by a hinge, contributed by the CD8 region proximal to the extracellular domain. The 3'end of the CD8 TM encoding region is ligated to the intracellular domain of a phagocytic receptor of choice. To the 3'end of the coding sequence of the intracellular phagocytic domain, the 5'end of the pro-inflammatory intracellular response domain is ligated.

For testing the recombinant construct is inserted in a Lentiviral expression vector, and purified for use in cell expression.

Example 5. Expression and Functional Analysis of Recombinant IR-CAR

Human primary macrophage transduced with control empty vector or M1-CAR are co-cultured with target tumor cells. FIG. 5C shows the expected result of relative phagocytoses of the dye loaded target tumor cells. FIG. 5D shows the expected result of expression of cytokines when M1-CAR macrophages are co-cultured with target tumor cells. Cytokine profiling with ELISA shows increased secretion of pro-inflammatory cytokines and chemokines compared to vector control. FIG. 5E shows expected result of flow cytometry of surface antigens (MHCII, CD80, CD86) shows an increase of M1 state marker expression compared with vector control, and similarly, iNOS expression (intracellular) was upregulated. FIGS. 5F and 5G indicate expected results

Example 6. Generation of Recombinant PFP Having Integrin Activation Domain (Intevin-CAR)

Figure 6A:
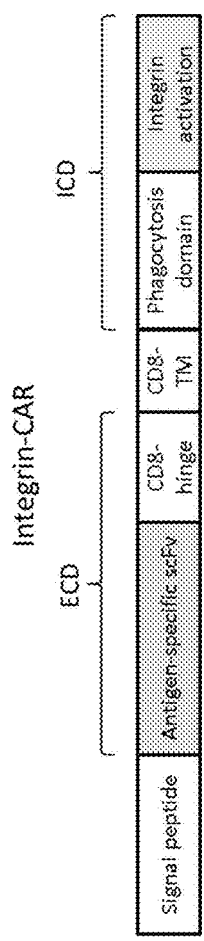
FIG. 6A is a schematic depicting an exemplary recombinant nucleic acid encoding a chimeric receptor fusion protein (Integrin-CAR) containing a signal peptide fused to an antigen-specific scFv that is fused to a CD8 hinge domain, a CD8 transmembrane domain and intracellular phagocytosis domain and an intracellular integration activation domain.
Figure 6B:
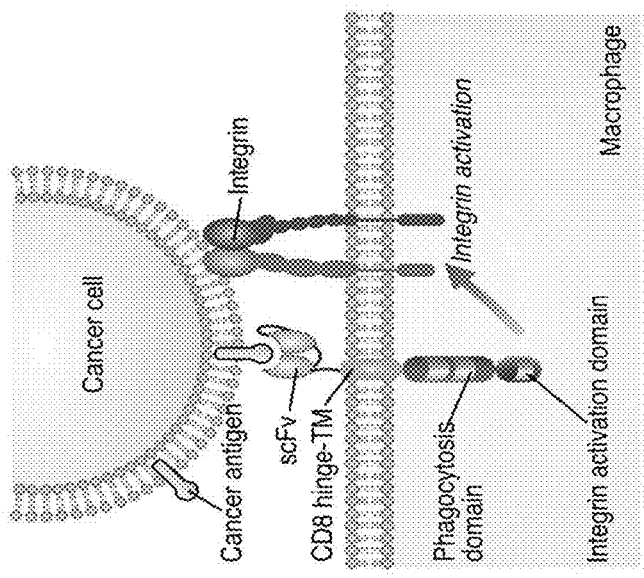
FIG. 6B is a schematic depicting the chimeric receptor fusion protein (Integrin-CAR) of FIG. 6A incorporated within a cell membrane of a macrophage cell. The depicted Integrin-CAR contains an scFv bound to a cancer antigen of a cancer cell.
Figure 6C:
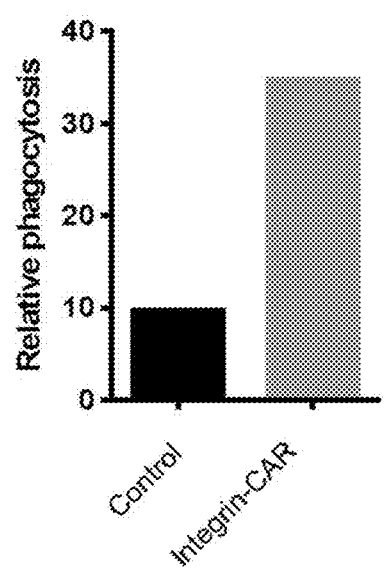
FIG. 6C is an exemplary graph depicting expected results of relative phagocytosis in human primary macrophage cells transduced with empty vector (control) or a vector encoding a chimeric receptor fusion protein (Integrin-CAR) co-cultured with dye loaded tumor cells. Phagocytosis is quantified using flow cytometry.
Figure 6D:
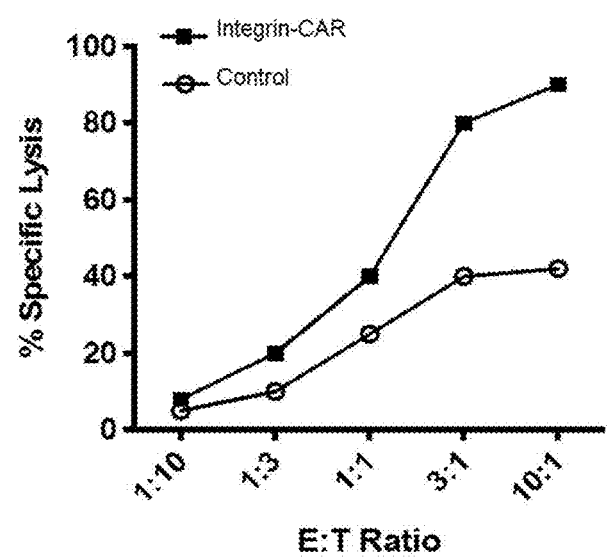
FIG. 6D is an exemplary graph depicting expected results of percent specific lysis of tumor cells when incubated in the presence of human primary macrophage cells (effector cells) transduced with empty vector (control) or a vector encoding a chimeric receptor fusion protein (Integrin-CAR) co-cultured with tumor cells (target cells) expressing luciferase at the indicated effector cell:target cell ratios (E:T ratio).
Figure 6E:
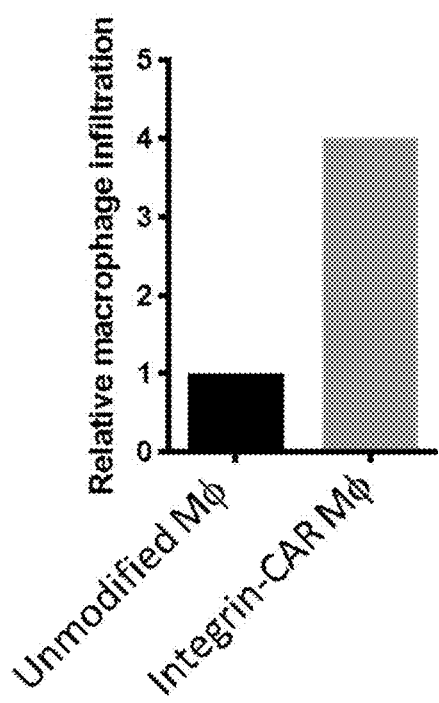
FIG. 6E is an exemplary graph depicting expected results of relative macrophage infiltration of human primary macrophage cells transduced with empty vector (control) or a vector encoding a chimeric receptor fusion protein (Integrin-CAR).
Figure 6F:
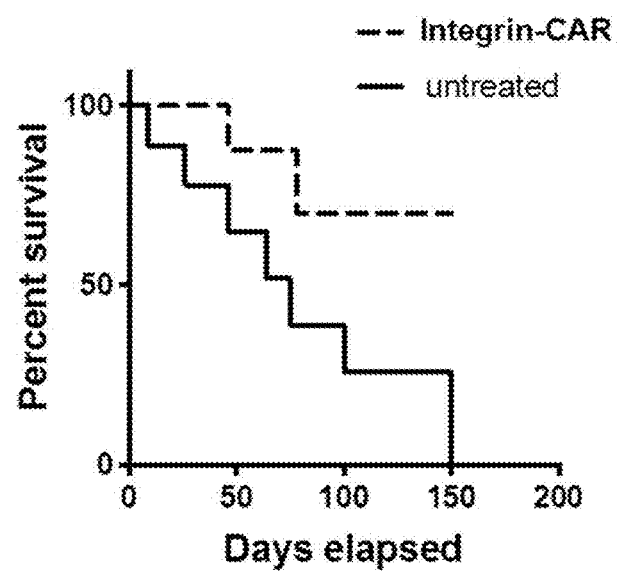
FIG. 6F is an exemplary graph depicting expected results of percent survival in a mouse xenograft tumor model after treatment with human primary macrophage cells transduced with empty vector (control) or a vector encoding a chimeric receptor fusion protein (Integrin-CAR).
Figure 7:
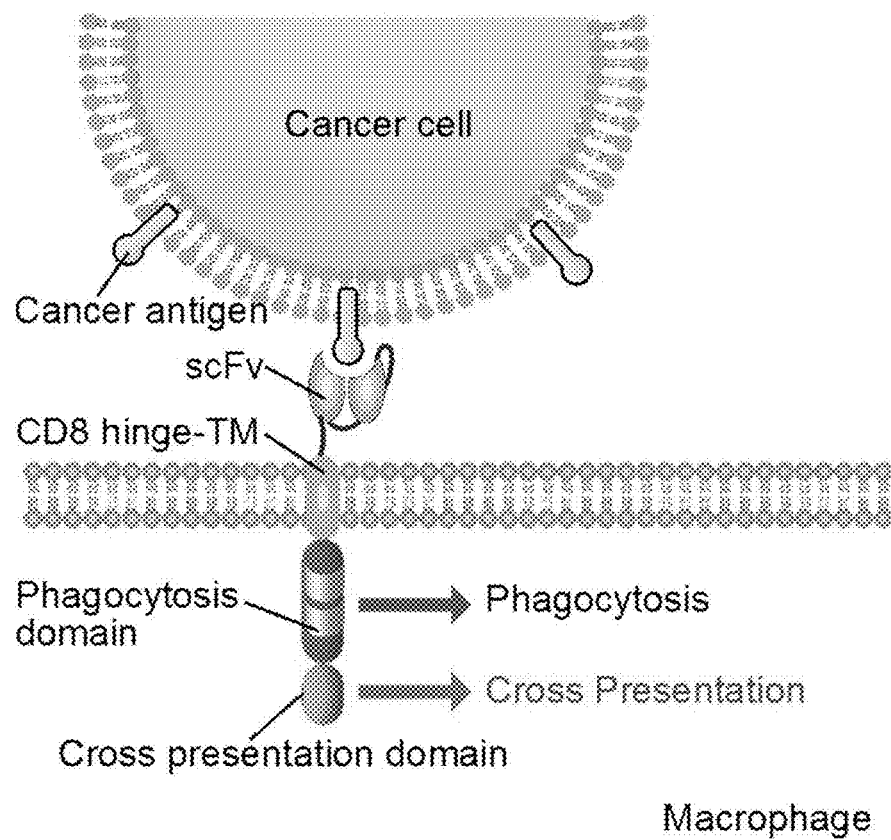
FIG. 7 is a schematic depicting the chimeric receptor fusion protein (cross presentation-CAR) incorporated within a cell membrane of a macrophage cell. The depicted cross presentation-CAR contains an scFv bound to a cancer antigen of a cancer cell that is fused to a CD8 hinge domain, a CD8 transmembrane domain, an intracellular phagocytosis domain and an intracellular cross presentation domain. Cross presentation-CARs may direct antigens to a cross presentation pathway.

This example shows an exemplary design with an extracellular scFv domain, a transmembrane domain and an intracellular phagocytic domain, and additionally an intracellular integrin activation domain (FIG. 6A, 6B). The recombinant nucleic acid encoding the PFP is constructed as follows: a signal peptide sequence which encodes for the membrane localization signal for the recombinant protein is placed upstream of the coding sequence of the extracellular antigen binding domain. Then the nucleic acid sequence encoding extracellular antigen binding scFv domain is synthesized and cloned into an expression vector, downstream of the signal peptide sequence. The PSR subunit is made up of the sequence encoding an extracellular and transmembrane domain of CD8 receptor. The scFv and the CD8 region are connected by a hinge, contributed by the CD8 region proximal to the extracellular domain. The 3'end of the CD8 TM encoding region is ligated to the phagocytosis domain of a phagocytic receptor of choice. To the 3'end of the coding sequence of the intracellular phagocytic domain, the 5'end of a P-selectin intracellular integrin activation domain is ligated. The basic design of the recombinant nucleic acid is shown in FIG. 5A. A diagrammatic depiction of the structural layout of the exemplary receptor is shown in FIG. 5B. FIG. 5B shows graphical representation of integrin activation, where integrins are endogenous, and form clusters upon activation. When expressed in macrophages, binding of scFv to tumor specific antigen leads to activation of phagocytosis signaling as well as activation of integrin. This leads to stronger phagocytosis as well as improved macrophage trafficking.

The construct is inserted in a lentiviral vector and purified for functional studies.

Example 7. Expression and Functional Analysis of the Recombinant Integrin-CAR Human primary macrophage transduced with control empty vector or integrin-CAR are co-cultured with target tumor cells. FIG. 5C shows expected results of increased phagocytosis by integrin-CAR transduced macrophages compared to control macrophages. FIG. 5D shows expected results of increased lysis of tumor cells by cells expressing integrin-CAR. FIG. 5E shows expected results of increased migration and tumor infiltration of integrin-CAR transduced macrophages compared to control macrophages. FIG. 5F shows expected survival curve in mouse xenograft model of a tumor after treatment with integrin-CAR transduced macrophages, or no treatment controls.

Example 8. Generation of Recombinant PFP Having an SREC-1 Cross Presentation Domain In this example, an exemplary design of a vector expressing the PFP, with an extracellular scFv domain, a transmembrane domain and an intracellular phagocytic domain, and additionally an signaling domain. FIG. 6A provides a schematic diagram of the intracellular signaling pathways involving SREC and antigen cross presentation. The recombinant nucleic acid encoding the PFP is constructed as follows: a signal peptide sequence which encodes for the membrane localization signal for the recombinant protein is placed upstream of the coding sequence of the extracellular antigen binding domain. Then the nucleic acid sequence encoding extracellular antigen binding scFv domain is synthesized and cloned into an expression vector, downstream of the signal peptide sequence. The PR subunit is made up of the sequence encoding an extracellular and transmembrane domain of phagocytic receptor. The 3'end of the TM encoding region is ligated to the phagocytosis domain of a phagocytic receptor. To the 3'end of the coding sequence of the intracellular phagocytic domain, the 5'end of the intracellular signaling domain for cross presentation is ligated. A diagrammatic depiction of the structural layout of the exemplary receptor is shown in FIG. 6B. FIGS. 6C-6F show expected functional characteristics as described earlier.

Example 9. Manufacturing Protocol for Macrophage Cell Preparation from a Subject Macrophage Isolation from PBMCs:
Peripheral blood mononuclear cells are separated from normal donor buffy coats by density centrifugation using Histopaque 1077 (Sigma). After washing, CD14+ monocytes are isolated from the mononuclear cell fraction using CliniMACS GMP grade CD14 microbeads and LS separation magnetic columns (Miltenyi Biotec). Briefly, cells are resuspended to appropriate concentration in PEA buffer (phosphate-buffered saline [PBS] plus 2.5 mmol/L ethylenediaminetetraacetic acid [EDTA] and human serum albumin [0.5% final volume of Alburex 20%, Octopharma]), incubated with CliniMACS CD14 beads per manufacturer's instructions, then washed and passed through a magnetized LS column. After washing, the purified monocytes are eluted from the demagnetized 0.117-column, washed and re-suspended in relevant medium for culture. Isolation of CD14+ cells from leukapheresis: PBMCs are collected by leukapheresis from cirrhotic donors who gave informed consent to participate in the study. Leukapheresis of peripheral blood for mononuclear cells (MNCs) is carried out using an Optia apheresis system by sterile collection. A standard collection program for MNC is used, processing 2.5 blood volumes. Isolation of CD14 cells is carried out using a GMP-compliant functionally closed system (CliniMACS Prodigy system, Miltenyi Biotec). Briefly, the leukapheresis product is sampled for cell count and an aliquot taken for pre-separation flow cytometry. The percentage of monocytes (CD14+) and absolute cell number are determined, and, if required, the volume is adjusted to meet the required criteria for selection ($<20 \times 10^9$ total white blood cells; $<400 \times 106$ white blood cells/mL; $<3.5 \times 109$ CD14 cells, volume 50-300 mL). CD14 cell isolation and separation is carried out using the CliniMACS Prodigy with CliniMACS CD14 microbeads (medical device class III), TS510 tubing set and LP-14 program. At the end of the process, the selected CD14+ positive monocytes are washed in PBS/EDTA buffer (CliniMACS buffer, Miltenyi) containing pharmaceutical grade 0.5% human albumin (Alburex), then re-suspended in TexMACS (or comparator) medium for culture.

Cell Count and Purity:
Cell counts of total MNCs and isolated monocyte fractions are performed using a Sysmex XP-300 automated analyzer (Sysmex). Assessment of macrophage numbers is carried out by flow cytometry with TruCount tubes (Becton Dickinson) to determine absolute cell number, as the Sysmex consistently underestimated the number of monocytes. The purity of the separation is assessed using flow cytometry (FACSCanto II, BD Biosciences) with a panel of antibodies against human leukocytes (CD45-VioBlue, CD15-FITC, CD14-PE, CD16-APC), and product quality is assessed by determining the amount of neutrophil contamination (CD45int, CD15pos).

Cell Culture—Development of Cultures with Healthy Donor Samples

Optimal culture medium for macrophage differentiation is investigated, and three candidates are tested using for the cell product. In addition, the effects of monocyte cryopreservation on deriving macrophages for therapeutic use is examined. Functional assays are conducted to quantify the phagocytic capacity of macrophages and their capacity for further polarization, and phagocytic potential as described elsewhere in the disclosure.

Full-Scale Process Validation with Subject Samples

Monocytes cultured from leukapheresis from Prodigy isolation are cultured at 2×10^6 monocytes per cm² and per mL in culture bags (MACS GMP differentiation bags, Miltenyi) with GMP-grade TexMACS (Miltenyi) and 100 ng/mL M-CSF. Monocytes are cultured with 100 ng/mL GMP-compliant recombinant human M-CSF (R&D Systems). Cells are cultured in a humidified atmosphere at 37° C., with 5% $CO_2$ for 7 days. A 50% volume media replenishment is carried out twice during culture (days 2 and 4) with 50% of the culture medium removed, then fed with fresh medium supplemented with 200 ng/mL M-CSF (to restore a final concentration of 100 ng/mL).

Cell Harvesting:

For normal donor-derived macrophages, cells are removed from the wells at day 7 using Cell Dissociation Buffer (Gibco, Thermo Fisher) and a pastette. Cells are resuspended in PEA buffer and counted, then approximately 106 cells per test are stained for flow cytometry. Leukapheresis-derived macrophages are removed from the culture bags at day 7 using PBS/EDTA buffer (CliniMACS buffer, Miltenyi) containing pharmaceutical grade 0.5% human albumin from serum (HAS; Alburex). Harvested cells are resuspended in excipient composed of two licensed products: 0.9% saline for infusion (Baxter) with 0.5% human albumin (Alburex).

Flow Cytometry Characterization:

Monocyte and macrophage cell surface marker expression is analyzed using either a FACSCanto II (BD Biosciences) or MACSQuant 10 (Miltenyi) flow cytometer. Approximately 20,000 events are acquired for each sample. Cell surface expression of leukocyte markers in freshly isolated and day 7 matured cells is carried out by incubating cells with specific antibodies (final dilution 1:100). Cells are incubated for 5 min with FcR block (Miltenyi) then incubated at 4° C. for 20 min with antibody cocktails. Cells are washed in PEA, and dead cell exclusion dye DRAQ7 (BioLegend) is added at 1:100. Cells are stained for a range of surface markers as follows: CD45-VioBlue, CD14-PE or CD14-PerCP-Vio700, CD163-FITC, CD169-PE and CD16-APC (all Miltenyi), CCR2-BV421, CD206-FITC, CXCR4-PE and CD115-APC (all BioLegend), and 25F9-APC and CD115-APC (eBioscience). Both monocytes and macrophages are gated to exclude debris, doublets and dead cells using forward and side scatter and DRAQ7 dead cell discriminator (BioLegend) and analyzed using FlowJo software (Tree Star). From the initial detailed phenotyping, a panel is developed as Release Criteria (CD45-VB/CD206-FITC/CD14-PE/25F9 APC/DRAQ7) that defined the development of a functional macrophage from monocytes. Macrophages are determined as having mean fluorescence intensity (MFI) five times higher than the level on day 0 monocytes for both 25F9 and CD206. A second panel is developed which assessed other markers as part of an Extended Panel, composed of CCR2-BV421/CD163-FITC/CD169-PE/CD14-PerCP-Vio700/CD16-APC/DRAQ7), but is not used as part of the Release Criteria for the cell product.

Both monocytes and macrophages from buffy coat CD14 cells are tested for phagocytic uptake using pHRodo beads, which fluoresce only when taken into acidic endosomes. Briefly, monocytes or macrophages are cultured with 1-2 uL of pHRodo *Escherichia coli* bioparticles (LifeTechnologies, Thermo Fisher) for 1 h, then the medium is taken off and cells washed to remove non-phagocytosed particles. Phagocytosis is assessed using an EVOS microscope (Thermo Fisher), images captured and cellular uptake of beads quantified using ImageJ software (NIH freeware). The capacity to polarize toward defined differentiated macrophages is examined by treating day 7 macrophages with interferon (IFN)-γ (50 ng/mL) or interleukin (IL)-4 (20 ng/mL) for 48 h to induce polarization to M1 or M2 phenotype (or M[IFNγ] versus M[IL-4], respectively). After 48 h, the cells are visualized by EVOS bright-field microscopy, then harvested and phenotyped as before. Further analysis is performed on the cytokine and growth factor secretion profile of macrophages after generation and in response to inflammatory stimuli. Macrophages are generated from healthy donor buffy coats as before, and either left untreated or stimulated with tumor necrosis factor (TNF)-α (50 ng/mL, Peprotech) and polyinosinic:polycytidylic acid (poly I:C, a viral homolog which binds TLR3, 1 g/mL, Sigma) to mimic the conditions present in the inflamed liver, or lipopolysaccharide (LPS, 100 ng/mL, Sigma) plus IFN-γ (50 IU/mL, Peprotech) to produce a maximal macrophage activation. Day 7 macrophages are incubated overnight and supernatants collected and spun down to remove debris, then stored at −80° C. until testing. Secretome analysis is performed using a 27-plex human cytokine kit and a 9-plex matrix metalloprotease kit run on a Magpix multiplex enzyme linked immunoassay plate reader (BioRad).

Product Stability:

Various excipients are tested during process development including PBS/EDTA buffer; PBS/EDTA buffer with 0.5% HAS (Alburex), 0.9% saline alone or saline with 0.5% HAS. The 0.9% saline (Baxter) with 0.5% HAS excipient is found to maintain optimal cell viability and phenotype (data not shown). The stability of the macrophages from cirrhotic donors after harvest is investigated in three process optimization runs, and a more limited range of time points assessed in the process validation runs (n=3). After harvest and re-suspension in excipient (0.9% saline for infusion, 0.5% human serum albumin), the bags are stored at ambient temperature (21-22° C.) and samples taken at 0, 2, 4, 6, 8, 12, 24, 30 and 48 h postharvest. The release criteria antibody panel is run on each sample, and viability and mean fold change from day 0 is measured from geometric MFI of 25F9 and CD206.

Statistical Analysis:

Results are expressed as mean±SD. The statistical significance of differences is assessed where possible with the unpaired two-tailed t-test using GraphPad Prism 6. Results are considered statistically significant when the P value is <0.05.

Example 10. CD5-FcR-PI3K PFP Construct

Figure 2A:
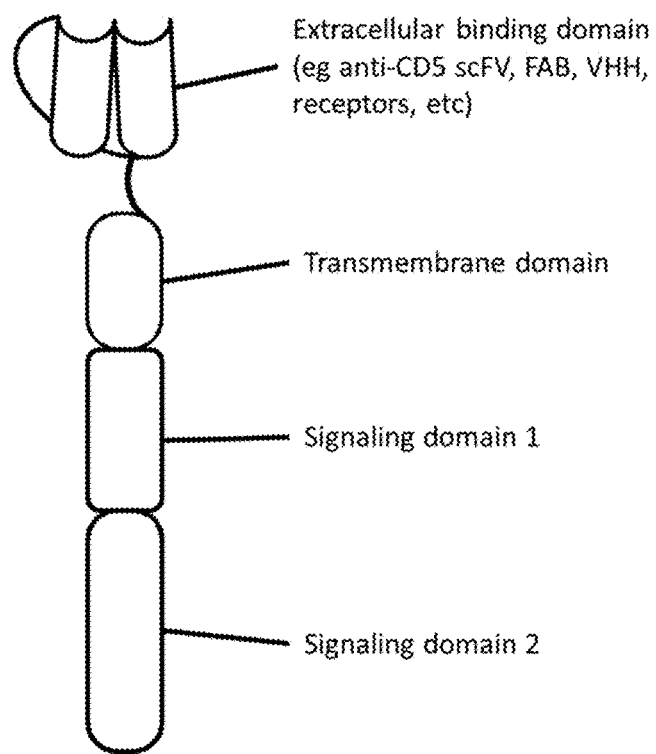
FIG. 2A depicts a schematic showing an exemplary phagocytic receptor fusion protein (PFP) containing an extracellular binding domain, a transmembrane domain, a first intracellular signaling domain and a second intracellular signaling domain.
Figure 2B:
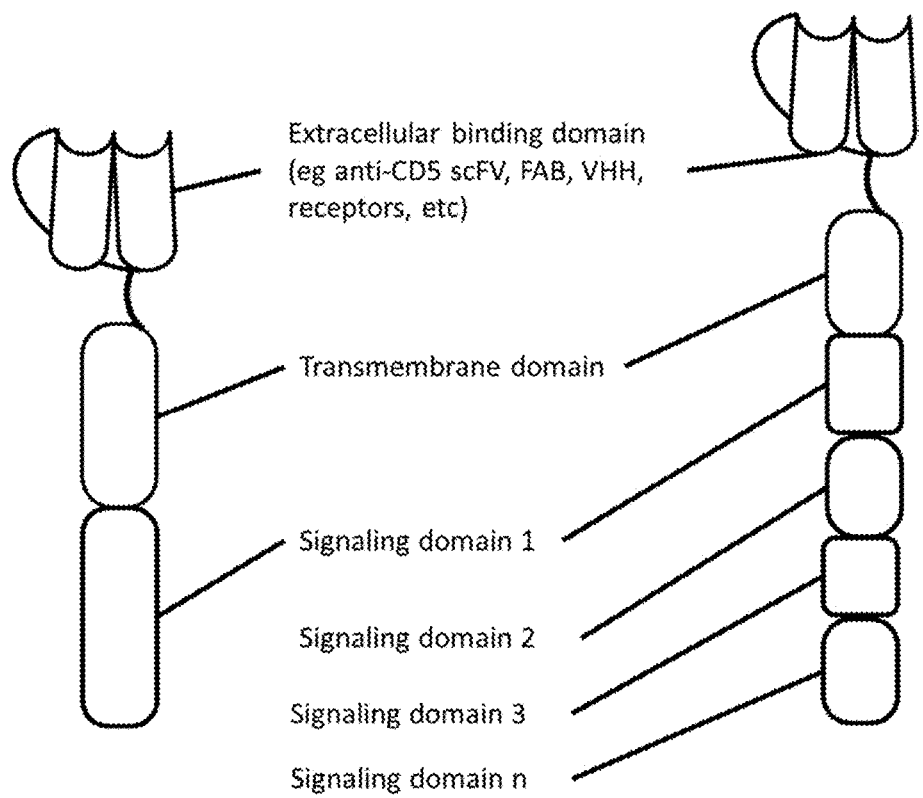
FIG. 2B depicts a schematic showing an exemplary phagocytic receptor fusion protein (PFP) containing an extracellular binding domain, a transmembrane domain, and an intracellular signaling domain (left), and a PFP containing an extracellular binding domain, a transmembrane domain, a first intracellular signaling domain, a second intracellular signaling domain, a third intracellular signaling domain, and one or more additional intracellular signaling domains.
Figure 2C:
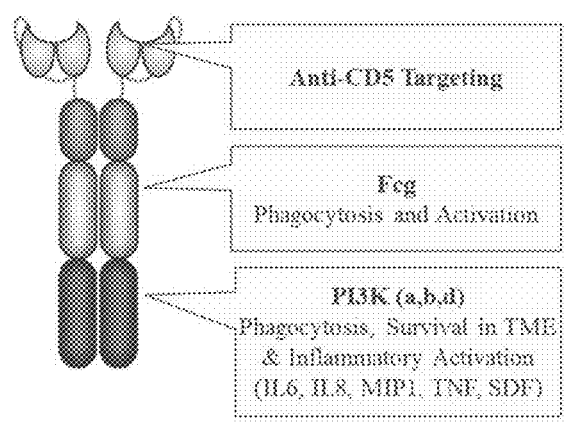
FIG. 2C depicts a schematic showing an exemplary phagocytic receptor fusion protein (PFP) dimer containing an anti-CD5 extracellular binding domain, a transmembrane domain, and an intracellular signaling domain containing an intracellular domain derived from FcRγ fused to a PI3K recruitment domain.
Figure 2D:
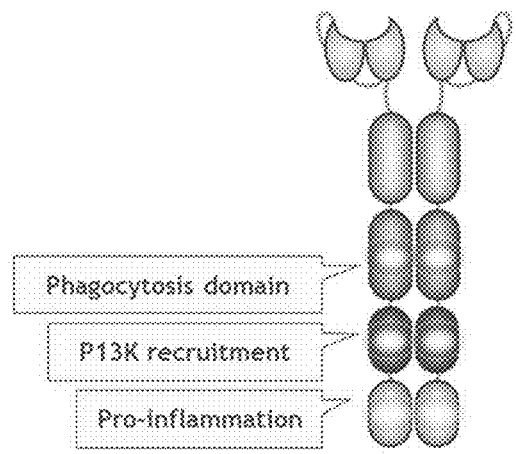
FIG. 2D depicts a schematic showing an exemplary phagocytic receptor fusion protein (PFP) dimer containing an extracellular antigen binding domain, a transmembrane domain, and an intracellular signaling domain containing a phagocytosis domain a PI3K recruitment domain and a pro-inflammation domain.
Figure 3:
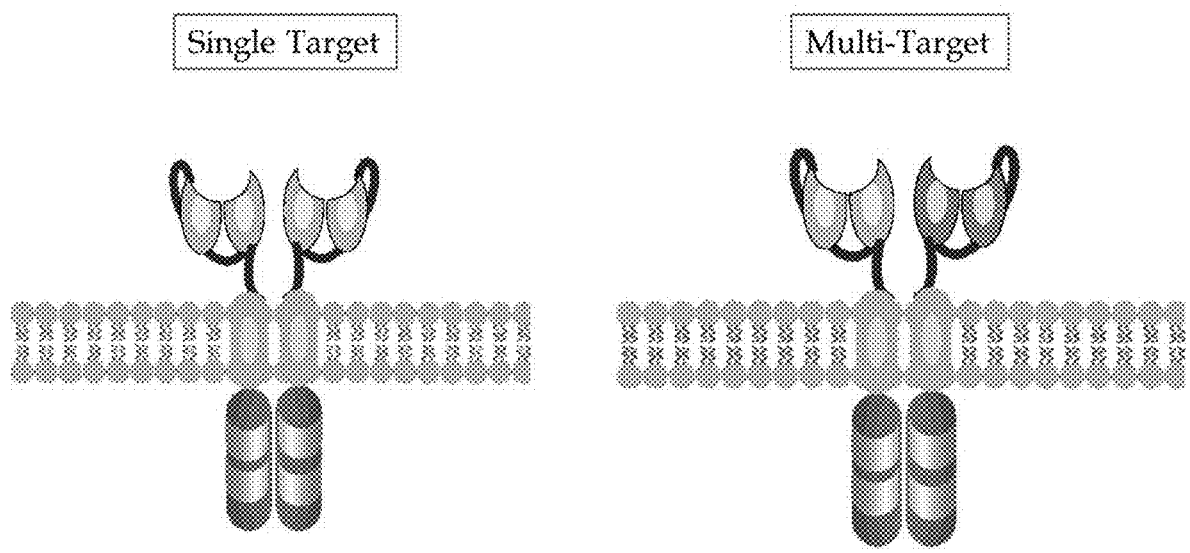
FIG. 3 is a schematic depicting an exemplary phagocytic receptor fusion protein (PFP) homodimer in which each subunit contains an extracellular domain fused to an scFv that binds to a single target (left), and an exemplary PFP heterodimer in which a first subunit of the heterodimer contains an extracellular domain fused to an scFv that binds to a first target and in which a second subunit of the heterodimer subunit contains an extracellular domain fused to an scFv that binds to a second target (right).
Figure 4A:
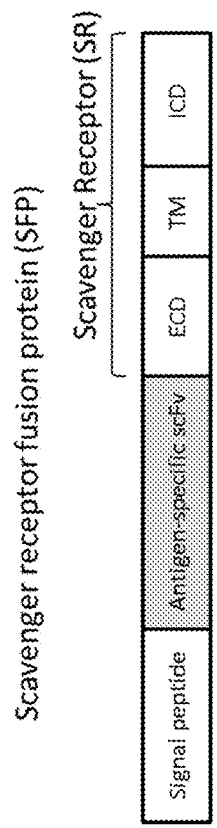
FIG. 4A is a schematic depicting an exemplary recombinant nucleic acid encoding a scavenger receptor fusion protein (SFP) containing a signal peptide fused to an antigen-specific scFv that is fused to an extracellular domain (ECD), transmembrane domain (TM) and intracellular domain of a scavenger receptor.
Figure 4B:
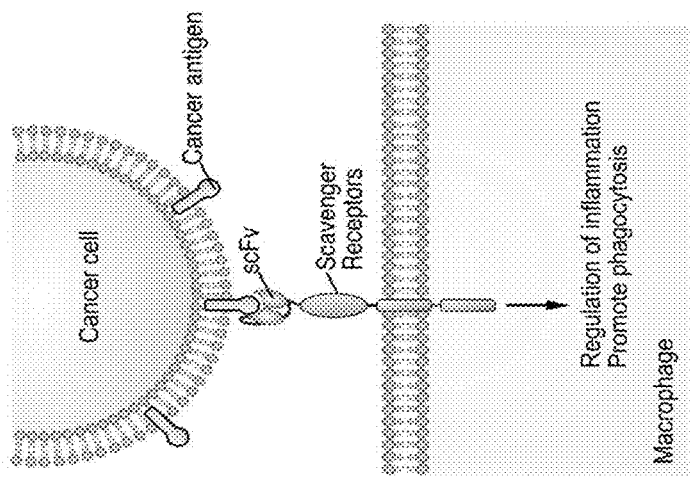
FIG. 4B is a schematic depicting the scavenger receptor fusion protein (SFP) of FIG. 4A incorporated within a cell membrane of a macrophage cell. The depicted SFP contains an scFv bound to a cancer antigen of a cancer cell. The extracellular domain (ECD), transmembrane domain (TM) and intracellular domain can be derived from one or more scavenger receptors.
Figure 4C:
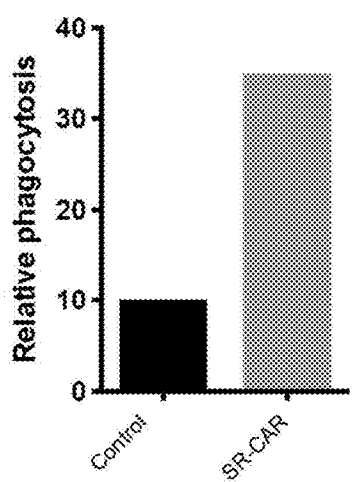
FIG. 4C is an exemplary graph depicting expected results of relative phagocytosis in human primary macrophage cells transduced with empty vector (control) or a vector encoding a scavenger receptor fusion protein (SFP) co-cultured with dye loaded tumor cells. Phagocytosis is quantified using flow cytometry.
Figure 4D:
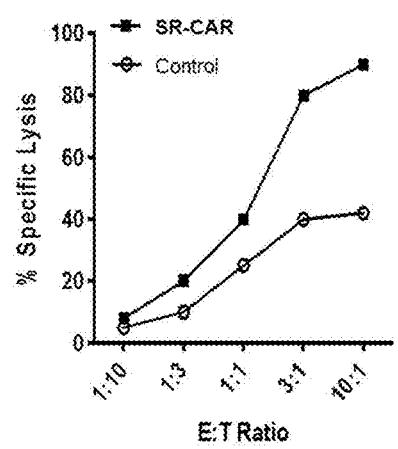
FIG. 4D is an exemplary graph depicting expected results of percent specific lysis of tumor cells when incubated in the presence of human primary macrophage cells (effector cells) transduced with empty vector (control) or a vector encoding a scavenger receptor fusion protein (SFP) co-cultured with tumor cells (target cells) expressing luciferase at the indicated effector cell:target cell ratios (E:T ratio).
Figure 4E:
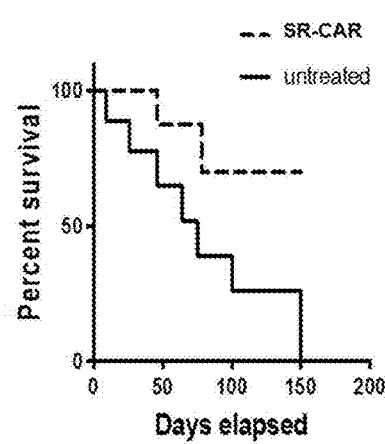
FIG. 4E is an exemplary graph depicting expected results of percent survival in a mouse xenograft tumor model after treatment with cells transduced with empty vector (control) or a vector encoding a scavenger receptor fusion protein (SFP).

In this example, a CD5-targeted PFP was constructed using known molecular biology techniques (FIG. 2A-2C). The PFP has an extracellular domain comprising a signal peptide fused to an scFv containing a heavy chain variable domain linked to a light chain variable domain that binds to CD5 on a target cell, attached to a CD8 alpha chain hinge and CD8 alpha chain TM domain via a short linker. The TM domain is fused at the cytosolic end with an FcεR gamma cytosolic portion, and a PI3K recruitment domain. The linker sequences appear italicized. The construct was prepared in a vector having a fluorescent marker and a drug (Ampicillin) resistance and amplified by transfecting a bacterial host. Following plasmid isolation, the construct was sequenced. The sequence is provided below:

```
CD5-FcR-PI3K
                                         (SEQ ID NO: 14)
MWLQSLLLLGTVACSISEIQLVQSGGGLVKPGGSVRISCAASGYT

FTNYGMNWVRQAPGKGLEWMGWINTHTGEPTYADSFKGRFTFSLD

DSKNTAYLQINSLRAEDTAVYFCTRRGYDWYFDVWGQGTTVTV*SS*

*GGGGSGGGGSGGGGS*DIQMTQSPSSLSASVGDRVTITCRASQDIN

SYLSWFQQKPGKAPKTLIYRANRLESGVPSRF*SGSGSG*TDYTLTI

SSLQYEDFGIYYCQQYDESPWTFGGGTKLEIK*SGGGGS*ALSNSI

MYFSHFVPVFLPAKPTTTPAPRPPTPAPTIASQPLSLRPEACRPA

AGGAVHTRGLDIYIWAPLAGTCGVLLLSLVITLYCRRLKIQVRKA

AITSYEKSDGVYTGLSTRNQETYETLKHEKPPQ*GSGS*YEDMRGIL

YAAPQLRSIRGQPGPNHEEDADSYENM.
``` mRNA was generated by in vitro reverse transcription of the purified plasmids using suitable primers. The purified mRNA was transduced into a cell line for expression analysis.

Example 11. HER2-FcR-PI3K PFP Construct

In this example, a HER2-targeted PFP was constructed using known molecular biology techniques. The PFP has an extracellular domain comprising a signal peptide fused to an scFv containing a heavy chain variable domain linked to a light chain variable domain that binds to HER2 on a target cell, attached to a CD8 alpha chain hinge and CD8 alpha chain TM domain via a short linker. The TM domain is fused at the cytosolic end with an FcγR gamma cytosolic portion, and a PI3K recruitment domain as in the previous example. Linkers are marked as italicized. Following protocols similar to Example 10, the construct was sequenced. The sequence is provided below:

```
HER2-FcR-PI3K
                                         (SEQ ID NO: 15)
MWLQSLLLLGTVACSISDIQMTQSPSSLSASVGDRVTITCRASQD

VNTAVAWYQQKPGKAPKLLIYSASFLYSGVPSRFSGSRSGTDFTL

TISSLQPEDFATYYCQQHYTTPPTFGQGTKVEIKRTGSTSGSGKP

GSGEGSEVQLVE*SGGGL*VQPGGSLRLSCAASGFNIKDTYIHWVRQ

APGKGLEWVARIYPTNGYTRYADSVKGRFTISADTSKNTAYLQMN

SLRAEDTAVYYCSRWGGDGFYAMDVWGQGTLVTV*SSSGGGGS*GAL

SNSIMYFSHFVPVFLPAKPTTTPAPRPPTPAPTIASQPLSLRPEA

CRPAAGGAVHTRGLDIYIWAPLAGTCGVLLLSLVITLYCRRLKIQ

VRKAAITSYEKSDGVYTGLSTRNQETYETLKHEKPPQ*GSGS*YEDM

RGILYAAPQLRSIRGQPGPNHEEDADSYENM.
```

Example 12. CD5-FcR-CD40 PFP Construct

In this example, a CD5-targeted PFP was constructed using known molecular biology techniques having an intracellular domain comprising CD40 sequence. The PFP has an extracellular domain comprising a signal peptide fused to an scFv containing a heavy chain variable domain linked to a light chain variable domain that binds to CD5 on a target cell, attached to a CD8 alpha chain hinge and CD8 alpha chain TM domain via a short linker. The TM domain is fused at the cytosolic end with an FcRγ cytosolic portion, followed by a CD40 cytosolic portion. Linkers are marked as italicized. Following protocols similar to Example 10, the construct was sequenced. The sequence is provided below:

```
CD5-FcR-CD40
                                         (SEQ ID NO: 16)
MWLQSLLLLGTVACSISEIQLVQSGGGLVKPGGSVRISCAASGYT

FTNYGMNWVRQAPGKGLEWMGWINTHTGEPTYADSFKGRFTFSLD

DSKNTAYLQINSLRAEDTAVYFCTRRGYDWYFDVWGQGTTVTV*SS*

*GGGGSGGGGSGGGGS*DIQMTQSPSSLSASVGDRVTITCRASQDIN

SYLSWFQQKPGKAPKTLIYRANRLESGVPSRFSGSGSGTDYTLTI

SSLQYEDFGIYYCQQYDESPWTFGGGTKLEIK*SGGGGS*ALSNSI

MYFSHFVPVFLPAKPTTTPAPRPPTPAPTIASQPLSLRPEACRPA

AGGAVHTRGLDIYIWAPLAGTCGVLLLSLVITLYCRLKIQVRKAA

ITSYEKSDGVYTGLSTRNQETYETLKHEKPPQKKVAKKPTNKAPH

PKQEPQEINFPDDLPGSNTAAPVQETLHGCQPVTQEDGKESRISV

QERQ.
```

Example 13. Expression of Anti-CD5 Chimeric Antigen Receptors

Figure 8:
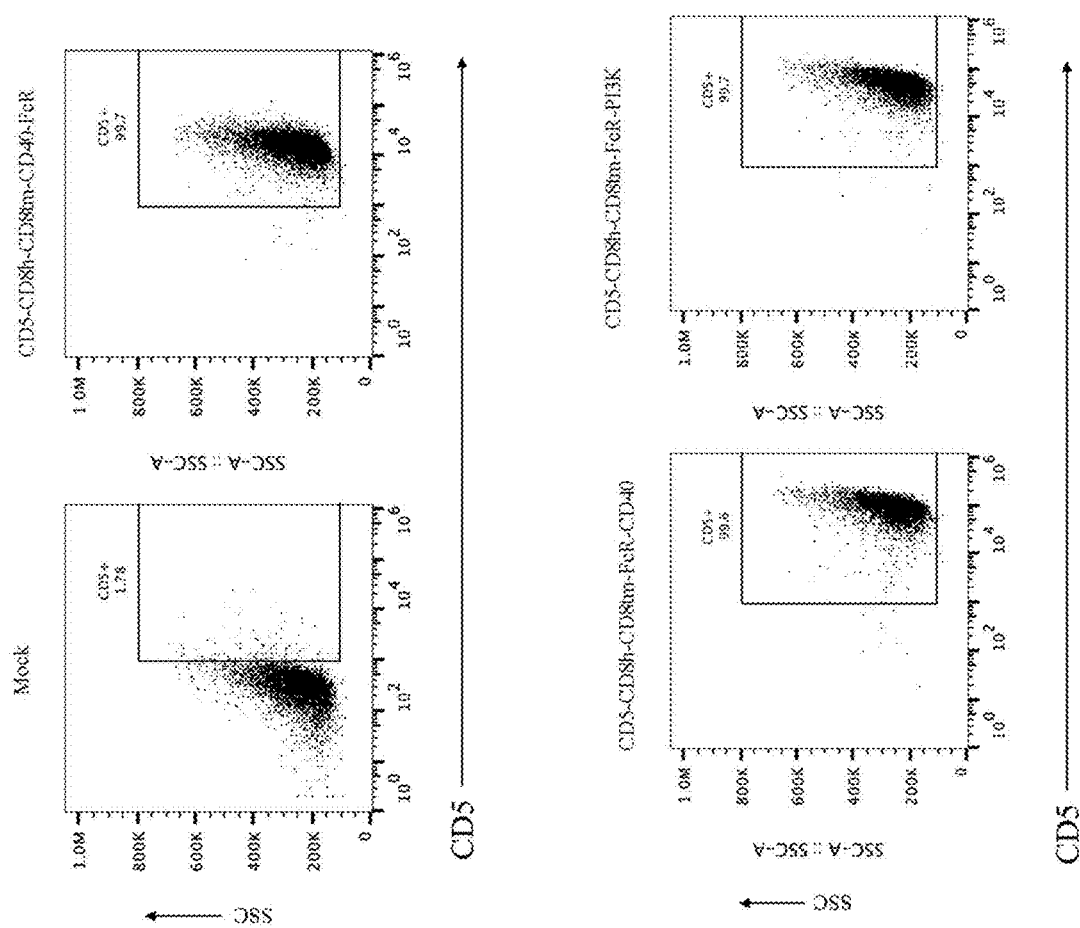
FIG. 8 depicts exemplary flow cytometry data (side scatter (SSC) vs CD5+) after mock expression or expression of various constructs having an extracellular domain (ECD) with an anti-CD5 scFv in myeloid cells. The depicted constructs include an ECD containing an anti-CD5 scFv fused to a CD8 hinge domain fused to a CD8 transmembrane domain fused to a CD40 intracellular domain, fused to an FcRγ intracellular domain (CD5-CD8h-CD8tm-CD40-FcR); an ECD containing an anti-CD5 scFv fused to a CD8 hinge domain fused to a CD8 transmembrane domain fused to an FcRγ intracellular domain, fused to a CD40 intracellular domain (CD5-CD8h-CD8tm-FcR-CD40); an ECD containing an anti-CD5 scFv fused to a CD8 hinge domain fused to a CD8 transmembrane domain fused to an FcRγ intracellular domain, fused to a PI3K recruitment domain (CD5-CD8h-CD8tm-FcR-PI3K); an ECD containing an anti-CD5 scFv fused to a CD8 hinge domain fused to a CD8 transmembrane domain fused to an FcRγ intracellular domain (CD5-CD8h-CD8tm-FcR); an ECD containing an anti-CD5 scFv fused to a CD8 hinge domain fused to a CD8 transmembrane domain (CD5-CD8h-CD8tm-no ICD); an ECD containing an anti-CD5 scFv fused to a CD28 hinge domain fused to a CD28 transmembrane domain fused to an FcRγ intracellular domain fused to a PI3K recruitment domain (CD5-CD28h-CD28tm-FcR-PI3K); an ECD containing an anti-CD5 scFv fused to a CD8 hinge domain fused to a CD68 transmembrane domain fused to an FcRγ intracellular domain fused to a PI3K recruitment domain (CD5-CD8h-CD68tm-FcR-PI3K); an ECD containing an anti-CD5 scFv fused to a CD8 transmembrane domain fused to an FcRγ intracellular domain fused to a PI3K recruitment domain (CD5-CD8tm-FcR-PI3K); an ECD containing an anti-CD5 scFv fused to a CD28 transmembrane domain fused to an FcRγ intracellular domain fused to a PI3K recruitment domain (CD5-CD28tm-FcR-PI3K); and an ECD containing an anti-CD5 scFv fused to a CD68 transmembrane domain fused to an FcRγ intracellular domain fused to a PI3K recruitment domain (CD5-CD68tm-FcR-PI3K).
Figure 8:
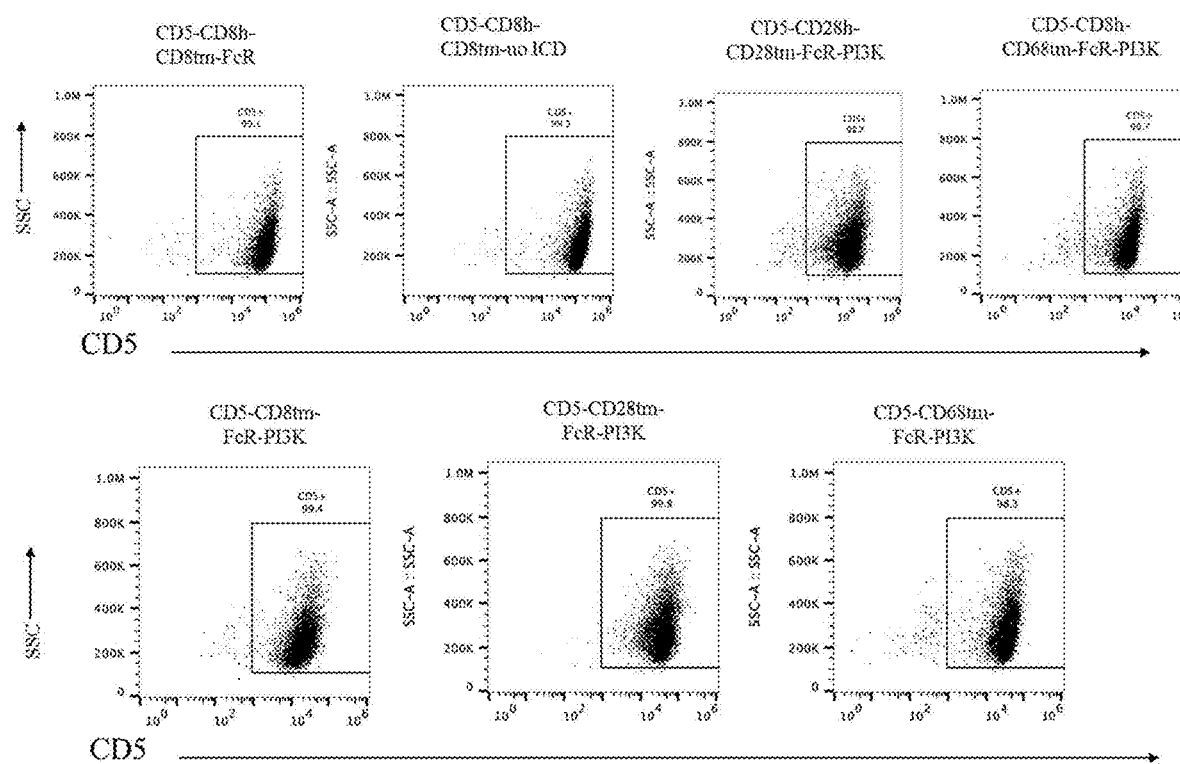
Figure 9:
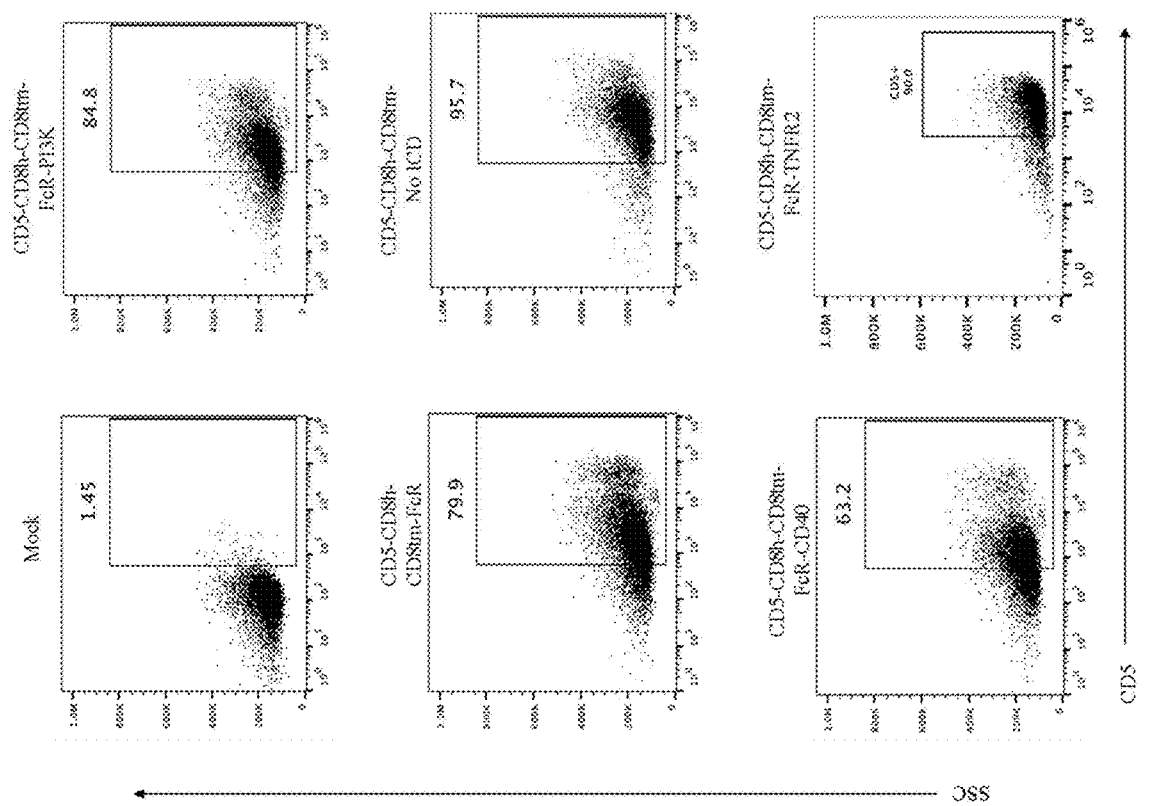
FIG. 9 depicts exemplary flow cytometry data (side scatter (SSC) vs CD5+) after mock expression or expression of various constructs having an extracellular domain (ECD) with an anti-CD5 scFv in myeloid cells. The depicted constructs include an ECD containing an anti-CD5 scFv fused to a CD8 hinge domain fused to a CD8 transmembrane domain fused to an FcRγ intracellular domain, fused to a PI3K recruitment domain (D5-CD8h-CD8tm-FcR-PI3K); an ECD containing an anti-CD5 scFv fused to a CD8 hinge domain fused to a CD8 transmembrane domain fused to an FcRγ intracellular domain (CD5-CD8h-CD8tm-FcR); an ECD containing an anti-CD5 scFv fused to a CD8 hinge domain fused to a CD8 transmembrane domain (CD5-CD8h-CD8tm-no ICD); an ECD containing an anti-CD5 scFv fused to a CD8 hinge domain fused to a CD8 transmembrane domain fused to an FcRγ intracellular domain fused to a CD40 intracellular domain (CD5-CD8h-CD8tm-FcR-CD40); and an ECD containing an anti-CD5 scFv fused to a CD8 hinge domain fused to a CD8 transmembrane domain fused to an FcRγ intracellular domain, fused to a TNFR2 intracellular domain (CD5-CD8h-CD8tm-FcR-TNFR2).

In this example, cells from monocytic cell line THP-1, were electroporated with individual anti-CD5 chimeric antigen receptor (CD5 CAR) constructs with either no intracellular domain (No ICD); or intracellular domain (ICD) having a CD40 signaling domain, or a FcR signaling domain; or with PI3kinase (PI3K) recruitment signaling domain; or with a first CD40 signaling domain and a second signaling domain from FcR intracellular domain or vice versa; with a first FcR signaling domain and a second PI3K recruitment signaling domain or vice versa, and expression of the CAR construct was determined by flow cytometry as indicated in FIG. 8. In each case, a robust expression of greater than 95% cells was observed. FIG. 9 shows expression of some of these constructs in primary human myeloid cells. Table 6 describes the domains of the constructs in the figures.

TABLE 6

CD5-CAR constructs

| CD5 binding construct (CD5-CAR) name | Intracellular domain derived from: (ICD1 and ICD2) | TM domain derived from: | Hinge derived from | ECD from |
|---|---|---|---|---|
| CD5-CD8h-CD8tm-CD40-FcR | CD40 and FcR | CD8 | CD8 | Anti-CD5 scFv |
| CD5-CD8h-CD8tm-FcR-CD40 | FcR and CD40 | CD8 | CD8 | Anti-CD5 scFv |
| CD5-CD8h-CD8tm-FcR-PI3K | FcR and PI3K | CD8 | CD8 | Anti-CD5 scFv |
| CD5-CD8h-CD8tm-FcR | FcR | CD8 | CD8 | Anti-CD5 scFv |
| CD5-CD8h-CD8tm-no ICD | None | CD8 | CD8 | Anti-CD5 scFv |
| CD5-CD28h-CD28tm-FcR-PI3K | FcR and PI3K | CD28 | CD28 | Anti-CD5 scFv |
| CD5-CD8h-CD68tm-FcR-PI3K | FcR and PI3K | CD68 | CD8 | Anti-CD5 scFv |
| CD5-CD8tm-FcR-PI3K | FcR and PI3K | CD8 | — | Anti-CD5 scFv |
| CD5-CD28tm-FcR-PI3K | FcR and PI3K | CD28 | — | Anti-CD5 scFv |
| CD5-CD68tm-FcR-PI3K | FcR and PI3K | CD68 | — | Anti-CD5 scFv |
| CD5-CD8h-CD8tm-FcR-TNFR2 | FcR and TNFR2 | CD8 | CD8 | Anti-CD5 scFv |

Example 14. Phagocytosis and Activation Assays

Figure 10A:
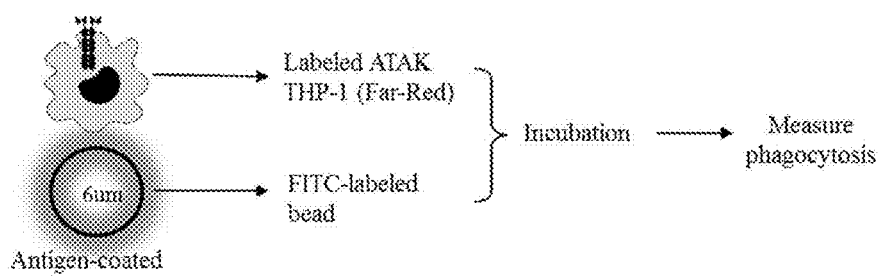
FIG. 10A depicts a schematic showing an exemplary experimental flow diagram of a phagocytic assay using FITC-labeled beads coated in antigen targeted by FarRed fluorophore-labeled chimeric antigen receptors expressed in THP-1 cells.
Figure 10B:
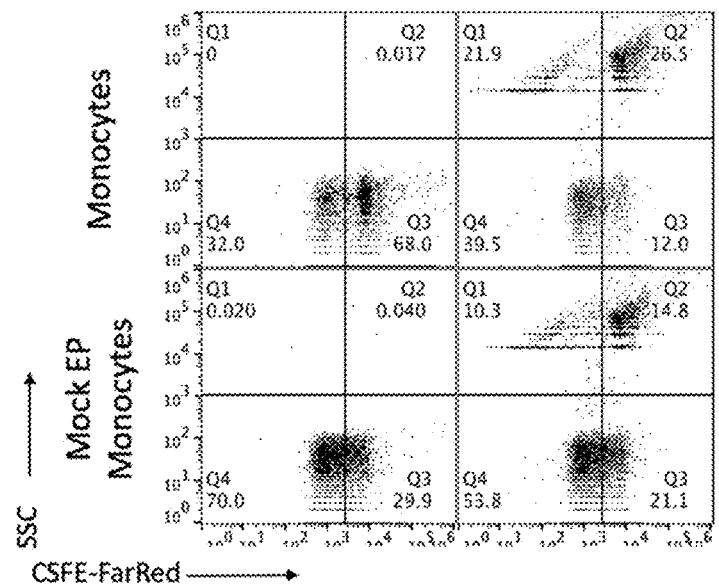
FIG. 10B depicts exemplary flow cytometry data (side scatter (SSC) vs CSFE-FarRed) after mock expression or expression of anti-CD5 chimeric antigen receptors using the experimental design of FIG. 10A.
Figure 10C:
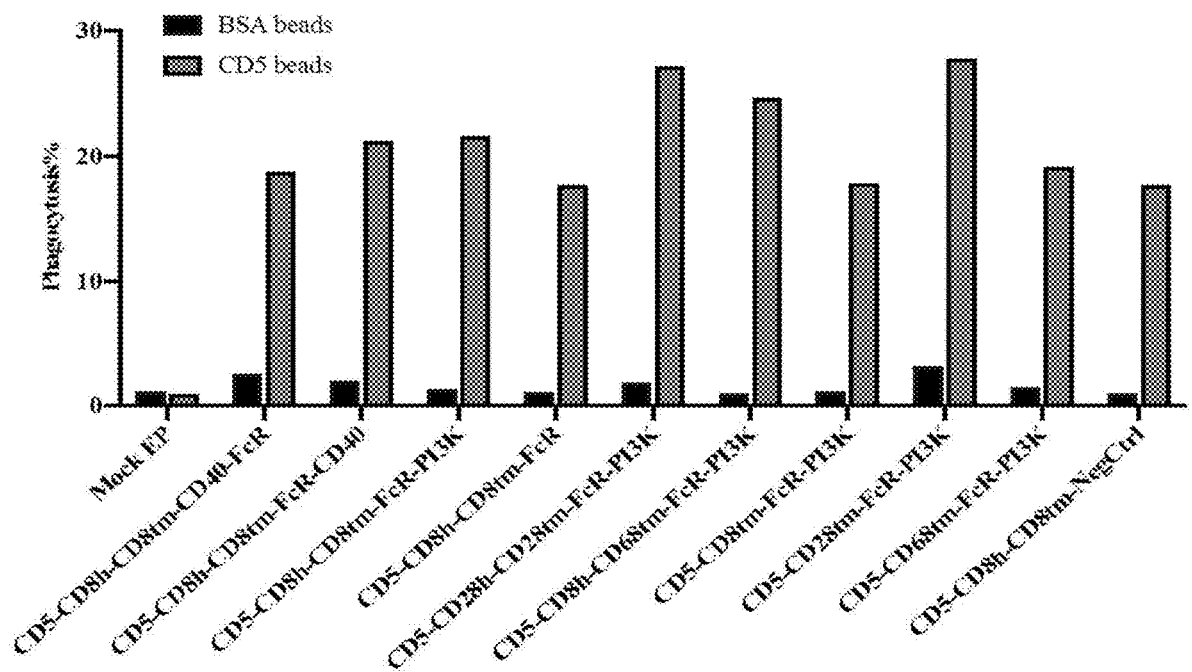
FIG. 10C depicts an exemplary graph showing relative phagocytosis in human primary macrophage cells transduced with empty vector (mock) or a vector encoding the depicted chimeric receptor fusion proteins co-cultured with FITC-labeled beads coated with BSA or CD5 using the experimental design of FIG. 10A.
Figure 10D:
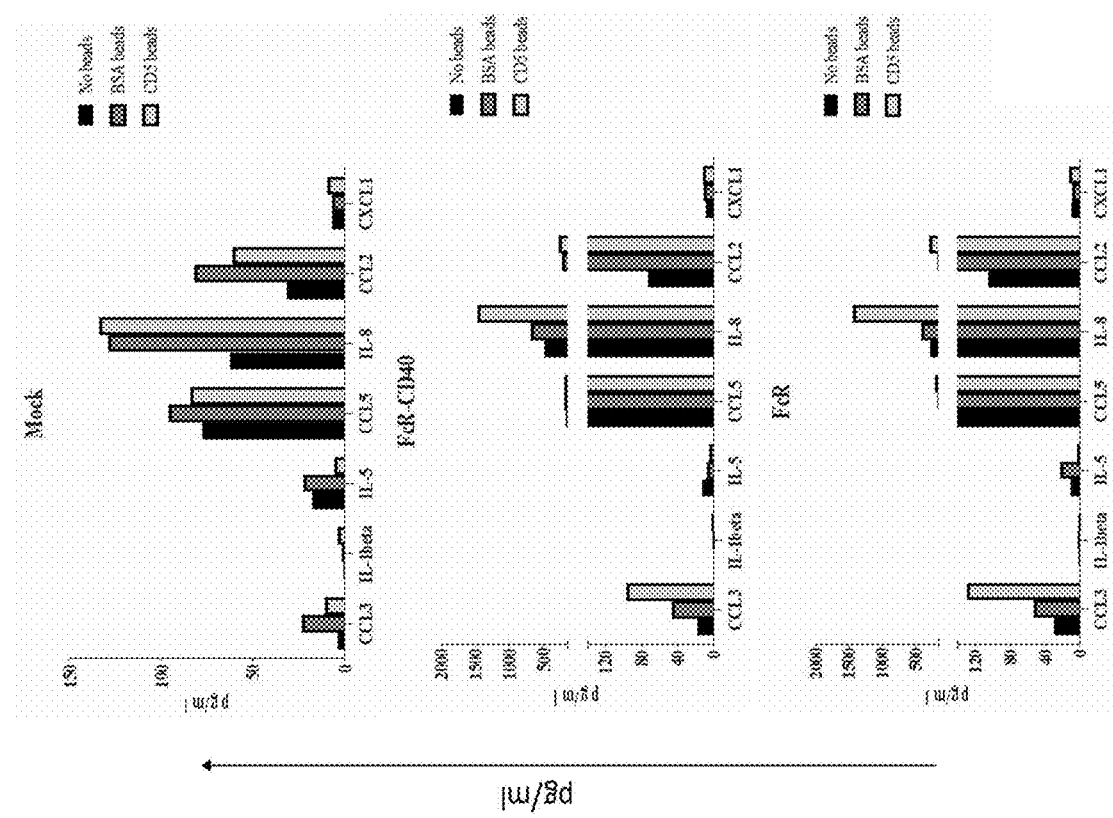
FIG. 10D depicts exemplary bar graphs of the concentration (pg/mL) of the indicated proteins after mock expression or expression of the indicated anti-CD5 chimeric antigen receptors using the experimental design of FIG. 10A. Each of the chimeric receptor fusion proteins contained an ECD containing an anti-CD5 scFv fused to a CD8 hinge domain fused to a CD8 transmembrane domain fused to the indicated intracellular domains.
Figure 10D:
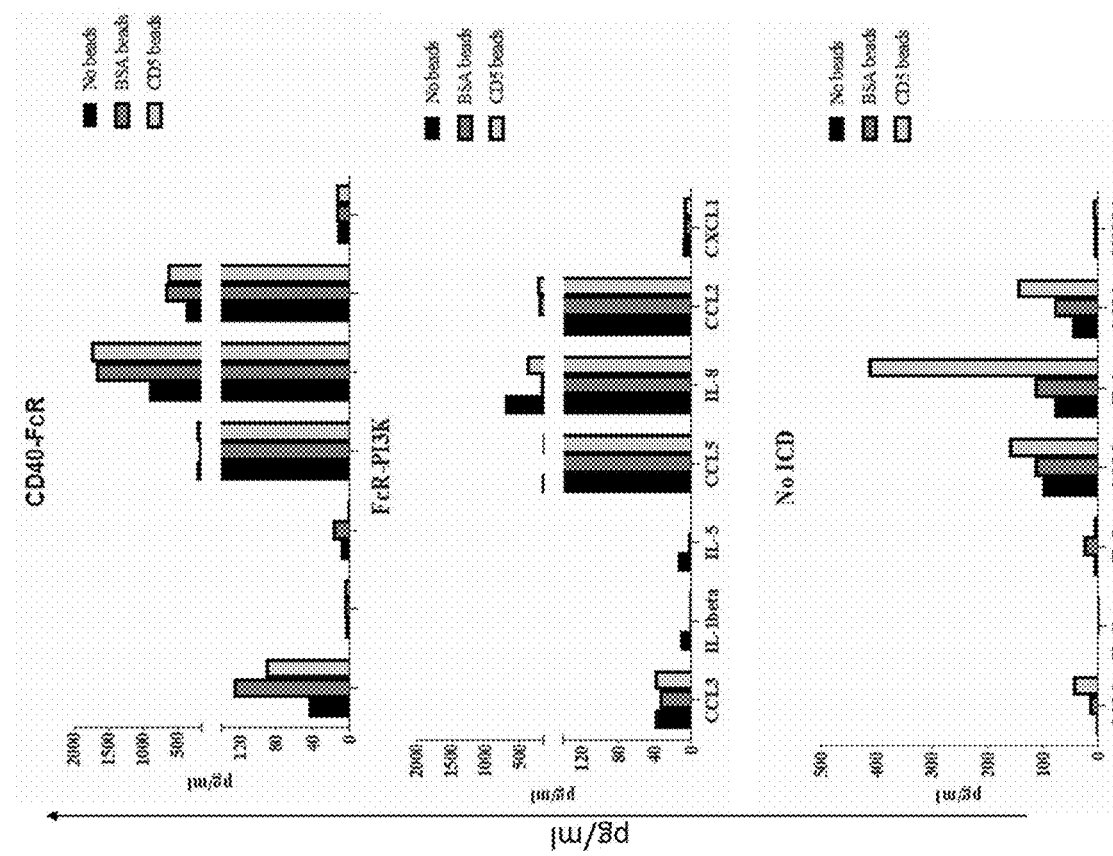
Figure 10E:
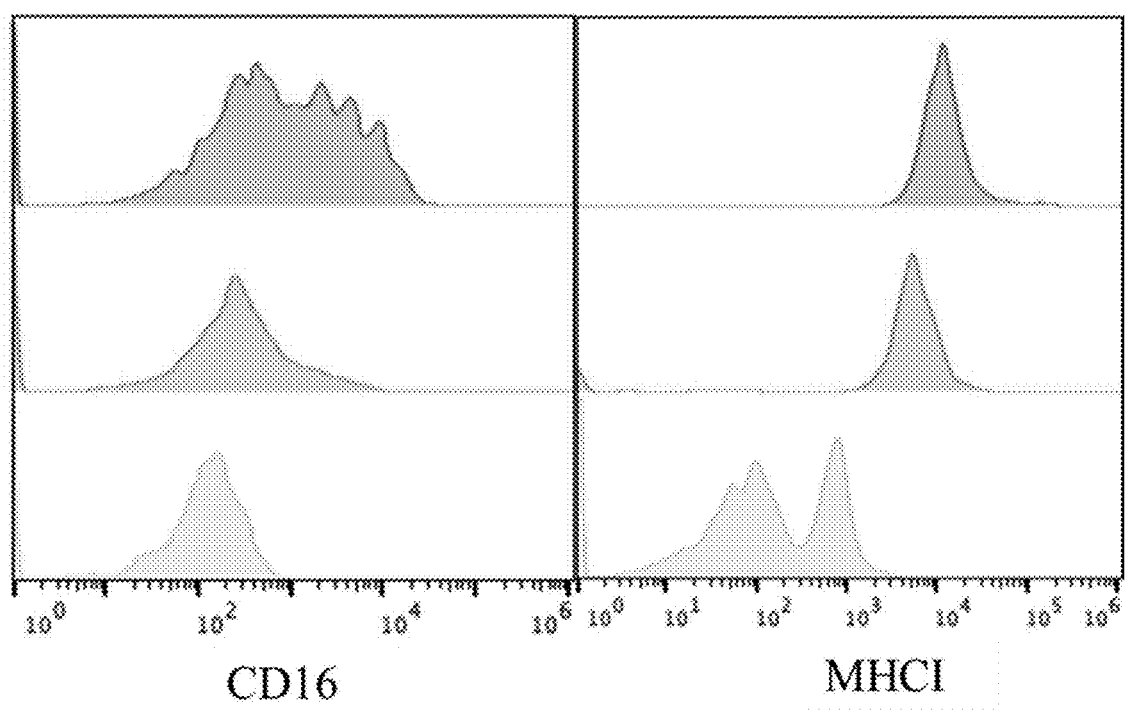
FIG. 10E depicts an exemplary graph measuring expression of M1 associated markers CD16 and MHC class I in primary human monocyte cells expressing an anti-CD5 chimeric antigen receptor that were incubated in the presence of IL-10, IL-4 and TGFβ for 24 hours and then incubated with H9 T cell lymphoma cells. The primary human monocyte cells expressing the anti-CD5 chimeric antigen receptor demonstrated potent activity in an M2 environment.
Figure 10F:
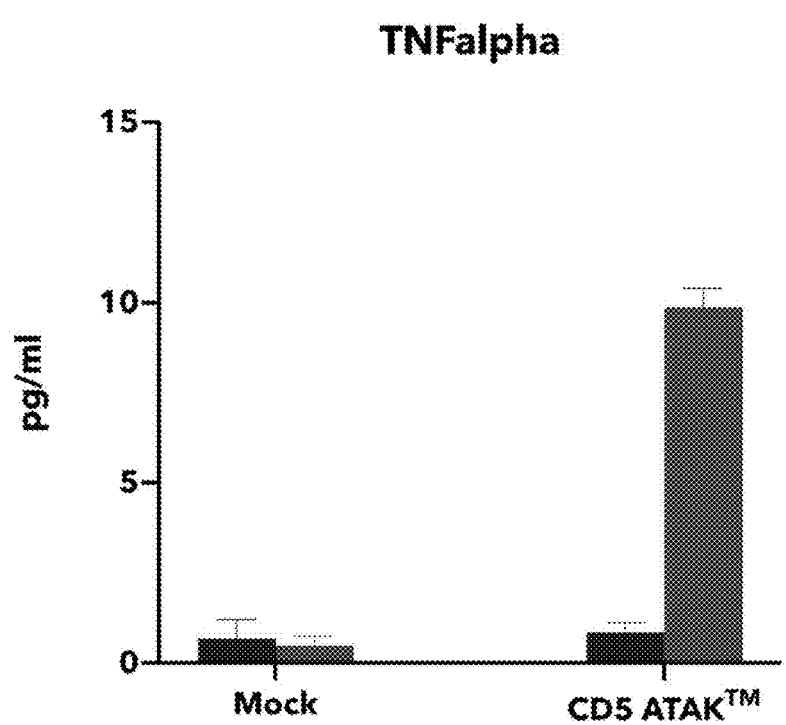
FIG. 10F depicts an exemplary bar graph of the concentration (pg/mL) of TNF-alpha after incubating primary human monocyte cells expressing an anti-CD5 chimeric antigen receptor in the presence of IL-10, IL-4 and TGFβ for 24 hours and then H9 T cell lymphoma cells overnight. The primary human monocyte cells expressing the anti-CD5 chimeric antigen receptor were able to function in tumor microenvironment (TME) like conditions to produce inflammatory mediators.
Figure 10G:
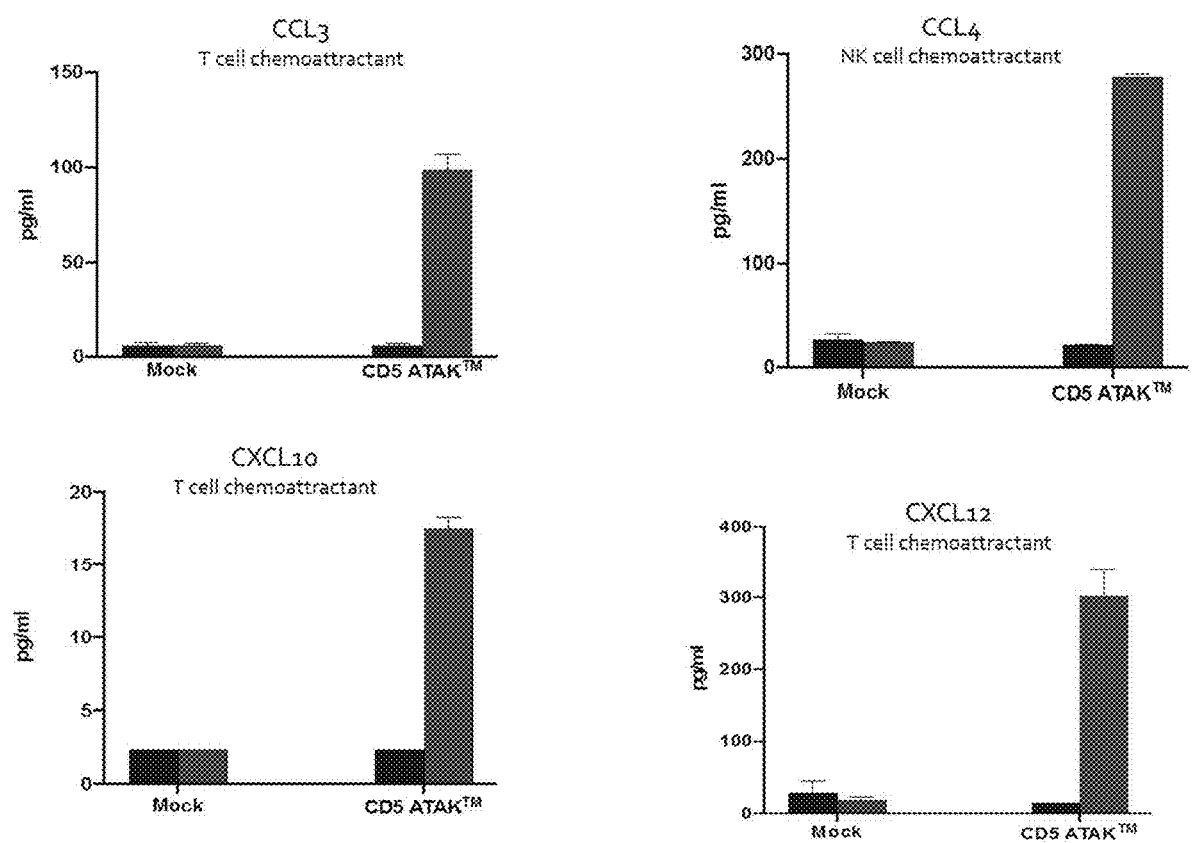
FIG. 10G depicts exemplary bar graphs of the concentration (pg/mL) of the indicated chemoattractants (CCL3, CCL4, CXCL10 and CXCL12) after incubating primary human monocyte cells expressing an anti-CD5 chimeric antigen receptor in the presence of IL-10, IL-4 and TGFβ for 24 hours and then H9 T cell lymphoma cells overnight. The primary human monocyte cells expressing the anti-CD5 chimeric antigen receptor were able to function to secrete a broad range of chemokines, including T cell chemoattractants and NK cell chemoattractants in tumor microenvironment (TME) like conditions.
Figure 10H:
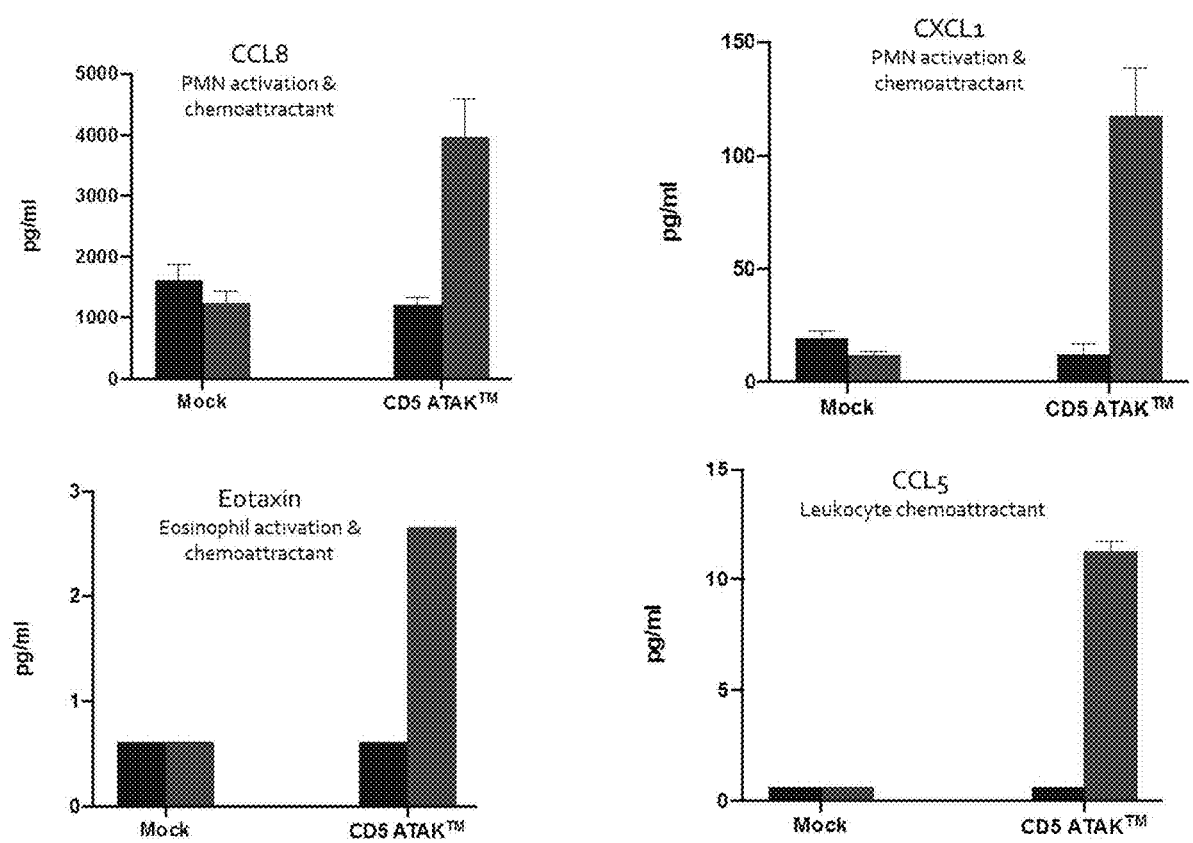
FIG. 10H depicts exemplary bar graphs of the concentration (pg/mL) of the indicated chemoattractants (CCL8, CXCL1, eotaxin and CCL5) after incubating primary human monocyte cells expressing an anti-CD5 chimeric antigen receptor in the presence of IL-10, IL-4 and TGFβ for 24 hours and then H9 T cell lymphoma cells overnight. The primary human monocyte cells expressing the anti-CD5 chimeric antigen receptor were able to function to secrete a broad range of chemokines, including chemokines that activate PMN and eosinophil and leukocyte chemoattractants.

For functional analysis of the various CD5-binding CFP expressing THP-1 macrophages, cells were fed 6 μm FITC-labeled CD5 antigen-coated beads (FIG. 10A) and phagocytic engulfment of the FITC beads per cell was quantitated by flow cytometry (FIG. 10B). Control beads were BSA coated. Experimental CD5-coated beads were readily engulfed by THP-1 cells (FIG. 10C). Each of the constructs showed high level of phagocytosis that was target specific, and the CD5-coated bead uptake was at least 10-fold higher compared to uptake of BSA coated beads. FIG. 10D shows cytokine analysis of the C5-CAR expressing cells in presence of the control BSA coated beads or experimental CD5 coated beads. Higher cytokine response was observed in the CD5-CAR expressing cells, compared to mock electroporation, although the induction of cytokines were not exceedingly high in absence of any further stimuli. CD5 CAR expressing cells exhibit low expression of CD16 and MHC class I molecules, which are hallmarks of non-classical monocytes (FIG. 10E). However, in presence of an activation stimulus, the CD5 expressing cells were shown to be highly activated with induction of the cytokines as shown FIGS. 10F-10H.

Figure 11A:
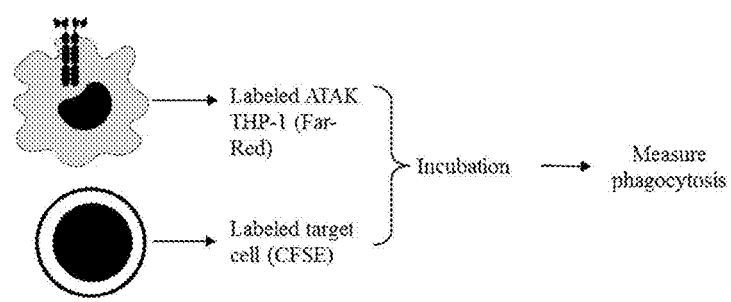
FIG. 11A depicts a schematic showing an exemplary experimental flow diagram of a phagocytic assay using CFSE-labeled target cells targeted by FarRed fluorophore-labeled chimeric antigen receptors expressed in THP-1 cells.
Figure 11B:
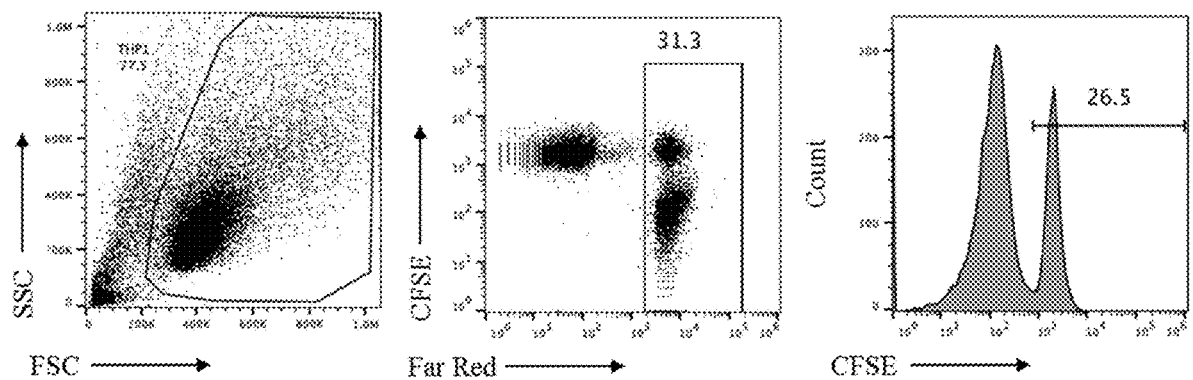
FIG. 11B depicts exemplary flow cytometry data (side scatter (SSC) vs forward scatter (FSC); CSFE vs FarRed; and cell counts vs CSFE) after mock expression or expression of anti-CD5 chimeric antigen receptors in THP-1 cells using the experimental design of FIG. 11A. A myeloid cell line was electroporated with an anti-CD5 chimeric antigen receptor and labelled with the intracellular FarRed dye. These cells were incubated with H9 T cell cancer cells that were pre-labelled with CFSE at a 1:3 myeloid cell:tumor cell ratio. After 4 hours, phagocytosis was measured by flow cytometry.
Figure 11C:
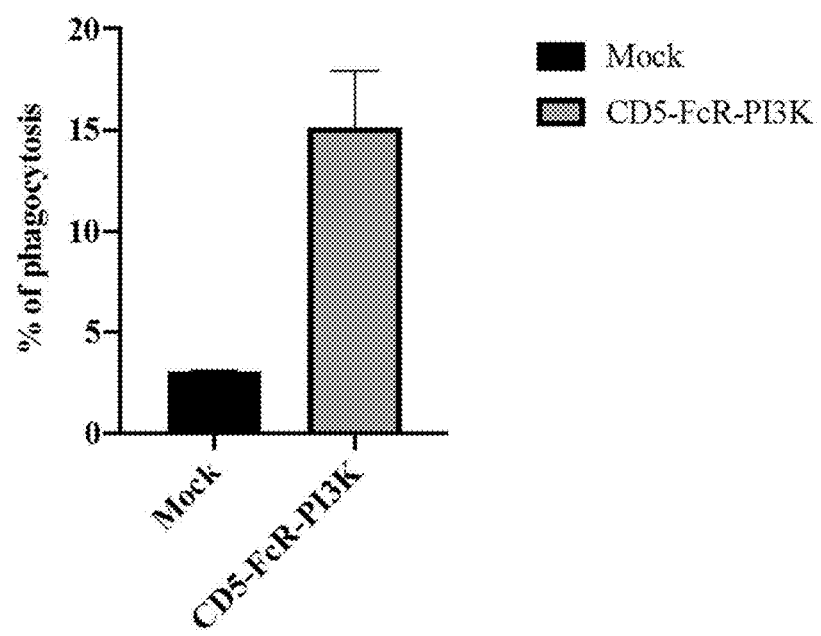
FIG. 11C depicts an exemplary graph showing relative phagocytosis in a myeloid cell line electroporated with empty vector (mock) or a vector encoding the depicted chimeric receptor fusion protein and labelled with the intracellular FarRed dye using the experimental design of FIG. 11A. These cells were incubated with H9 T cell cancer cells that were pre-labelled with CFSE at a 1:3 myeloid cell: tumor cell ratio. After 4 hours, phagocytosis was measured by flow cytometry.

THP-1 cells were electroporated with the CFP construct encoding CD5-CD8h-CD8tm-FcR-PI3K and labelled with the intracellular FarRed dye. These cells were incubated with H9 T cell cancer cells that were pre-labelled with CFSE as a 1:3 myeloid cell:tumor cell ratio. After 4 hours phagocytosis was measured by flow cytometry (FIG. 11A). The cancer cells were readily phagocytosed by the CFP-expressing cells (FIG. 11B, 11C).

Figure 12A:
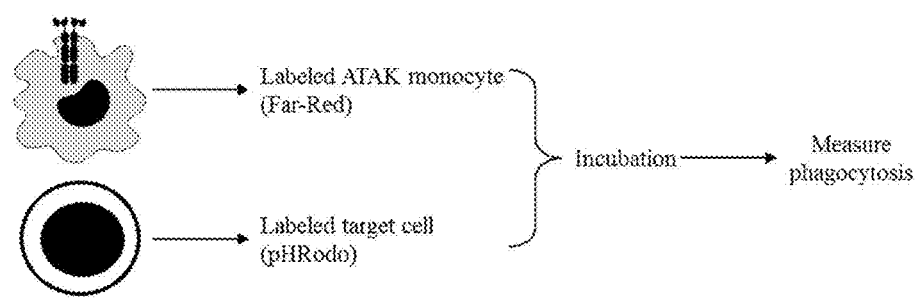
FIG. 12A depicts a schematic showing an exemplary experimental flow diagram of a phagocytic assay using pHRodo-labeled target cells targeted by FarRed fluorophore-labeled chimeric antigen receptors expressed in primary human monocyte cells.
Figure 12B:
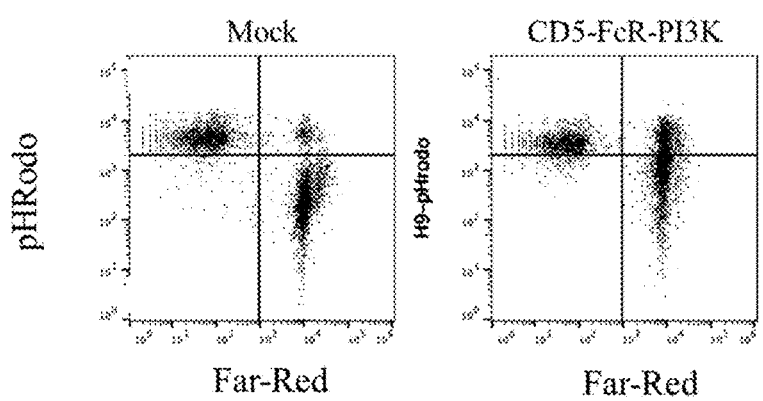
FIG. 12B depicts exemplary flow cytometry data (pHRodo vs FarRed) after mock expression or expression of anti-CD5 chimeric antigen receptors in primary human monocyte cells using the experimental design of FIG. 12A. Primary human monocyte cells were electroporated with an anti-CD5 chimeric antigen receptor and labelled with the intracellular FarRed dye. These cells were incubated with H9 T cell cancer cells that were pre-labelled with pHRodo. After incubation, phagocytosis was measured by flow cytometry
Figure 12C:
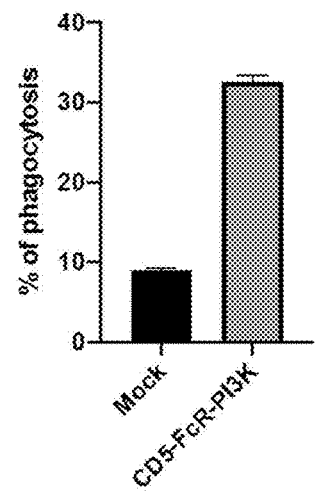
FIG. 12C depicts an exemplary graph quantifying the results of FIG. 12B showing relative phagocytosis after mock expression or expression of the depicted anti-CD5 chimeric antigen receptors in primary human monocyte cells using the experimental design of FIG. 12A.
Figure 12D:
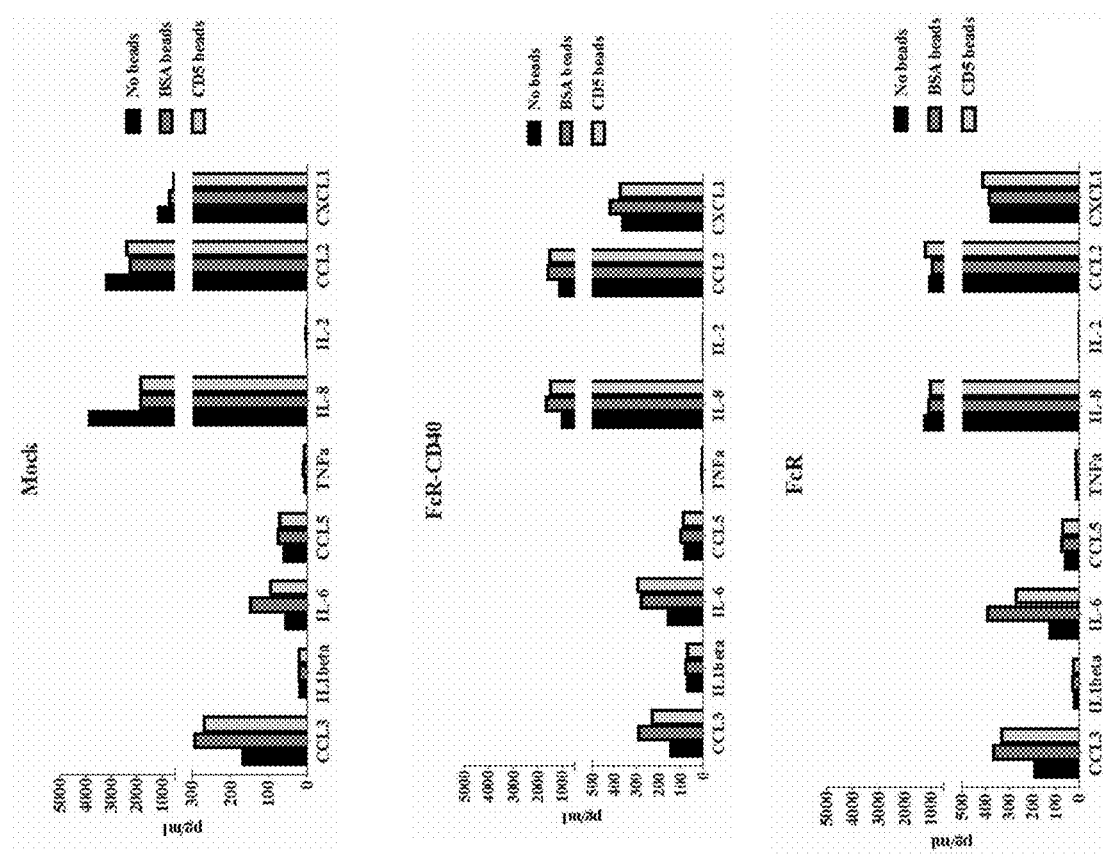
FIG. 12D depicts exemplary bar graphs of the concentration (pg/mL) of the indicated proteins after mock expression or expression of the indicated anti-CD5 chimeric antigen receptors in monocyte cells after performing a bead-based phagocytic assay.
Figure 12D:
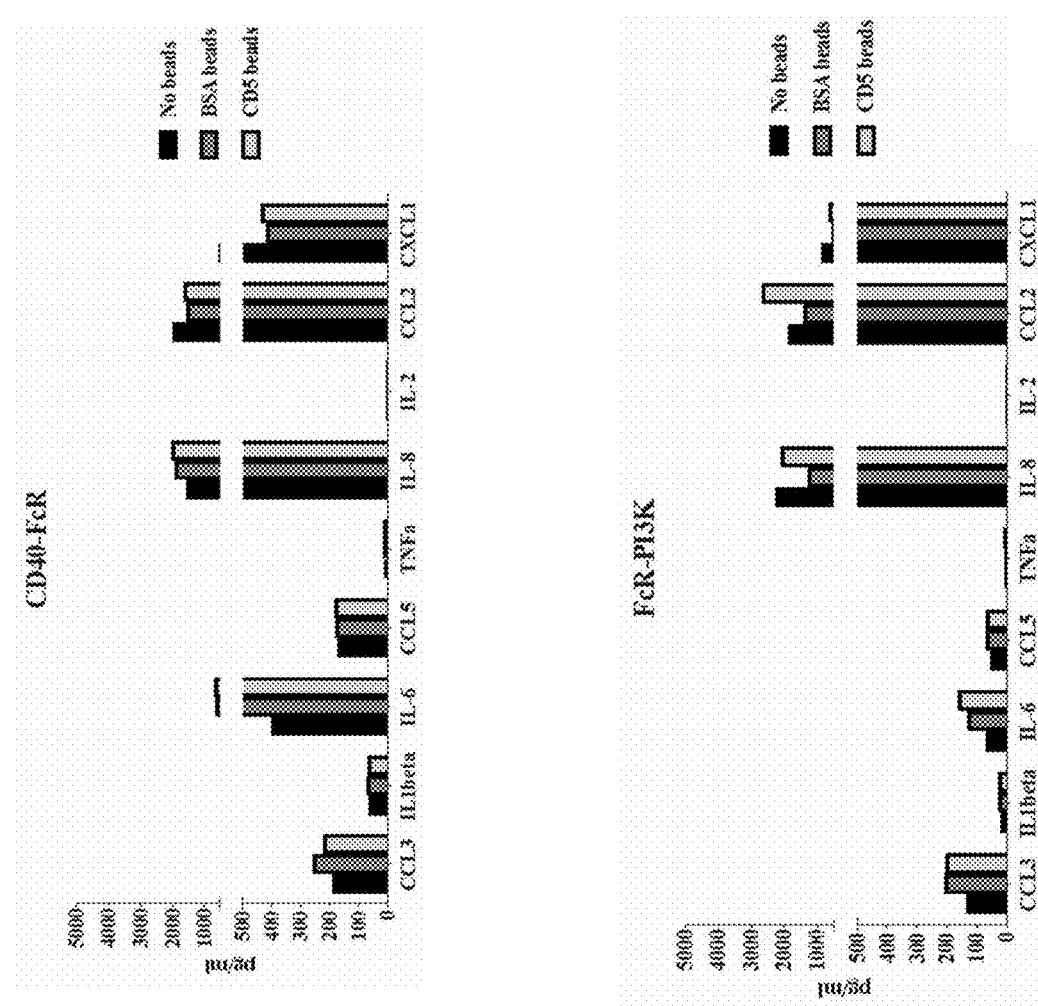

Primary monocytes electroporated with the CD5-CAR construct was assayed for bead engulfment, target specificity and cytokine as above. With pHRodo labeled target cells, (FIG. 12A) increased phagocytic engulfment was noticed (FIGS. 12B and 12C) in case of any of the monocytic cells expressing any of the CD5-binder constructs, compared to mock electroporated cells. In another experiment, primary monocytes were electroporated with CD5-CAR construct (CD5-CD8h-CD8tm-FcR-PI3K) and assayed for phagocytosis and cytokine release. Results are shown in FIG. 12D.

Figure 13:
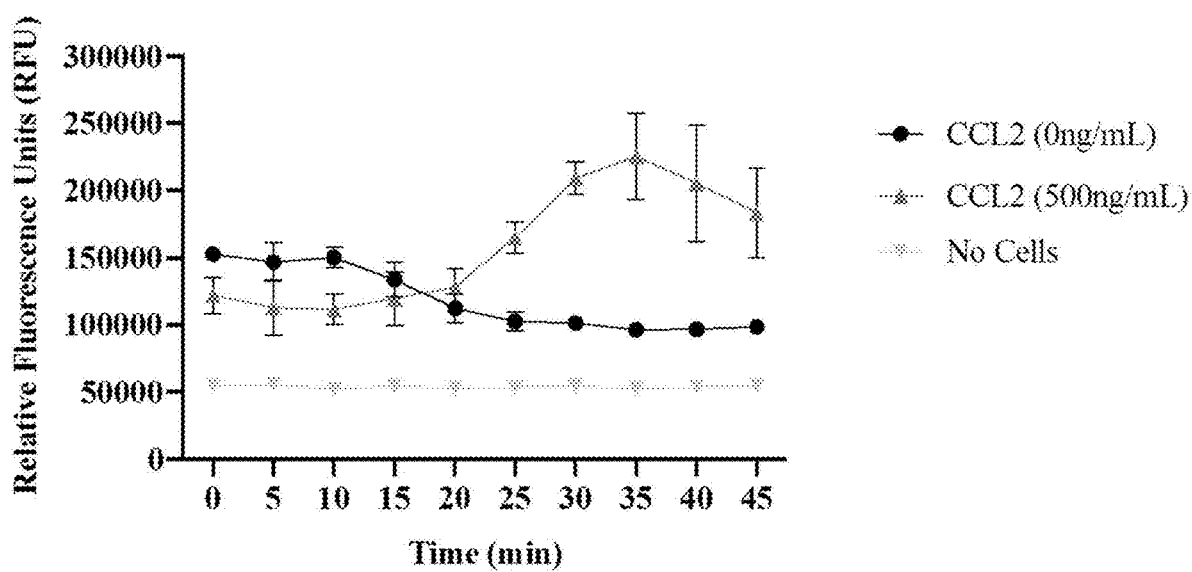
FIG. 13 depicts an exemplary graph of relative fluorescence units (RFUs) over time after incubation of no cells or THP-1 cells expressing an anti-CD5 chimeric antigen receptor with CCL2 at the indicated concentrations. Fold increase over control depicts a ratio of CCL2-induced chemotaxis as compared to cells treated with assay buffer alone. Each bar on the graph represents a mean±SD of two replicate wells.
Figure 14:
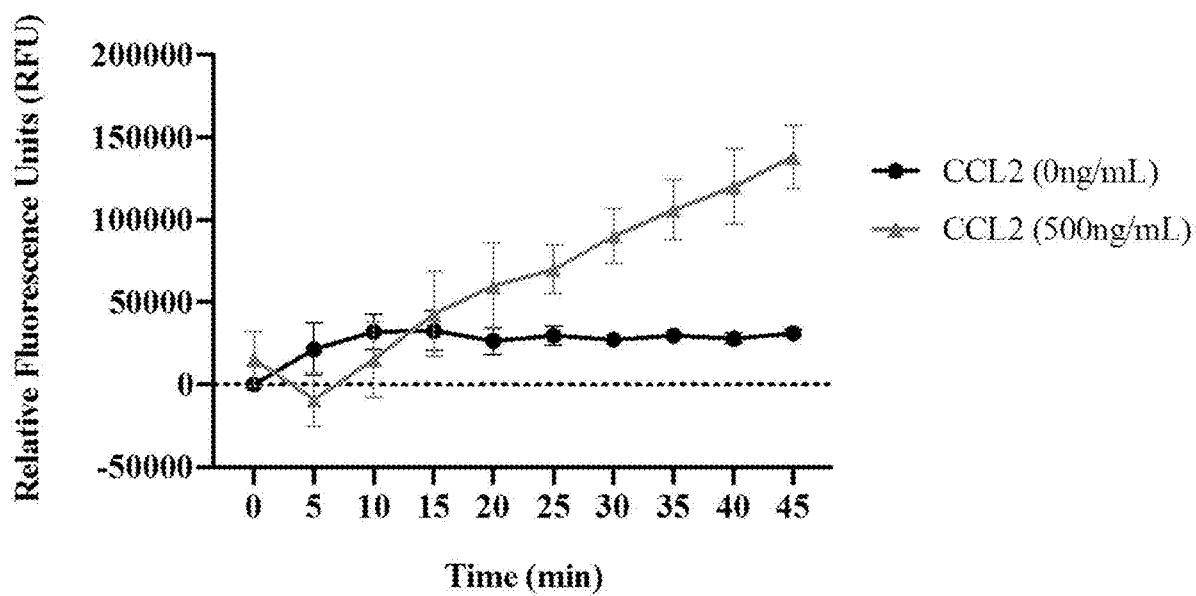
FIG. 14 depicts an exemplary graph of relative fluorescence units (RFUs) over time after incubation of no cells or primary human monocyte cells expressing an anti-CD5 chimeric antigen receptor with CCL2 at the indicated concentrations. Fold increase over control depicts a ratio of CCL2-induced chemotaxis as compared to cells treated with assay buffer alone. Each bar on the graph represents a mean±SD of two replicate wells.

Both THP-1 cells primary monocytes were highly responsive to CCL2 administration in vitro and exhibited increased chemotaxis (FIGS. 13 and 14 respectively).

Example 15. In Vivo Efficacy of Anti-CD5 Chimeric Antigen Receptor Expressing Monocytes on CD5 T Lymphoma Model In this example, myeloid cells expressing anti-CD5 chimeric antigen receptor generated according to the methods described in the earlier sections were examined for efficacy in reducing tumor in a mouse H9 T cell lymphoma model. CD5 is expressed on the surface of T cell lymphoma. Anti-CD5 chimeric antigen receptor expressing monocytes are capable of binding CD5-expressing cells. However, whether these anti-CD5-CAR monocytes cells could overcome the TME and exert any anti-tumor potential was tested herein. A T cell lymphoma tumor model was established, in which CD5 positive H9 cells were injected subcutaneously into NSG-SGM3 mice. NSG-SGM3 mouse (Jackson Laboratory, USA) are triple transgenic NSG-SGM3 (NSGS) mice expressing human IL3, GM-CSF and SCF, and combine the features of the highly immunodeficient NOD scid gamma (NSG) mouse with cytokines that support the stable engraftment of myeloid lineages and regulatory T cell populations. H9-mCherry-Luciferase cell line had been derived earlier as follows: H9 cell line was derived from Hut78 Sezary syndrome T cell line; mCherry-firefly Luciferase fusion protein was stably expressed by transfection of Hut78 with pGLCherryluciferase and selected for stable integration. The mCherry positive cells were further enriched by FACS sorting and currently the cell line is over 80% mCherry positive.

Preparation of tumor cells an administration: H9-mCherry-Luc cells were cultured in RPMI1640 with 10% FBS. On day of tumor cell injection, the cells were centrifuged at 1000×g for 3 minutes, the supernatant was removed, and the cells were resuspended in 1:1 diluted Matrigel. 1e6 tumor cells were injected subcutaneously per mouse.

Myeloid cells expressing CD5-CAR (CD-CAR monocytes) were prepared as described above. 200 million cells were electroporated; Post electroporated (EP) monocytes were cultured for 1 hour and cryopreserved. Post thaw analysis showed great viability (>95%). The day of injection of CD5 CAR monocytes was 11 days after implantation of tumors. On the day of treatment with test article, animals were randomized into three groups according to tumor volume (Table 7).

TABLE 7

Dosing regimen in mice.

| Dose # | Injection every 3 days | Amount of cell needed per day (×10⁶) | | |
|---|---|---|---|---|
| | | Ctrl group (5 mice) | One dose (5 mice) | Three dose (5 mice) |
| 1 | Day 0 | 0 | 0.8 | 0.8 |
| 2 | Day 3 | 0 | 0 | 1.4 |
| 3 | Day 6 | 0 | 0 | 1.4 |
| 4 | Day 10 | 0 | 0 | 1.4 |
| 5 | Day 13 | 0 | 0 | 1.4 |
| 6 | Day 16 | 0 | 0 | 1.4 |

CD5-CAR monocytes were cryopreserved in CryoStor CS10 (1 ml per vial, 25M cells).

Cells were thawed quickly in 37° C. water bath and directly injected into animals without further processing. Prior to injection of the CD5 CAR monocytes, the areas to be injected were wiped with a 70% isopropyl or ethyl alcohol solution. CD5 CAR monocytes were administered intravenously. The day of CD5-CAR monocyte adoptive transfer was considered Day 0 of the study. Rest of the injection was performed according to Table 8. Test regime is depicted graphically in FIG. 15.

TABLE 8

Injection schedule for CD5-CAR cells in mice

| Group | Number of mice | Tumor (10⁷ cells, IP) | Dose | Test article |
|---|---|---|---|---|
| 1 | 5 | H9 | NA | NA |
| 2 | 5 | H9 | 0.8 × 10⁶ | CD5-CAR monocyte |
| 3 | 5 | H9 | 0.8 × 10⁶ for one dose, and 1.4 × 10⁶ for five dose | CD5-CAR monocyte |

Tumor measurements and body weights: Animals were observed daily for clinical signs. Tumor volume was determined by imaging using IVIS (Perkin Elmer, Boston, Mass.). Mice were injected IP with luciferin (Biovision, catalog #7903) at a dose or 150 mg/kg (200 ul) and imaged 10 minutes later using IVIS. Radiance values (photons/sec/cm2) were recorded. IVIS imaging and body weight measurements were made on all animals until death or euthanasia. Tumor were removed at Day 20 post injection of the first dose and weighted.

Figure 15A:
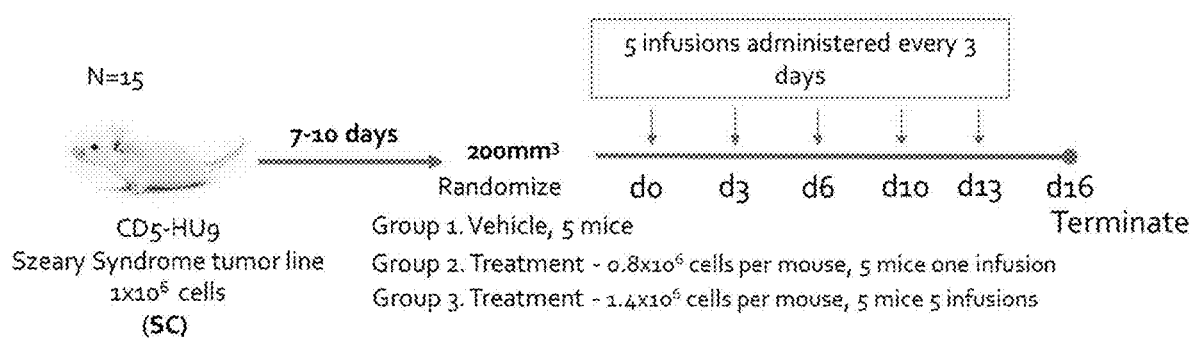
FIG. 15A depicts a schematic showing an exemplary experimental flow diagram of a peripheral T cell lymphoma animal model experiment. Treatment with the indicated amounts of human primary monocytes expressing an anti-CD5 chimeric antigen receptor was initiated at day 11 post tumor seeding. IVIS imaging was used to measure tumor mass.
Figure 15B:
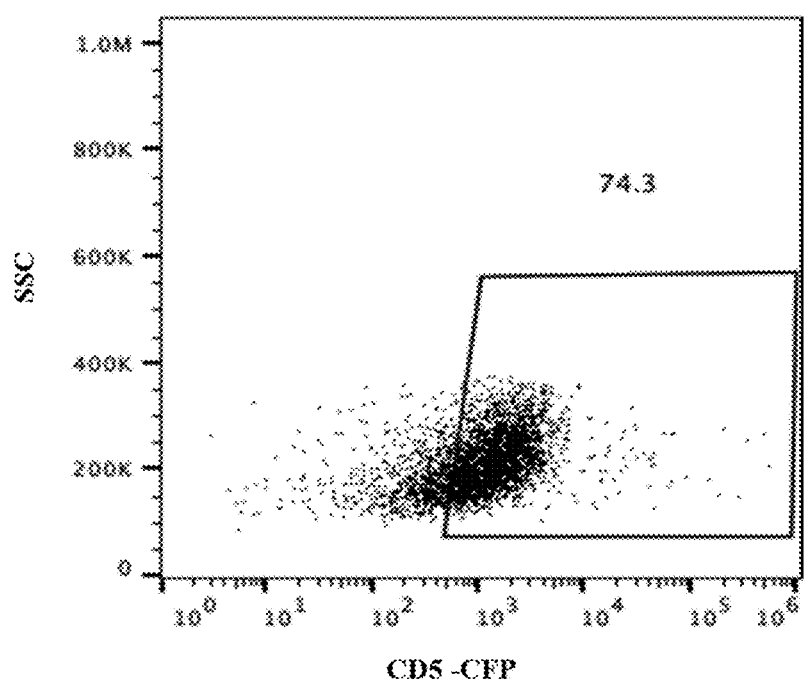
FIG. 15B depicts exemplary flow cytometry data (side scatter (SSC) vs CD5-CFP) after expression of an anti-CD5 chimeric antigen receptors in human primary monocyte cells according to the experiment shown in FIG. 15A.

CD5-CAR monocytes were stained with Alexa488 conjugated human CD5 protein following SOP Culture and electroporation of CD14+ monocyte and binder detection at 24, 48 and 72 hours post thaw. Monocytes electroporated with HER2-CAR constructs were used as negative control to determine the position of the gate. The transfection efficiency was found to be 74% at 24 hours (FIG. 15B). This suggest that electroporation can robustly transfect mRNA into CD14+CD16− monocytes; the expression of the CAR construct was transient with 3-4 days lifetime, potentially due to fast turnover of mRNA and receptor protein.

Figure 15C:
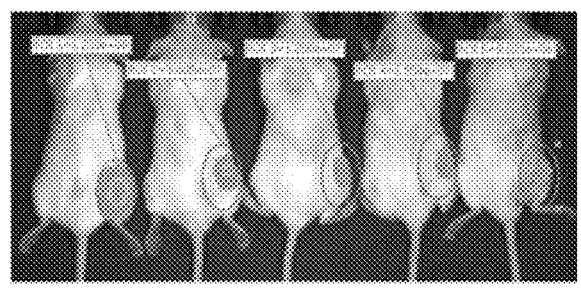
FIG. 15C depicts exemplary results of a mouse xenograft model treated with vehicle or human primary monocytes expressing an anti-CD5 chimeric antigen receptor according to the experiment shown in FIG. 15A. On day 0, NSG mice were injected with CD5+ tumor cells expressing luciferase. Mice were then either untreated or injected with the indicated regimens of human primary monocytes electroporated with an anti-CD5 chimeric antigen receptor.
Figure 15C:
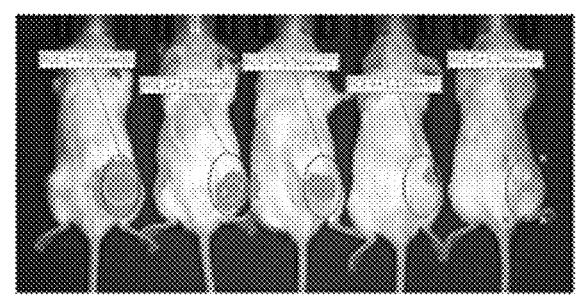
Figure 15C:
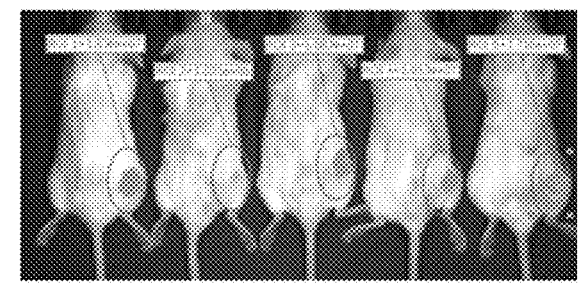
Figure 15D:
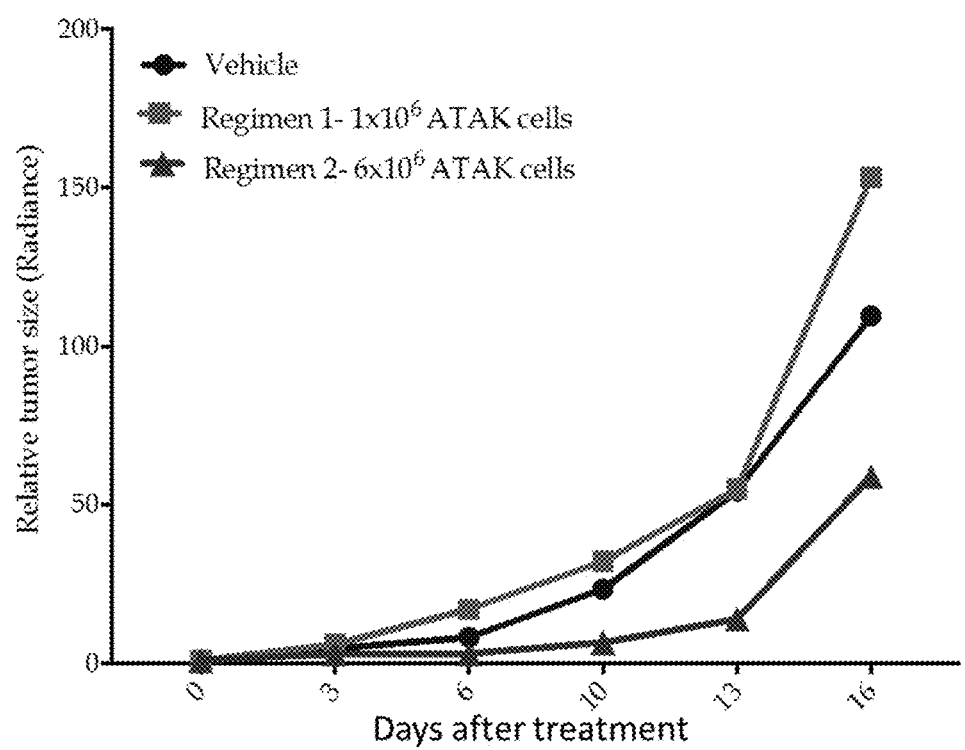
FIG. 15D depicts a graph of relative tumor size over time from the results of FIG. 15C. IVIS imaging of luciferase fluorescence was used to measure tumor mass.

Tumor growth as measured by relative luminescence signal was significantly slower in animals that received 6 dose of 1.4e6 CD5-CAR cells every 3-4 days compared to untreated animals (FIG. 15C and FIG. 15D). Animals receiving only one dose of 1e6 CD5-CAR cells did not show such tumor stasis effect (FIG. 15C and FIG. 15D). In the 6 dose group, one animal died between day 13 and 16. At day 20 several mice have very large tumors that are clearly palpable. All animals were sacrificed at day 20 and their tumors were removed by dissection. Tumors were then weighed on a scale and data were plotted in prism.

Figure 16A:
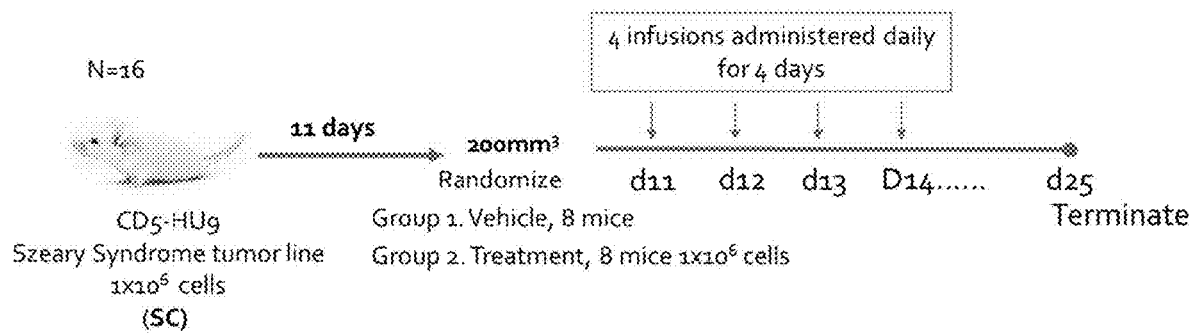
FIG. 16A depicts a schematic showing an exemplary experimental flow diagram of a peripheral T cell lymphoma animal model experiment. Treatment with the indicated amounts of human primary monocytes expressing an anti-CD5 chimeric antigen receptor was initiated at day 11 post tumor seeding.
Figure 16B:
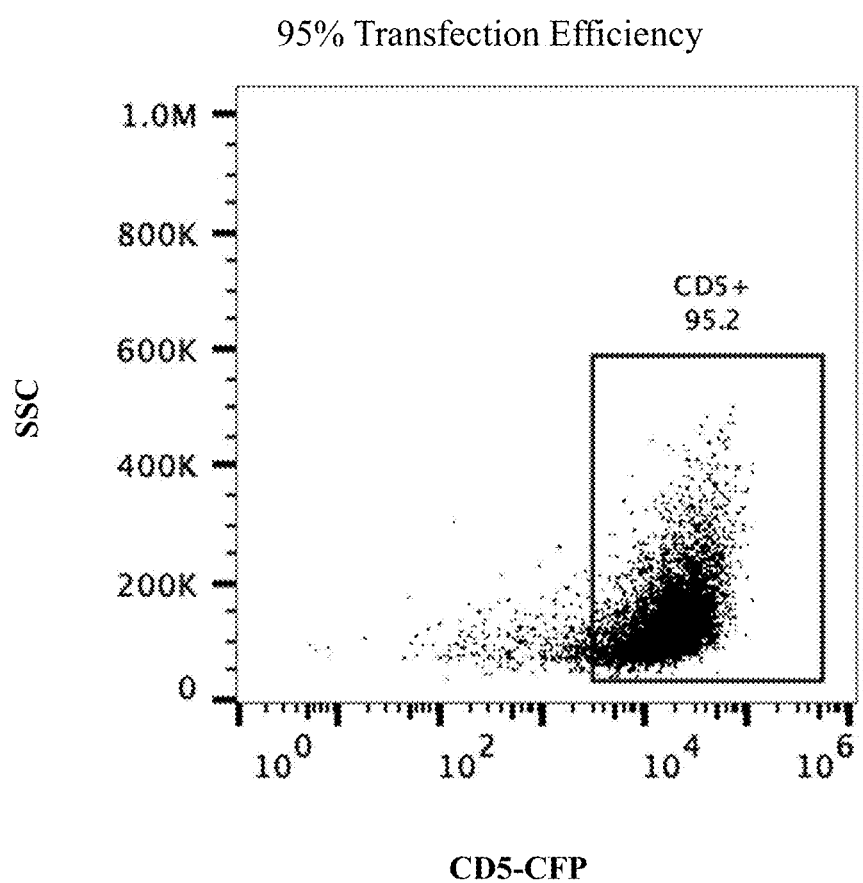
FIG. 16B depicts exemplary flow cytometry data (side scatter (SSC) vs CD5-CFP) after expression of an anti-CD5 chimeric antigen receptors in human primary monocyte cells according to the experiment shown in FIG. 16A. The data shows achievement of 95% transfection efficiency.
Figure 16C:
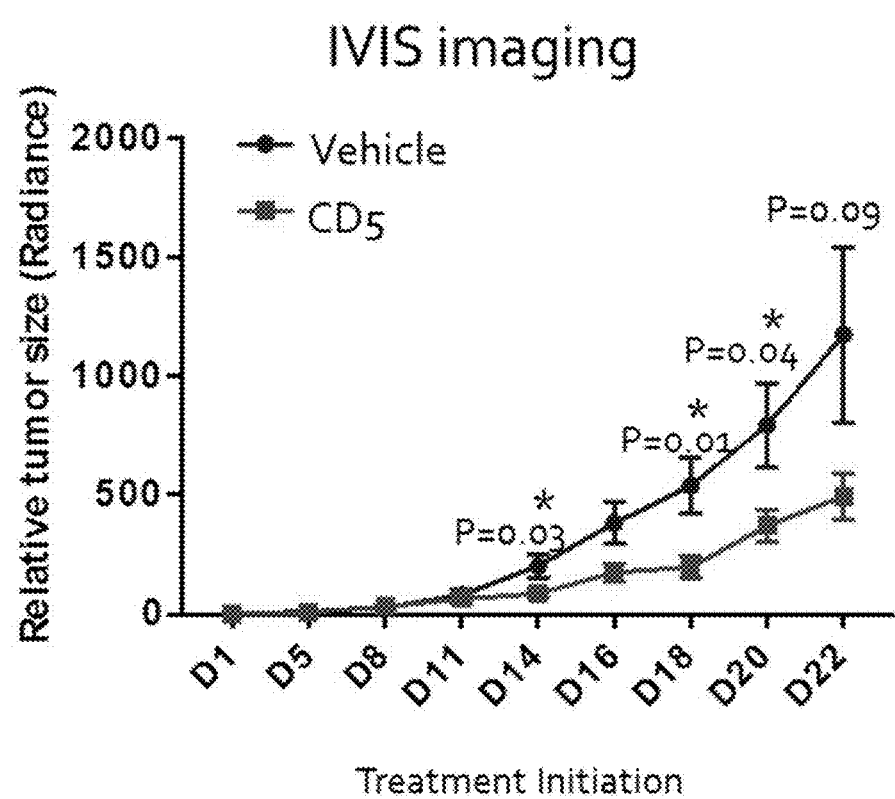
FIG. 16C depicts a graph of relative tumor size over time according to the experiment shown in FIG. 16A. IVIS imaging of luciferase fluorescence was used to measure tumor mass.
Figure 16D:
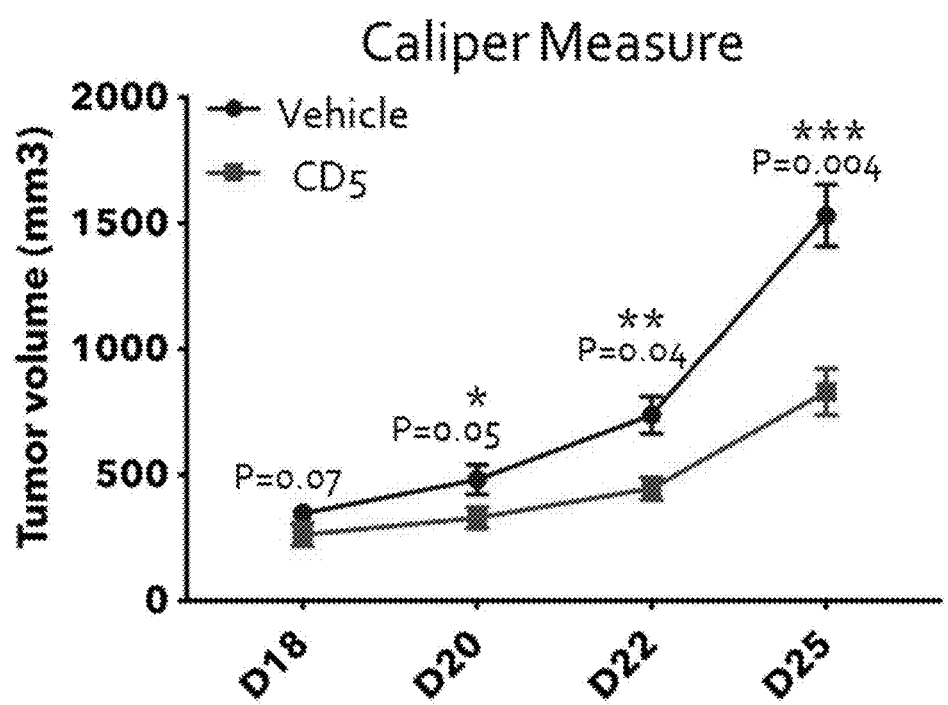
FIG. 16D depicts a graph of relative tumor size over time according to the experiment shown in FIG. 16A. Caliper measure was used to measure tumor mass. The data demonstrates that treatment was associated with delayed tumor progression, and a statistically significant reduction in tumor mass in an immune compromised mouse model. Statistical significance was determined using the Bonferroni-Dunn method, with alpha=0.5. Each row was analyzed individually, without assuming a consistent SD. Number oft tests: 8 or 4.

In another study, NSG-SGM3 mice were subjected to a different dosing scheme, as shown in FIG. 16A. In this regime, mice were administered 4 infusions at day 11, 12, 13 and 14, once daily. CD5-CAR expression was verified after electroporation and was found to be greater than 95% (FIG. 16B). In this assay, statistically significant reduction in tumor growth was recorded, as shown in FIGS. 16C and 16D.

From the study exemplified in this section, it was evident that the multiple infusion of CD5-CAR monocytes targeting CD5+H9 can cause delay of tumor growth. Potentially a higher dose would elicit a much stronger anti-tumor response. NSG-SGM3 mice do not have functional T cells, B cells and NK cells. Therefore, the model is designed to examine the intrinsic anti-tumor activity of the C5-CAR monocytes, which includes phagocytosis and secretion of cytotoxic agents such as TNF alpha and NO/ROS. A much higher anti-tumor activity can be expected in an immune complete model in which the CAR expressing monocytes can cross-present antigen to activate T cells and to secrete inflammatory cytokine to promote lymphocyte infiltration.

What is claimed is:

1. A pharmaceutical composition comprising:
   (a) myeloid cells from a human subject comprising a recombinant polynucleic acid, wherein the myeloid cells are CD14$^+$ and CD16$^-$, and wherein the recombinant polynucleic acid comprises a sequence encoding a chimeric fusion protein (CFP), the CFP comprising:
      (i) an extracellular domain comprising a CD5 binding domain, wherein the CD5 binding domain comprises an scFv comprising a variable heavy chain (VH) sequence with SEQ ID NO: 1 and a variable light chain (VL) sequence with SEQ ID NO: 2,
      (ii) a CD8 transmembrane domain operatively linked to the extracellular domain; and
      (iii) an intracellular domain comprising at least two intracellular signaling domains, wherein the at least two intracellular signaling domains comprise:
         (A) a first intracellular signaling domain derived from FcγR or FcεR, and
         (B) a second intracellular signaling domain comprising a PI3K recruitment domain; and
   (b) a pharmaceutically acceptable carrier;
   wherein the myeloid cells express the CFP and exhibit at least a 1.1 fold increase in phagocytosis of a target cell expressing CD5; and
   wherein the pharmaceutical composition comprises an effective amount of the myeloid cells to inhibit growth of a solid tumor when administered to a human subject with the solid tumor.

2. The pharmaceutical composition of claim 1, wherein the CD5 binding domain binds to CD5 with an affinity of 250 nM or less.

3. The pharmaceutical composition of claim 1, wherein the intracellular domain further comprises one or more additional intracellular signaling domains.

4. The pharmaceutical composition of claim 3, wherein the one or more additional intracellular signaling domains comprise an intracellular signaling domain derived from a receptor other than Megf10, MerTk, FcαR, and Bai1.

5. The pharmaceutical composition of claim 3, wherein the one or more additional intracellular signaling domains comprises a proinflammatory signaling domain.

6. The pharmaceutical composition of claim 3, wherein the one or more additional intracellular signaling domains comprise an intracellular signaling domain derived from an intracellular signaling domain of CD40.

7. The pharmaceutical composition of claim 6, wherein the intracellular signaling domain derived from an intracellular signaling domain of CD40 comprises a sequence with at least 90% sequence identity to SEQ ID NO: 5.

8. The pharmaceutical composition of claim 1, wherein the intracellular domain comprises an intracellular signaling domain with at least 90% sequence identity to SEQ ID NO: 3.

9. The pharmaceutical composition of claim 1, wherein the PI3K recruitment domain comprises a sequence with at least 90% sequence identity to SEQ ID NO: 4.

10. The pharmaceutical composition of claim 1, wherein the CD8 transmembrane domain comprises a sequence with at least 90% sequence identity to SEQ ID NO: 6.

11. The pharmaceutical composition of claim 1, wherein the extracellular domain further comprises a hinge domain derived from CD8, wherein the hinge domain is operatively linked to the transmembrane domain and the CD5 binding domain.

12. The pharmaceutical composition of claim 11, wherein the hinge domain derived from CD8 comprises a sequence with at least 90% sequence identity to SEQ ID NO: 7.

13. The pharmaceutical composition of claim 1, wherein the recombinant polynucleic acid is an mRNA or circRNA.

14. The pharmaceutical composition of claim 1, wherein the CFP comprises a sequence having at least 90% sequence identity to SEQ ID NO: 14.

15. The pharmaceutical composition of claim 1, wherein the pharmaceutical composition comprises at least 6×10$^6$ of the myeloid cells.

16. The pharmaceutical composition of claim 1, wherein the pharmaceutical composition comprises an effective amount of the myeloid cells to inhibit growth of a solid tumor that is T cell lymphoma when administered to a human subject with the solid tumor that is T cell lymphoma.

* * * * *

SEQUENCE LISTING

```
<160> NUMBER OF SEQ ID NOS: 32

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Gln Leu Val Gln Ser Gly Gly Gly Leu Val Lys Pro Gly Gly
1               5                   10                  15
```

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Tyr Cys Arg Arg Leu Lys Ile Gln Val Arg Lys Ala Ala Ile Thr
1               5                   10                  15

Ser Tyr Glu Lys Ser Asp Gly Val Tyr Thr Gly Leu Ser Thr Arg Asn
            20                  25                  30

Gln Glu Thr Tyr Glu Thr Leu Lys His Glu Lys Pro Pro Gln
        35                  40                  45

<210> SEQ ID NO 4
<211> LENGTH: 35
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 4

Tyr Glu Asp Met Arg Gly Ile Leu Tyr Ala Ala Pro Gln Leu Arg Ser
1               5                   10                  15

Ile Arg Gly Gln Pro Gly Pro Asn His Glu Glu Asp Ala Asp Ser Tyr
            20                  25                  30

Glu Asn Met
        35

<210> SEQ ID NO 5
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 7
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60

<210> SEQ ID NO 8

<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Leu
        115                 120                 125

Val Glu
130

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Val Gln Pro Gly Gly Ser Leu Arg Leu Ser Cys Ala Ala Ser Gly
1               5                   10                  15

Phe Asn Ile Lys Asp Thr Tyr Ile His Trp Val Arg Gln Ala Pro Gly
            20                  25                  30

Lys Gly Leu Glu Trp Val Ala Arg Ile Tyr Pro Thr Asn Gly Tyr Thr
        35                  40                  45

Arg Tyr Ala Asp Ser Val Lys Gly Arg Phe Thr Ile Ser Ala Asp Thr
    50                  55                  60

Ser Lys Asn Thr Ala Tyr Leu Gln Met Asn Ser Leu Arg Ala Glu Asp
65                  70                  75                  80

Thr Ala Val Tyr Tyr Cys Ser Arg Trp Gly Asp Gly Phe Tyr Ala
                85                  90                  95

Met Asp Val Trp Gly Gln Gly Thr Leu Val Thr Val
            100                 105

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ser Gly Gly Gly Gly Ser Gly Gly Gly Ser Gly Gly Gly Gly
1               5                   10                  15

Ser

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Gly Gly Gly Ser Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Gly Gly
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Ser
1

<210> SEQ ID NO 14
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
                20                  25                  30

Gly Ser Val Arg Ile Ser Cys Ala Ala Ser Gly Tyr Thr Phe Thr Asn
            35                  40                  45

Tyr Gly Met Asn Trp Val Arg Gln Ala Pro Gly Lys Gly Leu Glu Trp
        50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
            115                 120                 125

Thr Thr Val Thr Val Ser Ser Gly Gly Gly Ser Gly Gly Gly
130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Leu Lys Ile Gln Val Arg Lys Ala Ala Ile Thr Ser Tyr Glu Lys Ser
        355                 360                 365

Asp Gly Val Tyr Thr Gly Leu Ser Thr Arg Asn Gln Glu Thr Tyr Glu
    370                 375                 380

Thr Leu Lys His Glu Lys Pro Pro Gln Gly Ser Gly Ser Tyr Glu Asp
385                 390                 395                 400

Met Arg Gly Ile Leu Tyr Ala Ala Pro Gln Leu Arg Ser Ile Arg Gly
                405                 410                 415

Gln Pro Gly Pro Asn His Glu Glu Asp Ala Asp Ser Tyr Glu Asn Met
            420                 425                 430

<210> SEQ ID NO 15
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Trp Leu Gln Ser Leu Leu Leu Leu Gly Thr Val Ala Cys Ser Ile
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
        50                  55                  60
Ile Tyr Ser Ala Ser Phe Leu Tyr Ser Gly Val Pro Ser Arg Phe Ser
65                  70                  75                  80
Gly Ser Arg Ser Gly Thr Asp Phe Thr Leu Thr Ile Ser Ser Leu Gln
                85                  90                  95
Pro Glu Asp Phe Ala Thr Tyr Tyr Cys Gln Gln His Tyr Thr Thr Pro
            100                 105                 110
Pro Thr Phe Gly Gln Gly Thr Lys Val Glu Ile Lys Arg Thr Gly Ser
        115                 120                 125
Thr Ser Gly Ser Gly Lys Pro Gly Ser Gly Glu Gly Ser Glu Val Gln
130                 135                 140
Leu Val Glu Ser Gly Gly Gly Leu Val Gln Pro Gly Gly Ser Leu Arg
145                 150                 155                 160
Leu Ser Cys Ala Ala Ser Gly Phe Asn Ile Lys Asp Thr Tyr Ile His
                165                 170                 175
Trp Val Arg Gln Ala Pro Gly Lys Gly Leu Glu Trp Val Ala Arg Ile
            180                 185                 190
Tyr Pro Thr Asn Gly Tyr Thr Arg Tyr Ala Asp Ser Val Lys Gly Arg
        195                 200                 205
Phe Thr Ile Ser Ala Asp Thr Ser Lys Asn Thr Ala Tyr Leu Gln Met
    210                 215                 220
Asn Ser Leu Arg Ala Glu Asp Thr Ala Val Tyr Tyr Cys Ser Arg Trp
225                 230                 235                 240
Gly Gly Asp Gly Phe Tyr Ala Met Asp Val Trp Gly Gln Gly Thr Leu
                245                 250                 255
Val Thr Val Ser Ser Ser Gly Gly Gly Ser Gly Ala Leu Ser Asn
            260                 265                 270
Ser Ile Met Tyr Phe Ser His Phe Val Pro Val Phe Leu Pro Ala Lys
        275                 280                 285
Pro Thr Thr Thr Pro Ala Pro Arg Pro Pro Thr Pro Ala Pro Thr Ile
    290                 295                 300
Ala Ser Gln Pro Leu Ser Leu Arg Pro Glu Ala Cys Arg Pro Ala Ala
305                 310                 315                 320
Gly Gly Ala Val His Thr Arg Gly Leu Asp Ile Tyr Ile Trp Ala Pro
                325                 330                 335
Leu Ala Gly Thr Cys Gly Val Leu Leu Leu Ser Leu Val Ile Thr Leu
        340                 345                 350
Tyr Cys Arg Arg Leu Lys Ile Gln Val Arg Lys Ala Ala Ile Thr Ser
    355                 360                 365
Tyr Glu Lys Ser Asp Gly Val Tyr Thr Gly Leu Ser Thr Arg Asn Gln
370                 375                 380
Glu Thr Tyr Glu Thr Leu Lys His Glu Lys Pro Pro Gln Gly Ser Gly
385                 390                 395                 400
Ser Tyr Glu Asp Met Arg Gly Ile Leu Tyr Ala Ala Pro Gln Leu Arg
                405                 410                 415
Ser Ile Arg Gly Gln Pro Gly Pro Asn His Glu Glu Asp Ala Asp Ser
        420                 425                 430
Tyr Glu Asn Met
        435

<210> SEQ ID NO 16
<211> LENGTH: 454

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

```
Leu Lys His Glu Lys Pro Pro Gln Lys Val Ala Lys Pro Thr
385                 390                 395                 400

Asn Lys Ala Pro His Pro Lys Gln Glu Pro Gln Glu Ile Asn Phe Pro
                405                 410                 415

Asp Asp Leu Pro Gly Ser Asn Thr Ala Ala Pro Val Gln Glu Thr Leu
            420                 425                 430

His Gly Cys Gln Pro Val Thr Gln Glu Asp Gly Lys Glu Ser Arg Ile
        435                 440                 445

Ser Val Gln Glu Arg Gln
    450

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Trp Leu Gln Ser Leu Leu Leu Leu Gly Thr Val Ala Cys Ser Ile
1               5                   10                  15

Ser

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
wwwuauuuau uuw                                                      13
```

```
<210> SEQ ID NO 24
<211> LENGTH: 44
<212> TYPE: PRT
<213> ORGANISM: Homo sapiens

<400> SEQUENCE: 24

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

Val Pro Lys Pro Lys Arg Arg Asn Gly Val Asn Phe
        35                  40

<210> SEQ ID NO 25
<211> LENGTH: 50
<212> TYPE: PRT
<213> ORGANISM: Homo sapiens

<400> SEQUENCE: 25

Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45

Phe Lys
    50

<210> SEQ ID NO 26
<211> LENGTH: 56
<212> TYPE: PRT
<213> ORGANISM: Homo sapiens

<400> SEQUENCE: 26

Met Lys Val Arg Ser Ala Gly Gly Asp Gly Asp Ala Leu Cys Val Thr
1               5                   10                  15

Glu Glu Asp Leu Ala Gly Asp Asp Glu Asp Met Pro Thr Phe Pro Cys
            20                  25                  30

Thr Gln Lys Gly Arg Pro Gly Pro Arg Cys Ser Arg Cys Gln Lys Asn
        35                  40                  45

Leu Ser Leu His Thr Ser Val Arg
    50                  55

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ala Ala Pro Ala Ala Ala Pro Ala Lys Gln Glu Ala Ala Ala Pro
1               5                   10                  15

Ala Pro Ala Ala Lys Ala Glu Ala Pro Ala Ala Ala Pro Ala Ala Lys
            20                  25                  30

Ala

<210> SEQ ID NO 28
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units
<220> FEATURE:
<223> OTHER INFORMATION: See specification as filed for detailed
      description of substitutions and preferred embodiments

<400> SEQUENCE: 28

Gly Gly Gly Gly Ser Gly Gly Gly Gly Ser Gly Gly Gly Gly Ser Gly
1               5                   10                  15

Gly Gly Gly Ser
            20

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Gly Gly Gly Gly
1               5

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Glu Ala Ala
      Ala Lys" repeating units
<220> FEATURE:
<223> OTHER INFORMATION: See specification as filed for detailed
      description of substitutions and preferred embodiments

<400> SEQUENCE: 31

Glu Ala Ala Ala Lys Glu Ala Ala Ala Lys Glu Ala Ala Ala Lys Glu
1               5                   10                  15

Ala Ala Ala Lys
            20

<210> SEQ ID NO 32
<211> LENGTH: 12
```

```
<212> TYPE: PRT
<213> ORGANISM: Unknown
<220> FEATURE:
<223> OTHER INFORMATION: Description of Unknown:
      hinge region sequence

<400> SEQUENCE: 32

Glu Ser Lys Tyr Gly Pro Pro Cys Pro Pro Cys Pro
1               5                   10
```